US009428764B2

(12) United States Patent
Flasinski

(10) Patent No.: US 9,428,764 B2
(45) Date of Patent: Aug. 30, 2016

(54) METHODS FOR USING ARTIFICIAL POLYNUCLEOTIDES AND COMPOSITIONS THEREOF TO REDUCE TRANSGENE SILENCING

(71) Applicant: Monsanto Technology LLC, St. Louis, MO (US)

(72) Inventor: Stanislaw Flasinski, Chesterfield, MO (US)

(73) Assignee: Monsanto Technology LLC, St. Louis, MO (US)

( * ) Notice: Subject to any disclaimer, the term of this patent is extended or adjusted under 35 U.S.C. 154(b) by 505 days.

(21) Appl. No.: 13/899,456

(22) Filed: May 21, 2013

(65) Prior Publication Data

US 2014/0007288 A1   Jan. 2, 2014

Related U.S. Application Data

(62) Division of application No. 13/035,898, filed on Feb. 25, 2011, now Pat. No. 8,466,270, which is a division of application No. 12/589,141, filed on Oct. 19, 2009, now Pat. No. 7,919,321, which is a division of application No. 10/521,288, filed as application No. PCT/US03/21551 on Jul. 10, 2003, now Pat. No. 7,615,678.

(60) Provisional application No. 60/396,665, filed on Jul. 18, 2002.

(51) Int. Cl.
*C12N 15/82* (2006.01)
*C12N 9/10* (2006.01)

(52) U.S. Cl.
CPC ......... *C12N 15/8275* (2013.01); *C12N 9/1029* (2013.01); *C12N 9/1092* (2013.01); *C12N 15/8218* (2013.01); *C12N 15/8277* (2013.01)

(58) Field of Classification Search
None
See application file for complete search history.

(56) References Cited

U.S. PATENT DOCUMENTS

| 5,633,435 A | 5/1997 | Barry et al. |
| 6,040,497 A | 3/2000 | Spencer et al. |
| 6,239,331 B1 * | 5/2001 | Drake .................. C12N 9/00 435/320.1 |
| 6,248,876 B1 | 6/2001 | Barry et al. |
| 6,531,649 B1 * | 3/2003 | Mannerloef ............. A01H 1/04 435/469 |

(Continued)

FOREIGN PATENT DOCUMENTS

| WO | WO 97/06269 A1 | 2/1997 |
| WO | WO 97/46690 A1 | 12/1997 |

(Continued)

OTHER PUBLICATIONS

GenBank accession No. AG057893, Pan troglodytes DNA (online Nov. 2), 2001.

(Continued)

*Primary Examiner* — Jason Deveau Rosen
(74) *Attorney, Agent, or Firm* — Dentons US LLP; Pamela Sisson

(57) ABSTRACT

The materials and methods disclosed provide for polynucleotide molecules sufficiently divergent from polynucleotides naturally contained in plants, or polynucleotides previously introduced into plants as transgenes to permit trait stacking in plant breeding methods or plant transformation methods. The disclosure also provides for methods and compositions to detect the polynucleotides of the invention in plants.

10 Claims, 51 Drawing Sheets

```
              1                                                     50
OsEPSPS_Nat ATGGCGGCGA CCATGGCGTC CAACGCCGCG GCTGCGGCGG CGGTGTCCCT
OsEPSPS_AT  .....T..A. .T.....TAG T.....A... .....C..T. .C..T...T.
OsEPSPS_ZM  .....C..T. .G.....TAG T.....G..A ..C..T.... .T..T..G..

51                                                    100
OsEPSPS_Nat GGACCAGGCC GTGGCGGCGT CGGCGGCGTT CTCGTCGCGG AAGCAGCTGC
OsEPSPS_AT  A.....A..A ..A..A...A GC..T..A.. ...A..A..T .....A..A.
OsEPSPS_ZM  A..T.....G ..T..T..CA GC..T..C.. ...CAGTA.. ..A...T.A.

101                                                   150
OsEPSPS_Nat GGCTGCCCGC CGCGGCGCGC GGGGGGATGC GGGTGCGGGT GCGGGCGCGG
OsEPSPS_AT  ....A..A.. A..C..TA.A ..C..C...A .A..TA.A.. .A....TA.A
OsEPSPS_ZM  .T..C..G.. G..T..C..A ..T..A...A .A.....C.. T..A..CA.A 151                                                   200
OsEPSPS_Nat GGGCGGCGGG AGGCGGTGGT GGTGGCGTCC GCGTCGTCGT CGTCGGTGGC
OsEPSPS_AT  ..TA..... ....T..A.. C..A..C... ..T..TAGCA GT........
OsEPSPS_ZM  ..CA.A..T. .....C..... A..C..C..G ..CAGC.... .CAGT..T..

201                                                   250
OsEPSPS_Nat AGCGCCGGCG GCGAAGGCGG AGGAGATCGT GCTCCAGCCC ATCAGGGAGA
OsEPSPS_AT  T........T ..T.....A. ........T.. TT.A..A..T ..T.....A.
OsEPSPS_ZM  T........A ..T.....C. .A..A..T.. T..G..A..G ..AC.....A.

251                                                   300
OsEPSPS_Nat TCTCCGGGGC GGTTCAGCTG CCAGGGTCCA AGTCGCTCTC CAACAGGATC
OsEPSPS_AT  .A..G..... C..A..AT.A ..T..AAG.. ..AGC..T.. ..........T
OsEPSPS_ZM  .T..G..C.. ...G.....C ..T..C..G. .....C..G.. G..TC.T...

301                                                   350
OsEPSPS_Nat CTCCTCCTCT CCGCCCTCTC CGAGGGCACA ACAGTGGTGG ACAACTTGCT
OsEPSPS_AT  ..GT.G..T. .A..T..... G.....A... .....T..... .T..TC,.T.
OsEPSPS_ZM  ..T..G..A. .G..G..G.. ...A..G..C ..G..T..A. .T..TC..T.

351                                                   400
OsEPSPS_Nat GAACAGTGAG GATGTTCACT ACATGCTTGA GGCCCTGAAA GCCCTCGGGC
OsEPSPS_AT  ...T...... .....G..... .T.....A.. ...T..C..G ..T..A....
OsEPSPS_ZM  ....TCC..A ..C..G.... ........C.. A..G..A... ..GT.G..CT
```

(56) References Cited

U.S. PATENT DOCUMENTS

| | | | |
|---|---|---|---|
| 6,762,344 | B1 | 7/2004 | Spencer et al. |
| 7,314,970 | B2 | 1/2008 | Spencer et al. |
| 7,615,678 | B2 | 11/2009 | Flasinski |
| 7,919,321 | B2 | 4/2011 | Flasinski |
| 8,158,850 | B2 | 4/2012 | Feng et al. |
| 8,618,358 | B2 | 12/2013 | Feng et al. |
| 2011/0247103 | A1 | 10/2011 | Flasinski |
| 2012/0317680 | A1 | 12/2012 | Feng et al. |
| 2013/0007908 | A1 | 1/2013 | Huang et al. |
| 2013/0291138 | A1 | 10/2013 | Feng et al. |
| 2014/0109250 | A1 | 4/2014 | Feng et al. |

FOREIGN PATENT DOCUMENTS

| | | |
|---|---|---|
| WO | WO 01/44457 A2 | 6/2001 |
| WO | WO 02/26995 A1 | 4/2002 |

OTHER PUBLICATIONS

Hamilton, et al., "Two Classes of Short Interfering RNA in RNA Silencing", *EMBO J.*, 21(17):4671-4679, 2002.

Han, et al., "Relationship Between Small Antisense RNAs and Aberrant RNAs Associated with Sense Transgene Mediated Gene Silencing in Tomato", *Plant J.*, 29(4):509-519, 2002.

Klahre, et al., "High Molecular Weight RNAs and Small Interfering RNAs Induce Systemic Posttranscriptional Gene Silencing in Plants", *PNAS*, 99(18):11981-11986 Sep. 2002

Kumpatla, et al., "Genome intruder scanning and modulation systems and transgene silencing", *Trends in Plant Science*, 3(3):97-104, 1998.

Meyer, "Understanding and controlling transgene expression", *Trends in Biotechnology*, 13(9):332-337, 1995.

Murray, et al., "Codon usage in plant genes", *Nucleic Acid Research*, 17(2):477-498, 1989.

New England Biolabs 96/97 Catalog (1996), p. 111.

Thierry, et al., "Sequence Homology Requirements for Transcriptional Silencing of 35S transgenes and Post-Transcriptional Silencing of Nitrite Reductase (Trans)Genes by the Tobacco 271 Locus", *Plant Mol. Biol.*, 32:1075-1083, 1996.

Thomas, et al., "Size constraints for targeting post-transcriptional gene silencing and for RNA-directed methylation in *Nicotiana benthamiana* using a potato virus X vector", *The Plant Journal* 25(4):417-425, 2001.

\* cited by examiner

```
              1
OsEPSPS_Nat ATGGCGGCGA CCATGGCCGTC CAACGCCGCG GCTGCGGGCGG CGGTGTCCCT
OsEPSPS_AT  .....T..A.. .T.....TAG  T......A...  .....C..T.  .C..T...T.
OsEPSPS_ZM  .....C..T.  .G.....TAG  T......G..A  ..C..T....  .T..T...G..

51                                                     100
OsEPSPS_Nat GGACCAGGCC GTGGCGGGCGT CGGCGGGCGT CTCGTCGCGG AAGCAGCTGC
OsEPSPS_AT  A......A..  ..A..A...A  GC..T..A..  ...A..A..T  ....A...A.
OsEPSPS_ZM  A..T.....G  .T..T..CA  GC..T..C..  ...CAGTA..  ..A...T.A.

101                                                     150
OsEPSPS_Nat GGCTGCCCGC CGCGGGCGCGC CGGGGGATGC GGGTGCGGG GCGGGGCGCGG
OsEPSPS_AT  ...A..A..  A..C..TA.A  ..C...A  .A..TA.A.  .A....TA.A
OsEPSPS_ZM  .T..C..G..  G..T..C..A  .T..A..A  .A......C..  T.A..CA.A 151                                                     200
OsEPSPS_Nat GGGCGGGCGGG AGGCGGTGGT GGTGGGCGTCC GCGTCGTCGT CGTCGGTGGC
OsEPSPS_AT  ..TA......  .T..A..  C..A..C...  ..T..TAGCA  GT........
OsEPSPS_ZM  ..CA..A..T  .....C....  A..C..C..G  ..CAGC....  .CAGT..T..

Figure 1
```

```
              201                                                        250
OsEPSPS_Nat   AGCGCCGGCG GCGAAGGCGG AGGAGATCGT GCTCCAGCCC ATCAGGGAGA
OsEPSPS_AT    T........T ..T....A.. .......T.. TT.A..A.T. ..T.....A.
OsEPSPS_ZM    T........A ..T.....C. .A..A..T.. T..G..A..G ..AC.....A.

251                                                        300
OsEPSPS_Nat   TCTCCGGGGC GGTTCAGCTG CCAGGGTCCA AGTCGCTCTC CAACAGGATC
OsEPSPS_AT    .A..G..... C..A..AT.A ..T..AAG.. .AGC..T... ..........T
OsEPSPS_ZM    .T..G..C.. ...G.....C ..T..C..G. ....C..G.. G..TC.T...

301                                                        350
OsEPSPS_Nat   CTCCTCCTCT CCGCCCTCTC CGAGGGCACA ACAGTGGTGG ACAACTTGCT
OsEPSPS_AT    ..GT.G..T. .A.T..... G....A.... .......... T..TC..T..
OsEPSPS_ZM    ..T..G..A. .G..G..G.. ...A.G..C. ..G..T..A. .T..TC..T.

351                                                        400
OsEPSPS_Nat   GAACAGTGAG GATGTTCACT ACATGCTTGA GGCCCTGAAA GCCCTCGGGC
OsEPSPS_AT    ...T...... ......G... ..T.....A. ...T..C..G ..T..A....
OsEPSPS_ZM    ....TCC..A ..C..G.... ........C. A..G..A... ..GT.G..CT
```

Figure 1 (Continued)

```
              401                                                             450
OsEPSPS_Nat   TCTCTGTGGA AGCAGATAAA GTTGCAAAAA GAGCTGTAGT CGTTGGCTGT
OsEPSPS_AT    .T....A... ...G...... ..A.....C  .C..A..G.. T..A..T...
OsEPSPS_ZM    .GAGC..T.. G..T..C... .G..C..GC. ....A.C... A..G..A..C 451                                                             500
OsEPSPS_Nat   GGTGGCAAGT TTCCTGTTGA GAAGGATGCG AAAGAGGAAG TGCAACTCTT
OsEPSPS_AT    .....G.... .C..A....T A......T.. .G.A...... .A.G......
OsEPSPS_ZM    ..C..T.... .C..A..G.. ...A..C..C .....A.G.. .T...T.G..

501                                                             550
OsEPSPS_Nat   CTTGGGGAAC GCTGGAATCG CAATGCGATC CTTGACAGCA GCCGTGACTG
OsEPSPS_AT    TC.C......T  ..C..G.... .C....GAG  T.....T..T ..G..C..A.
OsEPSPS_ZM    ......A... .....C.... ......A..AG .C....T..C ..G..C....

551                                                             600
OsEPSPS_Nat   CTGCTGGTGG AAATGCAACT TATGTGCTTG ATGGAGTGCC ACGAATGAGG
OsEPSPS_AT    .C.....A.. C..C...A.. .C..C..A.. ...G...... GA.....C.T
OsEPSPS_ZM    .C..A..G.. T......... .C..C..G.. .C..T..T.. ..G....C.C
```

Figure 1 (Continued)

```
             601
OsEPSPS_Nat  GAGAGACCGA TTGGTGACTT GGTTGTCGGG TTGAAACAAC TTGGTGCGGA
OsEPSPS_AT   ...C.T..T. ........TC. T.C..A..T C.C..G.... .C..C..T..
OsEPSPS_ZM   ..AC.....C. .C......TC. C..G..A..A C.T......T .G..A..C..
             651                                                    650
OsEPSPS_Nat  TGTCGACTGT TTCCTTGGCA CTGAATGCCC ACCTGTTCGT GTCAAGGGAA
OsEPSPS_AT   C..A..T... .....G..T. .....G..T.. G..A..CA.A ..T..A....
OsEPSPS_ZM   ...A..T... ...T.G..G. .A..G..... T..A..G..G ..A......C.
             701                                                    700
OsEPSPS_Nat  TTGGAGGACT TCCTGGGTGGC AAGGTTAAGC TCTCTGGTTC CATCAGCAGT
OsEPSPS_AT   .C..T..G.. G..G..C..A ........C... .G..G..CAG T..TTCG...
OsEPSPS_ZM   .C..G..T.. C..A..C..A .......T .A..A..GAG T...TC.TCG
             751                                                    750
OsEPSPS_Nat  CAGTACTTGA GTGCCTTGCT GATGGCTGCT CCTTTGGCCC TTGGGGATGT
OsEPSPS_AT   .....TC.TT C..TC.C.. ..........G ..A.A..TT .G..A.....
OsEPSPS_ZM   .....C.CT CC..GC..T. ......A..A .AC.....GT .G..C..C..
                                                                   800
```

Figure 1 (Continued)

```
             801                                                         850
OsEPSPS_Nat  GGAGATCGAA ATCATTGACA AACTAATCTC CATTCCTTAC GTTGAAATGA
OsEPSPS_AT   T........G .........T ....T..A.. T..C..G..T ..C..G.....
OsEPSPS_ZM   T..A..T... ..T..C.... .G..C..A.. ...C..G..T ..G..G.....

851                                                         900
OsEPSPS_Nat  CATTGAGAGATT GATGGAGCGT TTTGGTGTGA AGGCAGAGCA TTCTGATAGT
OsEPSPS_AT   .T..A...C. T......A..G .....G..T. ....C..... .AGC..C...
OsEPSPS_ZM   ..C..C.GC. .......AA.A ..........A. .A..T..A.. .AG...CTC.

901                                                         950
OsEPSPS_Nat  TGGGACAGAT TCTATATTAA GGGAGGGCAG AAGTACAAAT CTCCTGGAAA
OsEPSPS_AT   .....TC.T. ....C..A.. ........C. ....T..G.. .......G..
OsEPSPS_ZM   .....TC.G. ....C..C.. .....C..A.. ..A..T..GA G...A..C..

951                                                        1000
OsEPSPS_Nat  TGCCTATGTT GAAGGTGATG CCTCAAGCGC GAGCTATTTC TTGGCTGGTG
OsEPSPS_AT   ...T......A .....G.... .T...TCT.. .TCT..C... C.T..G..A.
OsEPSPS_ZM   ...G..C..G ..G..C..C. .......TTC... C.......C. .....A..C.
```

Figure 1 (Continued)

```
                    1001                                                               1050
OsEPSPS_Nat   CTGCAATCAC TGGAGGCACT GTGACAGTTC AAGGTTGTGG TACGACCAGT
OsEPSPS_AT    .G..T..A.. .......A.A ..C....... .G..C.C... ...A..A...
OsEPSPS_ZM    .A..T..T.. .......C.. .T.....G.. .......G.. A..A..G..C 1051                                                               1100
OsEPSPS_Nat   TTGCAGGGTG ATGTCAAATT TGCTGAGGTA CTTGAGATGA TGGGAGCAAA
OsEPSPS_AT    .....A.... .C..G..G.. .......C.. .......A.. ....T..C..
OsEPSPS_ZM    C....A..C. .C..A..G.. C..A..G... .......A.. ....C..T..

1101                                                               1150
OsEPSPS_Nat   GGTTACATGG ACTGACACCA GTGTAACCGT AACTGGTCCA CCACGTGAGC
OsEPSPS_AT    A..A..G... .A.....AT CG..G.A.. T........T ....A..A.A.
OsEPSPS_ZM    ...G..T... .A..T..GT CA..C..... C......G.T .T.G..A..

1151                                                               1200
OsEPSPS_Nat   CTTATGGGAA GAAACACCTG AAAGCTGTTG ATGTCAACAT GAACAAAATG
OsEPSPS_AT    ...C..C... A..G..T..T ..G..C..G. ....T..T.. ....T..G...
OsEPSPS_ZM    .C..C..T.. .......T.. ..G..A..G. .C..G..... ....T..G...
```

Figure 1 (Continued)

```
            1201
OsEPSPS_Nat CCTGATGTTG CCATGACCCT TGCCGTTGTT GCACTCTTCG CTGATGGTCC
OsEPSPS_AT  .....C.... ....T..A.. .......... ..C..T..T. .A..C..C..
OsEPSPS_ZM  ..A..C.... .......G.. C..A..A..C ..T..G.... .A..C..A..

1251                                                  1300
OsEPSPS_Nat AACTGCTATC AGAGATGTGG CTTCCTGGAG AGTAAAGGAA ACCGAAAGGA
OsEPSPS_AT  ...G..G..A C.C.....T. .A..A...C. C..C...... ..G..G....
OsEPSPS_ZM  T..C.....T ..G..C..T. ..AGT..... G..C.....G ..T..G..A.

1301                                                  1350
OsEPSPS_Nat TGGTTGCAAT TCGGACCGAG CTAACAAAGC TGGGAGCATC GGTTGAAGAA
OsEPSPS_AT  ....G..T.. ...A..T..A ..C..C..A. .T..C..T.. T..A..G..G
OsEPSPS_ZM  ....C..T.. C..C.....A ..T..G..A. .C..T...AG C..G..G...

1351                                                  1400
OsEPSPS_Nat GGTCCTGACT ACTGCATCAT CACCCCACCG GAGAAGCTGA ACATCACGGC
OsEPSPS_AT  ..C.....T. ........T. T..A..C..T .....A..T. ......T...
OsEPSPS_ZM  .....A.... .......... A..G..T..C .....C.... ....A..C..
```

Figure 1 (Continued)

```
                1401                                                              1450
OsEPSPS_Nat  AATCGACACC TACGATGATC ACAGGATGGC CATGGCCTTC TCCCTCGCTG
OsEPSPS_AT   T..T..T..A .......C.. .T..A..... T......T.. ..A..G..C.
OsEPSPS_ZM   T..A.....T .......C.. ...A...... G........G ........A.

1451                                                              1500
OsEPSPS_Nat  CCTGCGCCGA CGTGCCCGTG ACGATCAGGG ACCCTGGTTG CACCCGCAAG
OsEPSPS_AT   .T..T..A.. T..T..T..C ..A....A.. .T.....C.. T..TA.A...
OsEPSPS_ZM   .G......G. ..T..G..T  .....T..A. .T......G. ...T..T..A 1501                                                              1548
OsEPSPS_Nat  ACCTTCCCCA ACTACTTCGA CGTTCTAAGC ACTTTCGTCA GGAACTGA
OsEPSPS_AT   ..G......G. .......T.. ....T....TTCA ..A......C .C..T...
OsEPSPS_ZM   ..T......T. .T........ T..G...TCA ..C..T..AC .C......
```

Figure 1 (Continued)

```
                     1                                                        50
ZmEPSPS_Nat  ATGGCGGGCCA TGGCGGACCCT GGCCGCCGCG GGCACCGTGT CGCTGGACCT
ZmEPSPS_ZM   .........T. ....C.G... ...A.G.C.. ..T..A..AA GC...C...TT.

51                                                       100
ZmEPSPS_Nat  CGCCGCGGCCG TCGCGGCCGCC ACCACCGCCC GAGCTCGGCG CGCCCGCCCT
ZmEPSPS_ZM   G..G.C..C.. ..C..TA.G.. ........G.. A...AGT... A.G..A...G.

101                                                       150
ZmEPSPS_Nat  TCCGCCCCGC CGTCCGCGGG CTGCGGGGCG CTGGGGCGCC CGTGATCGCC
ZmEPSPS_ZM   ..A.G..A.. A..T.....T ..TA.A.... ....TA.AA. G..T.....A 151                                                       200
ZmEPSPS_Nat  GCGGCCGCCGG CGGGGGACAGC GGCGGGGCGGG GTGCAGGGCGG GTGCCGAGGA
ZmEPSPS_ZM   .....A..... ...T..C.. T... ....A...... ....C. ..C..G..A..

201                                                       250
ZmEPSPS_Nat  GATCGTGCTG CAGCCCATCA AGGAGATCTC CGGCACCGTC AAGCTGCCGG
ZmEPSPS_ZM   ......C..A .....T.... ....A..... T..T..G..A ...T.A..A.
```

Figure 2 (Continued)

```
                      251                                                            300
ZmEPSPS_Nat  GGTCCAAGTC GCTTTCCAAC CGGATCCTCC TACTCGCCGC CCTGTCCGAG
ZmEPSPS_ZM   .CAG...AAG T...AG.... ..A.....G. .GT.G..G.. A..C..T..A 301                                                            350
ZmEPSPS_Nat  GGGACAACAG TGGTTGATAA CCTGCTGAAC AGTGAGGATG TCCACTACAT
ZmEPSPS_ZM   .....C.G.. .C..A..... T......C.. ..C..A..C. .G......T..

351                                                            400
ZmEPSPS_Nat  GCTCGGGGCC TTGAGGACTC TTGGTCTCTC TGTCGAAGCG GACAAAGCTG
ZmEPSPS_ZM   .T.G..T... C......G. .A.....G.. A..G.....C ..T..G..C.

401                                                            450
ZmEPSPS_Nat  CCAAAAGAGC TGTAGTTGTT GGCTGTGGTG GAAAGTTCCC AGTTGAGGAT
ZmEPSPS_ZM   ....GC.C.. ......C.C. .......... .......T.. C..G.....C 451                                                            500
ZmEPSPS_Nat  GCTAAAGAGG AAGTGCAGCT CTTCTTGGGG AATGCTGGAA TCGCAATGCG
ZmEPSPS_ZM   ..G......A. .G......T. A..TC.T... ..C.....C. ....C.....
```

Figure 2 (Continued)

```
            501
ZmEPSPS_Nat GTCCTTGACA GCAGCTGTTA CTGCTGCTGG TGGAAATGCA ACTTACGTGC
ZmEPSPS_ZM  ....C.T..C ..........C..C. .C......G.. A..C..C...  ..........
Consensus   .....c..g..a .......... ..c......c. .c......g.. a..a...c..  ..........

551                                                      600
ZmEPSPS_Nat TTGATGGAGT ACCAAGAATG AGGGAGAGAC CCATTGGCGA CTTGGTTGTC
ZmEPSPS_ZM  ....C..T.. T..TC.T... ..A...C.G. ...A..G... TC.C..C..G 601                                                      650
ZmEPSPS_Nat GGATTGAAGC AGCTTGGTGC AGATGTTGAT TGTTCCTTG  GCACTGACTG
ZmEPSPS_ZM  ..GC.C.... ........C..G.. C..C...... ..C......C. .A..C.....

651                                                      700
ZmEPSPS_Nat CCCACCTGTT CGTGTCAATG GAATCGGAGG GCTACCTGGT GGCAAGGTCA
ZmEPSPS_ZM  ..C......G A.G..G..C. .C......G.. A.G..A..A  .....A....

701                                                      750
ZmEPSPS_Nat AGCTGTCTGG CTCCATCAGC AGTCAGTACT TGAGTGCCTT GCTGATGGCT
ZmEPSPS_ZM  ..T......C.. ...A..TTC. TCG......C .....C....T .......G
```

Figure 2 (Continued)

```
              751
ZmEPSPS_Nat  GCTCCCTTTGG CTCTTGGGGA TGTGGAGATT GAAATCATTG ATAAATTAAT   800
ZmEPSPS_ZM   ..C....C... ....G..A.. C..C..A... .G........ ....GC.G..

801
ZmEPSPS_Nat  CTCCATTCCG TACGTCGAAA TGACATTGAG ATTGATGGAG CGTTTTGGTG    850
ZmEPSPS_ZM   ...T..C..T .T..T..G.. .....C.CC. TC......A A.A..C..G.

851
ZmEPSPS_Nat  TGAAAGCAGA GCATTCTGAT AGCTGGGACA GATTCTACAT TAAGGGAGGT    900
ZmEPSPS_ZM   .C......T.. ...C..C... TC........ .G.....T.. C.....C..A

901
ZmEPSPS_Nat  CAAAAATACA AGTCCCCTAA AAATGCCTAT GTTGAAGGTG ATGCCTCAAG    950
ZmEPSPS_ZM   ..G.....T. ....A..G.. G.....G..C ..C..G..A. .C..A..G..

951
ZmEPSPS_Nat  CGCAAGCTAT TTCTTGGCTG GTGCTGCAAT TACTGGAGGG ACTGTGACTG   1000
ZmEPSPS_ZM   ...G..T..C ..C..T..G. .C......C. C...C..G..A ..C......A.
```

Figure 2 (Continued)

```
               1001                                                      1050
ZmEPSPS_Nat  TGGAAGGTTG TGGCACCACC AGTTTGCAGG GTGATGTGAA GTTTGCTGAG
ZmEPSPS_ZM   .........C. ...G..A..G ..C....... .C..C..C.. A.........

1051                                                      1100
ZmEPSPS_Nat  GTACTGGAGA TGATGGGAGC GAAGGTTACA TGGACCCGAGA CTAGCGTAAC
ZmEPSPS_ZM   ..G..A..A. .........C.. T.....G..T .....T.... .GTC...G..

1101                                                      1150
ZmEPSPS_Nat  TGTTACTGGC CCACCGGCGG AGCCATTTGG GAGGAAACAC CTCAAGGCGA
ZmEPSPS_ZM   C.....G..A .G..C..C. .A..T..C.. CC....G..T ..G..A....

1151                                                      1200
ZmEPSPS_Nat  TTGATGTCAA CATGAACAAG ATGCCTGATG TCGCCATGAC TCTTGCTGTG
ZmEPSPS_ZM   .........G. .........T... .....G..C. ....T..... A......C..

1201                                                      1250
ZmEPSPS_Nat  GTTGCCCTCT TTGCCGATGG CCCGACAGCC ATCAGAGACG TGGCTTCCTG
ZmEPSPS_ZM   ..G......G. .C..T..C.. ...C...C..A .....G..T. .C....AGT..
```

Figure 2 (Continued)

```
              1251                                                          1300
ZmEPSPS_Nat   GAGAGTAAAG  GAGACCGAGA  GGATGGTTGC  GATCCGGACG  GAGCTAACCA
ZmEPSPS_ZM    ...G..C...  .....A...C  .T.....G..  .....A....  .....G..T.

1301                                                          1350
ZmEPSPS_Nat   AGCTGGGAGC  ATCTGTTGAG  GAAGGGCCGG  ACTACTGCAT  CATCAGGCCG
ZmEPSPS_ZM    .A..C..G..  CAG....G..  ..G..C....  .T........  A.....A..T 1351                                                          1400
ZmEPSPS_Nat   CCGGAGAAGC  TGAACGTGAC  GGCGATCGAC  ACGTACGACG  ACCACAGGAT
ZmEPSPS_ZM    ..A.......T  ........C.  C..T......  ..A.......  .T...C....

1401                                                          1450
ZmEPSPS_Nat   GGCCATGGCC  TTCTCCCTTG  CCGCCTGTGC  CGAGGTCCCC  GTCACCATCC
ZmEPSPS_ZM    ...A......  ..TAG.T.G.  .A..G..C..  ...A..A..T  ..G..T..AA 1451                                                          1500
ZmEPSPS_Nat   GGGACCCTGG  GTGCACCCGG  AAGACCTTCC  CCGACTACTT  CGATGTGCTG
ZmEPSPS_ZM    .A..T..A..  T.......C.  ..A..G..T.  .........T  ...C..C..C 1501        1521
ZmEPSPS_Nat   AGCACTTTCG  TCAAGAATTA  A
ZmEPSPS_ZM    TCA..C....  .G.....C.G  .
```

Figure 2 (Continued)

```
                  1                                                                       50
GmEPSPS_Nat  ATGGCCCAAG TGAGCAGAGT GCACAATCTT GCTCAAAGCA CTCAAATTTT
GmEPSPS_GM   .....T..G. .CTCTC.C.. T..T.....C .....G..T. .C..G..A..

51                                                                     100
GmEPSPS_Nat  TGGCCATTCT TCCAACTCCA ACAAACTCAA ATCGGTGAAT TCGGTTTCAT
GmEPSPS_GM   C..A.....C AGT......A. ........A.. .....G..T. AGT..A...C 101                                                                     150
GmEPSPS_Nat  TGAGGCCACG CCTTTGGGGG GCCTCAAAAT CTCGCATCCC GATGCATAAA
GmEPSPS_GM   .TC....T.. G..G.....A ..AAGT..GA GC..T..... T......C..G 151                                                                     200
GmEPSPS_Nat  AATGGAAAGCT TTATGGGAAA TTTTAATGTG GGGAAGGGAA ATTCCGGCGT
GmEPSPS_GM   ..C..TTCG. .C.....G.. C.....C..C ..C..A.... .C..A..T..

201                                                                     250
GmEPSPS_Nat  GTTTAAGGTT TCTGCATCGG TCGCCGCCGC AGAGAAGCCG TCAACGTCGC
GmEPSPS_GM   C...C...A..A AGC..CAGC. .A..T..G.. T........C AGT..T..T.
```

Figure 3 (Continued)

```
           251
GmEPSPS_Nat  CGGAGATCGT GTTGGAACCC ATCAAAGACT TCTCGGGTAC CATCACATTG    300
GmEPSPS_GM   .T..A..T.. TC.T......G ..A..G..T. ....A..... G..T...C.A

301
GmEPSPS_Nat  CCAGGGTCCA AGTCTCTGTC CAATCGAATT TTGCTTCTTG CTGCTCTCTC    350
GmEPSPS_GM   ..T..A..A. ..AG....C.. T...A..... ...T.G..C. .A.....G..

351
GmEPSPS_Nat  TGAGGGAACA ACTGTTGTAG ACAACTTGTT GTATAGTGAG GATATTCATT    400
GmEPSPS_GM   C..A......C .....A..C. .T..C.CC.. T......C..A T.....A....

401
GmEPSPS_Nat  ACATGCTTGG TGCATTAAGG ACCCTTGGAC TGCGTGTGGA AGATGACAAA    450
GmEPSPS_GM   .T...T.G.. G..GC.C..A ..T......G. .AA.A..T.. G..C..T..G

451
GmEPSPS_Nat  ACAACCAAAC AAGCAATTGT TGAAGGCTGT GGGGATTGT TTCCACTAG    500
GmEPSPS_GM   ..T.T..... ....T:.C.. C.....T... ..C..G.... .C..T...TC
```

Figure 3 (Continued)

```
              501
GmEPSPS_Nat   TAAGGAATCT AAAGATGAAA TCAATTTATT CCTTGGAAAT GCTGGTATCG
GmEPSPS_GM    ..A...AG.  .........G. .A..C..G.. T......C..C ..A..A....

551                                                600
GmEPSPS_Nat   CAATGAAGTC CTTGACAGCA GCTGTGGTTG CTGCAGGTGG AAATGCAAGC
GmEPSPS_GM    ........AG .C.C.C..T ......C.... .G.G...... T..C..T..T 601                                                650
GmEPSPS_Nat   TACGTACTTG ATGGGGTGCC CCGAATGAGA GAGAGGCCAA TTGGGGATTT
GmEPSPS_GM    .....CT.A. .C.C...... TA.....C.. ..A..A..T. .C..T...C.

651                                                700
GmEPSPS_Nat   GGTTGCTGGT CTTAAGCAAC TTGGGTGCAGA TGTTGATTGC TTTCTTGGCA
GmEPSPS_GM    A..G.....C ..A..A..G. ......A..... C..C......T ..CT.G....

701                                                750
GmEPSPS_Nat   CAAACTGTCC ACCTGTTCGT GTAAATGGGA AGGGAGGACT TCCTGGCGGA
GmEPSPS_GM    ....T..C.. G..C..GA.A .G.C..... .......CT. G..A....T
```

Figure 3 (Continued)

```
       751                                                                          800
GmEPSPS_Nat  AAGGTGAAAC TGTCTGGATC AGTTAGCAGT CAATACTTGA CTGCTTTGCT
GmEPSPS_GM   .....T.... .A..C..... G..CTCGTCA ..G...C.A. .....A....

801                                                                          850
GmEPSPS_Nat  TATGGCAGCT CCCTTAGCTC TTGGTGATGT GGAAATTGAG ATTGTTGATA
GmEPSPS_GM   C.....C..C ..GC.C...T .G..G.C... ...G.....A ..C..C....

851                                                                          900
GmEPSPS_Nat  AACTGATTTC TGTTCCATAT GTTGAAATGA CTCTGAAGTT GATGGAGCGT
GmEPSPS_GM   GT.....AG C..G..T... ..G....... .C..C..A.. ......A.G 901                                                                          950
GmEPSPS_Nat  TTTGGAGTTT CTGTGGAACA CAGTGGTAAT TGGGATAGGT TCTTGGTCCA
GmEPSPS_GM   ..C....... .G..A..... .TCC..G... ......C... .TC.T..A..

951                                                                         1000
GmEPSPS_Nat  TGGAGGTCAA AAGTACAAGT CTCCTGGCAA TGCTTTTGTT GAAGGTGATG
GmEPSPS_GM   C.....G... ........AA GC..A..... ..C...C..C .....G..C.
```

Figure 3 (Continued)

```
              1001                                                                    1050
GmEPSPS_Nat   CTTCAAGTGC CAGTTATTTA CTAGCTGGTG CAGCAATTAC TGGTGGGACT
GmEPSPS_GM    ...G..C..  TTCC...C.C ..C...... ...C..A..  C.....C..C 1051                                                                    1100
GmEPSPS_Nat   ATCACTGTTA ATGGCTGTGG CACAAGCAGT TTACAGGGAG ATGTAAAATT
GmEPSPS_GM    ..A.C..G.  .C......C. ...CTCATCC C.T..A..T. .........G..

1101                                                                    1150
GmEPSPS_Nat   TGCTGAAGTT CTTGAAAAGA TGGGAGCTAA GGTTACATGG TCAGAGAACA
GmEPSPS_GM    C.....G..C T.G..G..A. ...C..A.. ...C......  ......T...

1151                                                                    1200
GmEPSPS_Nat   GTGTCACTGT TTCTGGACCA CCACGAGATT TTTCTGGTCG AAAAGTCTTG
GmEPSPS_GM    .C..A..C.. G..C.....T ..CA.....C ..CG....A. ...G....C.T 1201                                                                    1250
GmEPSPS_Nat   CGAGGCATTG ATGTCAATAT GAACAAGATG CCAGATGTTG CCATGACACT
GmEPSPS_GM    A.G..A..A. ......... ...G...... ...T...... .......G...G..
```

Figure 3 (Continued)

```
              1251                                                      1300
GmEPSPS_Nat   TGCTGTTGTT GCACTATTTG CTAATGGTCC CACTGCTATA AGAGATGTGG
GmEPSPS_GM    C......... ..C..G..C. .A..C..A.. T..C..A... ..G.....C.

1301                                                      1350
GmEPSPS_Nat   CAAGTTGGAG AGTTAAAGAG ACTGAGAGGA TGATAGCAAT CTGCACAGAA
GmEPSPS_GM    .TTCA...C. T......G..A ..C...AC.. ......C.T.. T.....C..G 1351                                                      1400
GmEPSPS_Nat   CTCAGAAAGC TAGGAGCAAC AGTTGAAGAA GGTCCTGATT ACTGTGTGAT
GmEPSPS_GM    T.GC.T.... .G..T..... G..G...... ..A..A..C. T..C......

1401                                                      1450
GmEPSPS_Nat   TACTCCACCT GAGAAATTGA ATGTCACAGC TATAGACACA TATGATGACC
GmEPSPS_GM    A..A..T... ..A..GC.C. ....G..C.. .........T ......C..T.

1451                                                      1500
GmEPSPS_Nat   ACAGAATGGC CATGGCATTC TCTCTTGCTG CTTGTGGGGA TGTTCCAGTA
GmEPSPS_GM    .......... T......... .........A .....C..T.. C..G..G..T
```

Figure 3 (Continued)

```
              1501                                                          1550
GmEPSPS_Nat   ACCATCAAGG ATCCTGGTTG CACCAGGAAG ACATTCCTG  ACTACTTTGA
GmEPSPS_GM    ..G.......  .C..A..G..  T..T......  .....C..A.  .T........

1551                                       1578
GmEPSPS_Nat   AGTCCCTTGAG AGGTTAACAA AGCACTAA
GmEPSPS_GM    G..GT.G..A  ..A..G....  ......G.
```

Figure 3 (Continued)

```
                 1
BAR1_Nat ATGAGCCCAG AACGACGCCC GGCCGACATC CGCCGTGCCA CCGAGGCGGA
BAR1_ZM  ...TCG..T. .G..C..T.. T..T.....A A.A..C..T. .......A..
BAR1_AT  .......T.. ..A.GA.A.. ........T. .T..T ..GA.A.... ....A..T..
                                                              50

51
BAR1_Nat CATGCCGGGCG GTCTGCACCA TCGTCAACCA CTACATCGAG ACAAGCACGG
BAR1_ZM  .....T..T.. ........T. .T..G..T.. .......... .....TCT...
BAR1_AT  T.....T..T. ..T..T..A. ....A..... T..T...... ..CTCG..A..
                                                              100

101
BAR1_Nat TCAACTTCCG TACCGAGCCG CAGGAACCGC AGGACTGGAC GGACGACCTC
BAR1_ZM  .A........ ...C..T....T ........T .A........ .....T....T
BAR1_AT  .T..T..T.. ..C..T.... .......... .....G..A. .......T..G
                                                              150

151
BAR1_Nat GTCCGTCTGC GGGAGCGCTA TCCCTGGCTC GTCGCCGAGG TGGACGGCGA
BAR1_ZM  ..G.....CA .A....T... ....G.....G ..T..A.... ......T...
BAR1_AT  ..A...T.AA .A..A..T.. ........G. .....A .......T..T.. .....A..
                                                              200
```

Figure 4 (Continued)

```
              201
BAR1_Nat  GGTCGCCGGC ATCGCCTACG CGGGCCCCTG GAAGGCACGC AACGCCTACG
BAR1_ZM   A..G..T..G ..........  .T..A..G..  .....TA.A  .....A....
BAR1_AT   A......T..T  ..A..T....  .T..A..G..  ...A..T..T  .....T....

251                                                    300
BAR1_Nat  ACTGGACGGC CGAGTCGACC GTGTACGTCT CCCCCCGCCA CCAGCGGACG
BAR1_ZM   .T......T..  G....C..A  ..C......  .A..A.A..  T..AA.A..C
BAR1_AT   .......A..  A..A..C..T  .C.......A  G...T..T..  T..AA.A..C 301                                                    350
BAR1_Nat  GGACTGGGCT CCACGCTCTA CACCCACCTG CTGAAGTCCC TGGAGGCACA
BAR1_ZM   ..G..C....  .G..C.....  T..G..T..C  .C.....T  .A......G..
BAR1_AT   ...T.A..GA  G....T.G..  ...T..T..T  T.A.....A  ..........

351                                                    400
BAR1_Nat  GGGCTTCAAG AGCGTGGGTCG CTGTCATCGG GCTGCCCAAC GACCCGAGCG
BAR1_ZM   ......A  TCT..A..G.  .G..G....  CT....A...  ..T..C..T.
BAR1_AT   A.........  TCT..T..G.  .A..T..T..  AT....A...  ..T.....T.
```

Figure 4 (Continued)

```
         401
BAR1_Nat TGGCGCATGCA CGAGGGCGCTC GGATATGCCC CCCGCGGGCAT GCTGCGGGCG
BAR1_ZM  ..A..A..... ........A.. ..T..C..T. .TA.A..A.. ...CA.....
BAR1_AT  .T..A...... ........A.. .....T.... .A..A..T.. ...C..T..T 451                                                   500
BAR1_Nat GCCGGGCTTCA AGCACGGGGAA CTGGCATGAC GTGGGTTTCT GGCAGCTGGA
BAR1_ZM  ..T..A..... ........... T......C... ...T..C... ....A.....
BAR1_AT  .....A..... .A..T..A..  T......C... ..A......T ....A.....

501                                                   550
BAR1_Nat CTTCAGCCTG CCGGTACCGC CCCGTCCGGT CCTGCCCGTC ACCGAGATCT
BAR1_ZM  ....TCTT.. ..A..T..A. .T.....T.. G..A...... ......A...
BAR1_AT  ...TTCA..T ..C..T..C. .TA.A..T.. A..T..A..T ..T..A....

551
BAR1_Nat GA
BAR1_ZM  AG
BAR1_AT  AG
```

Figure 4 (Continued)

```
              1                                                              60
CTP2CP4NAT    ATGGCGCAAG TTAGCAGAAT CTGCAATGGT GTGCAGAACC CATCTCTTAT CTCCAATCTC
CTP2CP4_ZM    .........  .A..T....  .....C..C  ...T..C.A  .G..G..G.  .....C...
CTP2CP4_AT    .....C..G.  .A..T..G.  ...T..C.A  ..C..A...  .T..A..A.  A.G..C..G
CTP2CP4_GM    .....C....  .......C.  .....C...  ........T  ...A.A...  .....C..G 61                                                             120
CTP2CP4NAT    TCGAAATCCA GTCAACGCAA ATCTCCCTTA TCGGTTTCTC TGAAGACGCA GCAGCATCCA
CTP2CP4_ZM    AGC..G....  .C..G..G.  G..G..GC.C  ....CAGC.  .C......C  A......C.G
CTP2CP4_AT    ..A...AG.T  C....A.A.  G..G..GC.T  ..T..A.GT  .....A.T.  A......C.G
CTP2CP4_GM    ..C.....GT  CA.....T..  G..G..A...  ..T...AGCT  ......T..  ...A.....T 121                                                            180
CTP2CP4NAT    CGAGCTTATC CGATTTCGTC GTCGTGGGGA TTGAAGAAGA GTGGGATGAC GTTAATTGGC
CTP2CP4_ZM    A.G..A..C.  .T..CAGC..  A..C.....C  C..C......  .....C...  .C.G..C..
CTP2CP4_AT    A.G.......  .C..C..AAG  C..C....T  C.A....A.  .....A...  AC.G..C..T
CTP2CP4_GM    ..C..A....  .T..A..AAG  CAGT......  .........T  ....AT CG..T.....  C..G......T 181                                                            240
CTP2CP4NAT    TCTGAGCTTC GTCCTCTTAA GGTCATGTCT TCTGTTTCCA CGGCGTGCAT GCTTCACGGT
CP2CP4_ZM     AGC......G.  .G..A..C..  .....G....  .C.....G..C..A  .........  ...A.....
CTP2CP4_AT    AGC..A..A.  .A..G..G.  A.....A...  ...C...A..CAG..  .T......  .....T..A
CTP2CP4_GM    ..G..A...A  .G..AT.G.  ...G......  ......A..AGT.  .A..T....  .........
```

Figure 5 (Continued)

```
              241
CTP2CP4NAT    GCAAGCAGCC GGCCCCGCAAC CGCCCGCAAA TCCTCTGGCC TTTCCGGAAC CGTCCGCATT
CTP2CP4_ZM    .........G ..........  ....T..... C......... ....G..... G...A.G...
CTP2CP4_AT    ..TTCATCTA ....A..T.. ...A..G..G ..TAGC..G. .CAGT..C.. ...G......C
CTP2CP4_GM    ..TTCTTC.A ..A....... G..TA.A..G AGT.......T .G..T..... ..........
              301                                                              360
CTP2CP4NAT    CCCGGGCACA AGTCGATCTC CCACCGGTCC TTCATGTTCG GCGGTCTCGC GAGCGGGTGAA
CTP2CP4_ZM    ..G......T ...C..A... ........G. .......... ........T. .C........G
CTP2CP4_AT    .T.......T .AAGT..T.. A..A..AG.. .......... ..A..A..T.. T..T..A..G
CTP2CP4_GM    ..A..A.... .AAGC..TAG T......C..T .......... .T..G..G.. ATCT..A..G
              361                                                              420
CTP2CP4NAT    ACGGCGATCA CCGGCCTTCT GGAAGGCGAG GACGTCATCA ATACGGGCAA GGCCATGCAG
CTP2CP4_ZM    .......... ..G....G.. T...G..... .......... ...C..G... ..........
CTP2CP4_AT    .......... ..T..TT.G.. T..G.....A ..T..T.... .C..C..T.. ..G......A
CTP2CP4_GM    ..A..A.... .T..T..... .......A.. .......T.. .......... ..A..G....
              421                                                              480
CTP2CP4NAT    GCGATGGGCG CCCGGCATCCG TAAGGAAGGC GACACCTGGA TCATCGATGG CGTCGGCAAT
CTP2CP4_ZM    ..T....A.. .G..T..... C........T ......A... .T.C...... ...T..G...
CTP2CP4_AT    ..A......T ..A.A..... A..A..G... ...T..G... ..T..G.... ...C...T..T..T..
CTP2CP4_GM    ..T....... ....T..T.. C......... ...T...... ...T..T... ..A..C... A..T..G...
```

Figure 5 (Continued)

```
              481                                                        540
CTP2CP4NAT    GGCGGCCTCC TGGCGCCTGA GGCGCCGCTC GATTTCGGCA ATGCCGCCAC GGGCTGCCGC
CTP2CP4_ZM    .....T..G. .C..C..... ...C..T... .C........ ......G..G ........A.G
CTP2CP4_AT    ..A..AT.G. .C..T..C.. A.....A..T ..C..T..G. .C..A..T.. ...G......T
CTP2CP4_GM    ..T....T.A ..T..A..G. ...T..T... ..C..T.... .C..A..... A..G..TA.A 541                                                        600
CTP2CP4NAT    CTGACGATGG GCCTCGTCGG GGTCTACGAT TTCGACAGCA CCTTCATCGG CGACGCCTCG
CTP2CP4_ZM    ..C..T.... .A..G..... ...G......C ........T. .G........ A.........
CTP2CP4_AT    ..T..T.... ..A..G..A. C..G..T..C ..T...TCT. .......T.. T....GAGC.
CTP2CP4_GM    ..T..T.... .......G.. ...T...... T......... ......TTCA ...G..T...T 601                                                        660
CTP2CP4NAT    CTCACAAAGC GCCCGATGGG CCGCGTGTTG AACCCGCTGC GCGAAATGGG CGTGCAGGTG
CTP2CP4_ZM    .......... .....A.... ......TC.. ......T... ....G..... ....A.....C
CTP2CP4_AT    .....T..A. .A..A..... A.A...C... ..T..C...A ..G..G.... T..C.......
CTP2CP4_GM    .....T..A. ....A..... AA.A..CC.T .......T.A ..G..G.... ...A..A..T 661                                                        720
CTP2CP4NAT    AAATCGGAAG ACGGTGACCG TCTTCCCGTT ACCTTGCGCG GGCCGAAGAC GCCGACGCCG
CTP2CP4_ZM    .....C..G. .T..G..... .T.G......  .....GC... ....C..... ...T..C...
CTP2CP4_AT    .....T..G. .T.....T.. .....G.... ..TC....A. .C..C..... C..C.....A
CTP2CP4_GM    ..G..C..G. .......... ....A..... AT.G.....C .C..T..... A..C..C..T
```

Figure 5 (Continued)

```
              721
CTP2CP4NAT    ATCACCTACC GCGTGCCGAT GGCCTCCGCA CAGGTGAAGT CCGCCGTGCT GCTCGCCGGC
CTP2CP4_ZM    ..T....... .........A ....A....C .........C .A........ C.......A
CTP2CP4_AT    ....G..A.. .G..T..... ...G..A... ....C..... .A.G..A... C..G..G...
CTP2CP4_GM    ..T....A.. .G..T..A.. .G..T..T.. ..A....... ......A..T ......T..A 781                                                            840
CTP2CP4NAT    CTCAACACGC CCGGCATCAC GACGGTCATC GAGCCGATCA TGACGCGCGA TCATACGGAA
CTP2CP4_ZM    .G.....T.. .G........ C........G ....C..... ......CA.. ...C.....
CTP2CP4_AT    .......A.. .T..A..... A..C..G..T ..A.C..... ......TA.A ...C..C...G
CTP2CP4_GM    T.G.....A. .G..T..T.. T..C..G..T .......... ......T..T C..C..T..G 841                                                            900
CTP2CP4NAT    AAGATGCTGC AGGGCTTTGG CGCCAACCTT ACCGTCGAGA CGGATGCGGA CGGCGTGCGC
CTP2CP4_ZM    .........T .....G.... .........G ...G...... ......C.T. ......CA.G
CTP2CP4_AT    .........T .....T..C. ...T..T..A ....T..A.. .C..C..C.. ......A.G
CTP2CP4_GM    .........T ........T. ...T..T.C. ..T....C.. .A..C..... ....T..A.G 901                                                            960
CTP2CP4NAT    ACCATCCCGC TGGAAGGCCG CGGCAAGCTC ACCGGGCCAAG TCATCGACGT GCCGGGCGAC
CTP2CP4_ZM    .........T .G...A. G..T..A..G ..T....... ..T....A...
CTP2CP4_AT    .A....T. ...G...A A..T..A..G ..T....... ..T....T..A..T
CTP2CP4_GM    .......T. ...G...AA G..A..A... ..T....T... ......C..T..T
```

```
              961                                                                      1020
CTP2CP4NAT    CCGTCCTCGA CGGCCTTCCC GCTGGTTGCG GCCCTGCTTG TTCCGGGCTC CGACGTCACC
CTP2CP4_ZM    .....G..C. .......... ....T..... .G.....C.. .G....GAG  T......G...
CTP2CP4_AT    ..C..G..C. .A..G..T.. .C..C..A.T ..GT.....C .C..T..A.. T..T..G..G
CTP2CP4_GM    ..C...AGC. ....G..... A......... ..T..T..C. .A..A..... ...T..G..A 1021                                                                     1080
CTP2CP4NAT    ATCCTCAACG TGCTGATGAA CCCCACCCGC ACCGGCCTCA TCCTGACGCT GCAGGAAATG
CTP2CP4_ZM    .......G.. .C..C..... ....G...A.G ..........G .....C.... T......G...
CTP2CP4_AT    .......G.T .C..C..... T..A..TA.A .......... ....C..AT. .......G...
CTP2CP4_GM    .......T.A .C..C..... T..T..TA.A .....AT.G. .A..T..AT. ...........

1081                                                                     1140
CTP2CP4NAT    GGGCGCCGACA TCGAAGTCAT CAACCCGCGC CTTGCCGGCG GCGAAGACGT GGCGGACCTG
CTP2CP4_ZM    ..A....... ...G..G... .......... .G..A..... .......... T......T...
CTP2CP4_AT    ..T..T.... ...G..T... ...T..TA.G T.G..A..T. .A..G..T.. ...C..T...
CTP2CP4_GM    ..T..T.... .T..T..... ...T..TA.A .A.....A.. .T..G..... A..T..TT..

1141                                                                     1200
CTP2CP4NAT    CGGCGTTCGCT CCTCCACGCT GAAGGGCGTC ACGGTGCCGG AAGACCGGCGC GCCTTCGATG
CTP2CP4_ZM    .....G.... ...T..C... ......G... .....C.... .....T.... ..G..C....
CTP2CP4_AT    .....G..T. .TAGT..A.. C..A.....G ..C..C..T. .G..T..... T..A..C...
CTP2CP4_GM    ..G..GA.G. .T..T..AT. ...A..T..T ..A..T..T ....TA.G.. A......A..
```

```
           1201                                                      1260
CTP2CP4NAT ATCGACGAAT ATCCGATTCT CGCTGTCGCC GCCGCCTTCG CGGAAGGGGC GACCGTGATG
CTP2CP4_ZM ..A.....G. ....T..... G..C...... ..T.G..... .C........ C..G..C...
CTP2CP4_AT ........G. ....C..... ...C.T..T. ...T.G.T.. .C..G..C.. A..T..A...
CTP2CP4_GM ..T.....G. ....A..... T..C.....G .....T.... .T..G..C.. ..........

1261                                                      1320
CTP2CP4NAT AACGGTCTGG AAGAACTCCG CGTCAAGGAA AGCGACCGCC TCTCGGCCGT CGCCAATGGC
CTP2CP4_ZM .......T.. .G........ .....G.... TCG.T..... .G.....G.. G.........
CTP2CP4_AT ...C..T... .C........ G..GT.GA.. ...T...A.G .G..C..G.. G.G.......
CTP2CP4_GM ..T..A..A. .G..GT.GA. A..G...... TC....A.AT .GAGC...A. ..T..C...A 1321                                                      1380
CTP2CP4NAT CTCAAGCTCA ATGGCGTGGA TTGCGATGAG GGCGAGACGT CGCTCGTCGT GCGTGGCCGC
CTP2CP4_ZM ..G....... .....C..T. C........ .....T.... ..A..G.... C........G
CTP2CP4_AT .G.....A.. .C........ C....C..A .....T..A. ...C.T.A.. C....T....
CTP2CP4_GM ..T..A.... ..........       ....T..... ......TA GCT.G..A.. C......G..A 1381                                                      1440
CTP2CP4NAT CCTGACGGCA AGGGGCTCGG CAACGCCCTG GGCGCCGCCG TCGCCACCCA TCTCGATCAC
CTP2CP4_ZM ....T..... .....C.... ......AGT ..A..G.... ........ .....G.... C........T
CTP2CP4_AT ..A.....G. ....T.G.. G.T.T.... ..A..T.T.. .A..T..... .G..G.G.. C..T.....T
CTP2CP4_GM ..A.....A. ....TT.G.. ..........   ....T..... .....T.T... .T..A..T.. CT.G.....T
```

Figure 5 (Continued)

```
             1441
CTP2CP4NAT   CGCATCGCCA TGAGCTTCCT CGTCATGGGC CTCGTGTCGG AAAACCCTGT CACGGTGGAC
CTP2CP4_ZM   .........G. ..TC....T. G..G.....T ....C..A.. .G.....G.. .G..C..C..T
CTP2CP4_AT   A.A........ ..TCA..T.. G..G.....A ..T..C..C. .G.T..G.. G..C..T...
CTP2CP4_GM   ..G..A..G. ........T..T.. G..G.....T .....AAGC. .G.T..... G..A..C...
                                                                           1500

1501
CTP2CP4NAT   GATGCCACGA TGATCGGCCAC GAGCTTCCCG GAGTTCATGG ACCTGATGGC CGGGCTGGGC
CTP2CP4_ZM   ..C....... ....A..G.. .......... .A........ .T........ G..C..C..G
CTP2CP4_AT   .....T..C. .......... CTC...T..T ....T..... ....C..... A..CT....G
CTP2CP4_GM   .....A..T. .......... TTC.......T ....T..... .TT.A..... A..A..A..T
                                                                           1560

1561
CTP2CP4NAT   GCGAAGATCG AACTCTCCGA TACGAAGGCT GCCTGA
CTP4CP4_ZM   ..C....... ......G..T. .........C ..T...
CTP2CP4_AT   ..C....... .G..G..T.. ........C. ..T...
CTP2CP4_GM   ..A........ ........T..  ...C..A..G .....A.
                                              1596
```

Figure 5 (Continued)

```
                        SEQUENCE LISTING

<160> NUMBER OF SEQ ID NOS: 38

<210> SEQ ID NO 1
<211> LENGTH: 515
<212> TYPE: PRT
<213> ORGANISM: Oryza sativa

<400> SEQUENCE: 1

Met Ala Ala Thr Met Ala Ser Asn Ala Ala Ala Ala Ala Val Ser
1               5                   10                  15

Leu Asp Gln Ala Val Ala Ser Ala Ala Phe Ser Ser Arg Lys Gln
                20                  25                  30

Leu Arg Leu Pro Ala Ala Ala Arg Gly Gly Met Arg Val Arg Val Arg
                35                  40                  45

Ala Arg Gly Arg Arg Glu Ala Val Val Ala Ser Ala Ser Ser Ser
    50                  55                  60

Ser Val Ala Ala Pro Ala Ala Lys Ala Glu Glu Ile Val Leu Gln Pro
65                  70                  75                  80

Ile Arg Glu Ile Ser Gly Ala Val Gln Leu Pro Gly Ser Lys Ser Leu
                85                  90                  95

Ser Asn Arg Ile Leu Leu Leu Ser Ala Leu Ser Glu Gly Thr Thr Val
                100                 105                 110

Val Asp Asn Leu Leu Asn Ser Glu Asp Val His Tyr Met Leu Glu Ala
                115                 120                 125

Leu Lys Ala Leu Gly Leu Ser Val Glu Ala Asp Lys Val Ala Lys Arg
    130                 135                 140

Ala Val Val Val Gly Cys Gly Gly Lys Phe Pro Val Glu Lys Asp Ala
145                 150                 155                 160

Lys Glu Glu Val Gln Leu Phe Leu Gly Asn Ala Gly Ile Ala Met Arg
                165                 170                 175

Ser Leu Thr Ala Ala Val Thr Ala Ala Gly Gly Asn Ala Thr Tyr Val
                180                 185                 190

Leu Asp Gly Val Pro Arg Met Arg Glu Arg Pro Ile Gly Asp Leu Val
                195                 200                 205

Val Gly Leu Lys Gln Leu Gly Ala Asp Val Asp Cys Phe Leu Gly Thr
    210                 215                 220

Glu Cys Pro Pro Val Arg Val Lys Gly Ile Gly Gly Leu Pro Gly Gly
225                 230                 235                 240

Lys Val Lys Leu Ser Gly Ser Ile Ser Ser Gln Tyr Leu Ser Ala Leu
                245                 250                 255

Leu Met Ala Ala Pro Leu Ala Leu Gly Asp Val Glu Ile Glu Ile Ile
                260                 265                 270
```

Asp Lys Leu Ile Ser Ile Pro Tyr Val Glu Met Thr Leu Arg Leu Met
    275                 280                 285

Glu Arg Phe Gly Val Lys Ala Glu His Ser Asp Ser Trp Asp Arg Phe
    290                 295                 300

Tyr Ile Lys Gly Gln Lys Tyr Lys Ser Pro Gly Asn Ala Tyr Val
305                 310                 315                 320

Glu Gly Asp Ala Ser Ala Ser Tyr Phe Leu Ala Gly Ala Ala Ile
                325                 330                 335

Thr Gly Gly Thr Val Thr Val Gln Gly Cys Gly Thr Thr Ser Leu Gln
                340                 345                 350

Gly Asp Val Lys Phe Ala Glu Val Leu Glu Met Met Gly Ala Lys Val
                355                 360                 365

Thr Trp Thr Asp Thr Ser Val Thr Val Thr Gly Pro Pro Arg Glu Pro
    370                 375                 380

Tyr Gly Lys Lys His Leu Lys Ala Val Asp Val Asn Met Asn Lys Met
385                 390                 395                 400

Pro Asp Val Ala Met Thr Leu Ala Val Ala Leu Phe Ala Asp Gly
                405                 410                 415

Pro Thr Ala Ile Arg Asp Val Ala Ser Trp Arg Val Lys Glu Thr Glu
                420                 425                 430

Arg Met Val Ala Ile Arg Thr Glu Leu Thr Lys Leu Gly Ala Ser Val
    435                 440                 445

Glu Glu Gly Pro Asp Tyr Cys Ile Ile Thr Pro Pro Glu Lys Leu Asn
    450                 455                 460

Ile Thr Ala Ile Asp Thr Tyr Asp Asp His Arg Met Ala Met Ala Phe
465                 470                 475                 480

Ser Leu Ala Ala Cys Ala Asp Val Pro Val Thr Ile Arg Asp Pro Gly
                485                 490                 495

Cys Thr Arg Lys Thr Phe Pro Asn Tyr Phe Asp Val Leu Ser Thr Phe
                500                 505                 510

Val Arg Asn
    515

<210> SEQ ID NO 2
<211> LENGTH: 1548
<212> TYPE: DNA
<213> ORGANISM: Oryza sativa

<400> SEQUENCE: 2
atggcggcga ccatggcgtc caacgccgcg gctgcggcgg cggtgtccct ggaccaggcc      60
gtggcggcgt cggcggcgtt ctcgtcgcgg aagcagctgc ggctgcccgc cgcggcgcgc     120
ggggggatgc gggtgcgggt gcgggcgcgg ggcggcggg aggcggtggt ggtggcgtcc      180
gcgtcgtcgt cgtcggtggc agcgccggcg gcgaaggcgg aggagatcgt gctccagccc     240
atcagggaga tctccggggc ggttcagctg ccagggtcca gtcgctctc caacaggatc      300 ctcctcctct ccgccctctc cgagggcaca acagtggtgg acaacttgct gaacagtgag     360
gatgttcact acatgcttga ggccctgaaa gccctcgggc tctctgtgga agcagataaa     420
gttgcaaaaa gagctgtagt cgttggctgt ggtggcaagt ttcctgttga aaggatgcg      480 aaagaggaag tgcaactctt cttggggaac gctggaatcg caatgcgatc cttgacagca     540
gccgtgactg ctgctggtgg aaatgcaact tatgtgcttg atggagtgcc acgaatgagg     600
gagagaccga ttggtgactt ggttgtcggg ttgaacaac ttggtgcgga tgtcgactgt     660

```
ttccttggca ctgaatgccc acctgttcgt gtcaagggaa ttggaggact tcctggtggc   720
aaggttaagc tctctggttc catcagcagt cagtacttga gtgccttgct gatggctgct   780
cctttggccc ttggggatgt ggagatcgaa atcattgaca aactaatctc cattccttac   840
gttgaaatga cattgagatt gatggagcgt tttggtgtga aggcagagca ttctgatagt   900
tgggacagat tctatattaa gggagggcag aagtacaaat ctcctggaaa tgcctatgtt   960
gaaggtgatg cctcaagcgc gagctatttc ttggctggtg ctgcaatcac tggaggcact  1020
gtgacagttc aaggttgtgg tacgaccagt ttgcagggtg atgtcaaatt tgctgaggta  1080
cttgagatga tgggagcaaa ggttacatgg actgacacca gtgtaaccgt aactggtcca  1140
ccacgtgagc cttatgggaa gaaacacctg aaagctgttg atgtcaacat gaacaaaatg  1200
cctgatgttg ccatgaccct tgccgttgtt gcactcttcg ctgatggtcc aactgctatc  1260
agagatgtgg cttcctggag agtaaaggaa accgaaagga tggttgcaat tcggaccgag  1320
ctaacaaagc tggagcatc ggttgaagaa ggtcctgact actgcatcat caccccaccg  1380
gagaagctga acatcacggc aatcgacacc tacgatgatc acaggatggc catggccttc  1440
tccctcgctg cctgcgccga cgtgcccgtg acgatcaggg accctggttg cacccgcaag  1500 accttccccca actacttcga cgttctaagc actttcgtca ggaactga              1548
```

<210> SEQ ID NO 3
<211> LENGTH: 1548
<212> TYPE: DNA
<213> ORGANISM: Oryza sativa

<400> SEQUENCE: 3

```
atggctgcaa ctatggctag taacgcagcg gctgccgctg ccgtttcctt agaccaagca    60
gtagcagcga gcgctgcatt ctcatcacgt aagcaactac ggctaccagc agccgctaga   120
ggcggcatga gagttagagt gagggctaga ggtaggcggg aggctgtagt cgtagcctcc   180
gcttctagca gttcggtggc tgcgccggct gctaaggcag aggagattgt tttacaacct   240
attagggaaa tatcgggggc cgtacaatta cctggaagca agagcctttc caacaggatt   300
ctgttgcttt cagctctctc ggagggaaca acagttgtgg ataatctgtt gaatagtgag   360
gatgtgcact atatgctaga ggctctcaag gctctagggc tttctgtaga agcggataaa   420
gtagcaaaac gcgcagtggt tgtaggttgt ggtgggaagt tcccagttga aaaggatgct   480
aaggaagaag tacagctctt tctcgggaat gccgggatcg ccatgcggag tttgactgct   540
gcggtcacag ccgctggagg caacgcaaca tacgtcctag atggggtgcc gagaatgcgt   600
gagcgtccta ttggtgatct tgtcgtaggt ctcaagcaac tcggcgctga cgtagattgt   660
ttcctgggta ctgagtgtcc gccagtcaga gttaaaggaa tcggtgggct gccgggcgga   720
aaggtcaagc tgtcgggcag tatttcgagt cagtatcttt ctgctctcct gatggctgcg   780
ccattagctt gggagatgt tgagatcgag atcattgata aacttatatc tatcccgtat   840
gtcgagatga ctttaagact tatggaacgg tttggggtta aggccgagca tagcgacagt   900
tgggatcgtt tctacataaa gggaggccag aagtataagt ctcctgggaa tgcttatgta   960 gaagggatg cttcatctgc gtcttacttc cttgcgggag cggctataac tggaggaaca  1020
gtcacagttc agggctgcgg tacaacaagt ttgcaaggtg acgtgaagtt tgccgaggta  1080
cttgaaatga tgggtgccaa agtaacgtgg acagacacat cggtgacagt tactggtcct  1140
ccacgagaac cttacggcaa aaagcatctt aaggccgtgg atgttaatat gaataagatg  1200
cctgacgttg ctatgacact tgccgttgtt gcccttttg cagacggccc aacggcgata  1260
```

```
cgcgatgttg catcatggcg cgtcaaggaa acggagagga tggtggctat tcgaactgaa    1320
ctcaccaaac ttggtgcctc tgtagaggag ggccctgatt actgtatcat tacaccccct    1380
gagaaactta acatcactgc tattgataca tacgacgatc atagaatggc tatggctttc    1440
tcactggccg cttgtgcaga tgttcctgtc acaatcagag atcctggctg tactagaaag    1500
acgttcccga actactttga tgttctttca acattcgtcc gcaattga                 1548
```

<210> SEQ ID NO 4
<211> LENGTH: 1548
<212> TYPE: DNA
<213> ORGANISM: Oryza sativa

<400> SEQUENCE: 4

```
atggctgcaa ctatggctag taacgcagcg gctgccgctg ccgtttcctt agaccaagca     60
gtagcagcga gcgctgcatt ctcatcacgt aagcaactac ggctaccagc agccgctaga    120
ggcggcatga gagttagagt gagggctaga ggtaggcggg aggctgtagt cgtagcctcc    180
gcttctagca gttcggtggc tgcgccggct gctaaggcag aggagattgt tttacaacct    240
attagggaaa tatcggggc cgtacaatta cctggaagca agagcctttc caacaggatt    300
ctgttgcttt cagctctctc ggagggaaca acagttgtgg ataatctgtt gaatagtgag    360
gatgtgcact atatgctaga ggctctcaag gctctagggc tttctgtaga agcggataaa    420
gtagcaaaac gcgcagtggt tgtaggttgt ggtgggaagt tcccagttga aaaggatgct    480
aaggaagaag tacagctctt tctcgggaat gccgggatcg ccatgcggag tttgactgct    540
gcggtcacag ccgctggagg caacgcaaca tacgtcctag atggggtgcc gagaatgcgt    600
gagcgtccta ttggtgatct tgtcgtaggt ctcaagcaac tcggcgctga cgtagattgt    660
ttcctgggta ctgagtgtcc gccagtcaga gttaaaggaa tcggtgggct gccgggcgga    720
aaggtcaagc tgtcgggcag tatttcgagt cagtatcttt ctgctctcct gatggctgcg    780
ccattagctt tgggagatgt tgagatcgag atcattgata aacttatatc tatcccgtat    840
gtcgagatga ctttaagact tatggaacgg tttgggggtta aggccgagca tagcgacagt    900
tgggatcgtt tctacataaa gggaggccag aagtataagt ctcctgggaa tgcttatgta    960 gaagggggatg cttcatctgc gtcttacttc cttgcgggag cggctataac tggaggaaca   1020
gtcacagttc agggctgcgg tacaacaagt ttgcaaggtg acgtgaagtt tgccgaggta   1080
cttgaaatga tgggtgccaa agtaacgtgg acagacacat cggtgacagt tactggtcct   1140
ccacgagaac cttacggcaa aaagcatctt aaggccgtgg atgttaatat gaataagatg   1200
cctgacgttg ctatgacact tgccgttgtt gcccttttg cagacggccc aacggcgata   1260
cgcgatgttg catcatggcg cgtcaaggaa acggagagga tggtggctat tcgaactgaa   1320
ctcaccaaac ttggtgcctc tgtagaggag ggccctgatt actgtatcat tacaccccct   1380
gagaaactta acatcactgc tattgataca tacgacgatc atagaatggc tatggctttc   1440
tcactggccg cttgtgcaga tgttcctgtc acaatcagag atcctggctg tactagaaag   1500
acgttcccga actactttga tgttctttca acattcgtcc gcaattga                1548
```

<210> SEQ ID NO 5
<211> LENGTH: 525
<212> TYPE: PRT
<213> ORGANISM: Glycine max

<400> SEQUENCE: 5

```
Met Ala Gln Val Ser Arg Val His Asn Leu Ala Gln Ser Thr Gln Ile
1               5                   10                  15

Phe Gly His Ser Ser Asn Ser Asn Lys Leu Lys Ser Val Asn Ser Val
                20                  25                  30

Ser Leu Arg Pro Arg Leu Trp Gly Ala Ser Lys Ser Arg Ile Pro Met
            35                  40                  45

His Lys Asn Gly Ser Phe Met Gly Asn Phe Asn Val Gly Lys Gly Asn
        50                  55                  60

Ser Gly Val Phe Lys Val Ser Ala Ser Val Ala Ala Glu Lys Pro
65                  70                  75                  80

Ser Thr Ser Pro Glu Ile Val Leu Glu Pro Ile Lys Asp Phe Ser Gly
                85                  90                  95

Thr Ile Thr Leu Pro Gly Ser Lys Ser Leu Ser Asn Arg Ile Leu Leu
                100                 105                 110

Leu Ala Ala Leu Ser Glu Gly Thr Thr Val Val Asp Asn Leu Leu Tyr
            115                 120                 125

Ser Glu Asp Ile His Tyr Met Leu Gly Ala Leu Arg Thr Leu Gly Leu
130                 135                 140

Arg Val Glu Asp Asp Lys Thr Thr Lys Gln Ala Ile Val Glu Gly Cys
145                 150                 155                 160

Gly Gly Leu Phe Pro Thr Ser Lys Glu Ser Lys Asp Glu Ile Asn Leu
                165                 170                 175

Phe Leu Gly Asn Ala Gly Ile Ala Met Lys Ser Leu Thr Ala Ala Val
            180                 185                 190

Val Ala Ala Gly Gly Asn Ala Ser Tyr Val Leu Asp Gly Val Pro Arg
            195                 200                 205

Met Arg Glu Arg Pro Ile Gly Asp Leu Val Ala Gly Leu Lys Gln Leu
210                 215                 220

Gly Ala Asp Val Asp Cys Phe Leu Gly Thr Asn Cys Pro Pro Val Arg
225                 230                 235                 240

Val Asn Gly Lys Gly Gly Leu Pro Gly Gly Lys Val Lys Leu Ser Gly
                245                 250                 255

Ser Val Ser Ser Gln Tyr Leu Thr Ala Leu Leu Met Ala Ala Pro Leu
            260                 265                 270

Ala Leu Gly Asp Val Glu Ile Glu Ile Val Asp Lys Leu Ile Ser Val
            275                 280                 285

Pro Tyr Val Glu Met Thr Leu Lys Leu Met Glu Arg Phe Gly Val Ser
        290                 295                 300

Val Glu His Ser Gly Asn Trp Asp Arg Phe Leu Val His Gly Gly Gln
305                 310                 315                 320

Lys Tyr Lys Ser Pro Gly Asn Ala Phe Val Glu Gly Asp Ala Ser Ser
                325                 330                 335

Ala Ser Tyr Leu Leu Ala Gly Ala Ala Ile Thr Gly Gly Thr Ile Thr
            340                 345                 350

Val Asn Gly Cys Gly Thr Ser Ser Leu Gln Gly Asp Val Lys Phe Ala
            355                 360                 365

Glu Val Leu Glu Lys Met Gly Ala Lys Val Thr Trp Ser Glu Asn Ser
370                 375                 380

Val Thr Val Ser Gly Pro Pro Arg Asp Phe Ser Gly Arg Lys Val Leu
385                 390                 395                 400

Arg Gly Ile Asp Val Asn Met Asn Lys Met Pro Asp Val Ala Met Thr
            405                 410                 415

Leu Ala Val Val Ala Leu Phe Ala Asn Gly Pro Thr Ala Ile Arg Asp
```

```
                420               425               430
Val Ala Ser Trp Arg Val Lys Glu Thr Glu Arg Met Ile Ala Ile Cys
            435               440               445

Thr Glu Leu Arg Lys Leu Gly Ala Thr Val Glu Gly Pro Asp Tyr
        450               455               460

Cys Val Ile Thr Pro Glu Lys Leu Asn Val Thr Ala Ile Asp Thr
465               470               475               480

Tyr Asp Asp His Arg Met Ala Met Ala Phe Ser Leu Ala Ala Cys Gly
                485               490               495

Asp Val Pro Val Thr Ile Lys Asp Pro Gly Cys Thr Arg Lys Thr Phe
            500               505               510

Pro Asp Tyr Phe Glu Val Leu Glu Arg Leu Thr Lys His
        515               520               525
```

<210> SEQ ID NO 6
<211> LENGTH: 1578
<212> TYPE: DNA
<213> ORGANISM: Glycine max

<400> SEQUENCE: 6

```
atggcccaag tgagcagagt gcacaatctt gctcaaagca ctcaaatttt tggccattct      60
tccaactcca acaaactcaa atcggtgaat tcggtttcat tgaggccacg cctttggggg     120
gcctcaaaat ctcgcatccc gatgcataaa atgaagcttt atgggaaatt ttaatgtg       180
gggaagggaa attccggcgt gtttaaggtt tctgcatcgg tcgccgccgc agagaagccg     240
tcaacgtcgc cggagatcgt gttggaaccc atcaaagact tctcgggtac catcacattg     300
ccagggtcca gtctctgtc caatcgaatt ttgcttcttg ctgctctctc tgagggaaca     360
actgttgtag acaacttgtt gtatagtgag gatattcatt acatgcttgg tgcattaagg     420
acccttggac tgcgtgtgga agatgacaaa acaaccaaac aagcaattgt tgaaggctgt     480
gggggattgt ttcccactag taaggaatct aaagatgaaa tcaatttatt ccttggaaat     540
gctggtatcg caatgaagtc cttgacagca gctgtggttg ctgcaggtgg aaatgcaagc     600
tacgtacttg atggggtgcc ccgaatgaga gagaggccaa ttggggattt ggttgctggt     660
cttaagcaac ttggtgcaga tgttgattgc tttcttggca caaactgtcc acctgttcgt     720
gtaaatggga agggaggact tcctggcgga aaggtgaaac tgtctggatc agttagcagt     780
caatacttga ctgctttgct tatggcagct cctttagctc ttggtgatgt ggaaattgag     840
attgttgata aactgatttc tgttccatat gttgaaatga ctctgaagtt gatggagcgt     900
tttggagttt ctgtggaaca cagtggtaat tgggataggt tcttggtcca tggaggtcaa     960
aagtacaagt ctcctggcaa tgcttttgtt gaaggtgatg cttcaagtgc cagttattta    1020
ctagctggtg cagcaattac tggtgggact atcactgtta atggctgtgg cacaagcagt    1080
ttacagggag atgtaaaatt tgctgaagtt cttgaaaaga tgggagctaa ggttacatgg    1140
tcagagaaca gtgtcactgt ttctggacca ccacgagatt ttctggtcg aaaagtcttg    1200
cgaggcattg atgtcaatat gaacaagatg ccagatgttg ccatgacact tgctgttgtt    1260
gcactatttg ctaatggtcc cactgctata agagatgtgg caagttggag agttaaagag    1320
actgagagga tgatagcaat ctgcacagaa ctcagaaagc taggagcaac agttgaagaa    1380
ggtcctgatt actgtgtgat tactccacct gagaaattga atgtcacagc tatagacaca    1440
tatgatgacc acagaatggc catggcattc tctcttgctg cttgtgggga tgttccagta    1500
accatcaagg atcctggttg caccaggaag acatttcctg actactttga agtccttgag    1560
```

```
aggttaacaa agcactaa                                                   1578
```

<210> SEQ ID NO 7
<211> LENGTH: 1578
<212> TYPE: DNA
<213> ORGANISM: Glycine max

<400> SEQUENCE: 7

```
atggctcagg tctctcgcgt tcataatctc gctcagagta cccagatatt cggacattcc      60
agtaactcaa acaaactaaa gtctgtgaat agtgtatcac ttcggcctcg gctgtgggga     120
gcaagtaaga gccgtatccc tatgcacaag aacggttcgt tcatggggaa ctttaacgtc     180
ggcaaaggaa actcaggtgt cttcaaagta agcgccagcg tagctgcggc tgagaagccc     240
agtacttctc ctgaaattgt tcttgaaccg ataaaggatt tctcaggtac gattacacta     300
cctggatcaa agagtctctc taatagaatt ttgttgctcg cagctctgtc cgaaggaacc     360
actgtagtcg ataacctcct ttatagcgaa gatatacatt atatgttggg ggcgctcaga     420
actcttgggc taagagttga ggacgataag actactaaac aagctatcgt cgaaggttgt     480
ggcgggttgt tccctacttc taagaaagt aaagatgaga taaacttgtt tcttggcaac     540
gcaggaatcg caatgaagag cctcaccgct gctgtcgttg cggcgggtgg taacgctagt     600
tacgtcttag acggcgtgcc tagaatgcga gaaagaccta tcgtgatctc agtggctggc     660
ctaaaacagc ttggagcaga cgtcgattgt ttcttgggca caaattgccc gcccgtgaga     720
gtgaacggga agggaggctt gccaggcggt aaggttaaac tatccggatc ggtctcgtca     780
cagtacctaa ctgcattgct catggccgcc ccgctcgctt tggggacgt ggagattgaa      840
atcgtcgata agttgattag cgtgccttat gtggaaatga ccctcaaatt gatggagagg     900
ttcggagttt cggtagaaca ctccgggaat tgggatcggt ttcttgtaca cggagggcaa     960
aagtacaaaa gcccaggcaa tgccttcgtc aaggggacg cttcgagcgc ttcctatctc    1020
ctcgctggcg cagccataac cggtggcacc ataaccgtga acggctgcgg cacctcatcc    1080
cttcaaggtg atgtaaagtt cgctgaggtc ttggagaaaa tgggcgcaaa ggtcacatgg    1140
tctgagaaca gcgtaaccgt gtccggacct cccagagact ttcgtggtag aaaggtcctt    1200
agggggaatag atgtgaatat gaataagatg ccagatgtgg ctatgacgct cgctgttgtc    1260
gccctgttcg caaacggacc taccgcaata agggatgtcg cttcatggcg tgttaaggaa    1320
accgaacgga tgatcgctat ttgcaccgag ttgcgtaagc tgggtgcaac ggtggaagaa    1380
ggaccagact attgcgtgat aacacctcct gaaaagctca atgtgaccgc tattgacact    1440
tatgacgatc acagaatggc tatggcattc tcacttgctg cttgcggtga cgtgccggtt    1500
acgatcaagg acccagggtg tactaggaag acattcccag attactttga ggtgttggaa    1560
agattgacaa agcactga                                                   1578
```

<210> SEQ ID NO 8
<211> LENGTH: 506
<212> TYPE: PRT
<213> ORGANISM: Zea mays

<400> SEQUENCE: 8

```
Met Ala Ala Met Ala Thr Lys Ala Ala Ala Gly Thr Val Ser Leu Asp
1               5                   10                  15

Leu Ala Ala Pro Ser Arg Arg His His Arg Pro Ser Ser Ala Arg Pro
            20                  25                  30
```

```
Pro Phe Arg Pro Ala Val Arg Gly Leu Arg Ala Pro Gly Arg Arg Val
         35                  40                  45

Ile Ala Ala Pro Pro Ala Ala Ala Ala Ala Ala Val Gln Ala Gly
 50                  55                  60

Ala Glu Glu Ile Val Leu Gln Pro Ile Lys Glu Ile Ser Gly Thr Val
 65                  70                  75                  80

Lys Leu Pro Gly Ser Lys Ser Leu Ser Asn Arg Ile Leu Leu Leu Ala
                 85                  90                  95

Ala Leu Ser Glu Gly Thr Thr Val Val Asp Asn Leu Leu Asn Ser Glu
             100                 105                 110

Asp Val His Tyr Met Leu Gly Ala Leu Arg Thr Leu Gly Leu Ser Val
         115                 120                 125

Glu Ala Asp Lys Ala Ala Lys Arg Ala Val Val Gly Cys Gly Gly
     130                 135                 140

Lys Phe Pro Val Glu Asp Ala Lys Glu Glu Val Gln Leu Phe Leu Gly
145                 150                 155                 160

Asn Ala Gly Ile Ala Met Arg Ser Leu Thr Ala Ala Val Thr Ala Ala
                 165                 170                 175

Gly Gly Asn Ala Thr Tyr Val Leu Asp Gly Val Pro Arg Met Arg Glu
             180                 185                 190

Arg Pro Ile Gly Asp Leu Val Val Gly Leu Lys Gln Leu Gly Ala Asp
         195                 200                 205

Val Asp Cys Phe Leu Gly Thr Asp Cys Pro Pro Val Arg Val Asn Gly
     210                 215                 220

Ile Gly Gly Leu Pro Gly Gly Lys Val Lys Leu Ser Gly Ser Ile Ser
225                 230                 235                 240

Ser Gln Tyr Leu Ser Ala Leu Leu Met Ala Ala Pro Leu Ala Leu Gly
                 245                 250                 255

Asp Val Glu Ile Glu Ile Ile Asp Lys Leu Ile Ser Ile Pro Tyr Val
             260                 265                 270

Glu Met Thr Leu Arg Leu Met Glu Arg Phe Gly Val Lys Ala Glu His
         275                 280                 285

Ser Asp Ser Trp Asp Arg Phe Tyr Ile Lys Gly Gly Gln Lys Tyr Lys
     290                 295                 300

Ser Pro Lys Asn Ala Tyr Val Glu Gly Asp Ala Ser Ser Ala Ser Tyr
305                 310                 315                 320

Phe Leu Ala Gly Ala Ala Ile Thr Gly Gly Thr Val Thr Val Glu Gly
                 325                 330                 335

Cys Gly Thr Thr Ser Leu Gln Gly Asp Val Lys Phe Ala Glu Val Leu
             340                 345                 350

Glu Met Met Gly Ala Lys Val Thr Trp Thr Glu Thr Ser Val Thr Val
         355                 360                 365

Thr Gly Pro Pro Arg Glu Pro Phe Gly Arg Lys His Leu Lys Ala Ile
     370                 375                 380

Asp Val Asn Met Asn Lys Met Pro Asp Val Ala Met Thr Leu Ala Val
385                 390                 395                 400

Val Ala Leu Phe Ala Asp Gly Pro Thr Ala Ile Arg Asp Val Ala Ser
                 405                 410                 415

Trp Arg Val Lys Glu Thr Glu Arg Met Val Ala Ile Arg Thr Glu Leu
             420                 425                 430

Thr Lys Leu Gly Ala Ser Val Glu Glu Gly Pro Asp Tyr Cys Ile Ile
         435                 440                 445

Thr Pro Pro Glu Lys Leu Asn Val Thr Ala Ile Asp Thr Tyr Asp Asp
```

```
            450             455             460
His Arg Met Ala Met Ala Phe Ser Leu Ala Ala Cys Ala Glu Val Pro
465                 470             475                 480

Val Thr Ile Arg Asp Pro Gly Cys Thr Arg Lys Thr Phe Pro Asp Tyr
                485             490             495

Phe Asp Val Leu Ser Thr Phe Val Lys Asn
            500             505

<210> SEQ ID NO 9
<211> LENGTH: 1521
<212> TYPE: DNA
<213> ORGANISM: Zea mays

<400> SEQUENCE: 9
```

| | | | | | |
|---|---|---|---|---|---|
| atggcggcca | tggcgaccaa | ggccgccgcg | ggcaccgtgt | cgctggacct | cgccgcgccg | 60 |
| tcgcgccgcc | accaccgccc | gagctcggcg | cgcccgccct | tccgccccgc | cgtccgcggg | 120 |
| ctgcgggcgc | ctgggcgccg | cgtgatcgcc | gcgccgccgg | cggcggcagc | ggcggcggcg | 180 |
| gtgcaggcgg | gtgccgagga | gatcgtgctg | cagcccatca | aggagatctc | cggcaccgtc | 240 |
| aagctgccgg | ggtccaagtc | gctttccaac | cggatcctcc | tactcgccgc | cctgtccgag | 300 |
| gggacaacag | tggttgataa | cctgctgaac | agtgaggatg | tccactacat | gctcggggcc | 360 |
| ttgaggactc | ttggtctctc | tgtcgaagcg | gacaaagctg | ccaaaagagc | tgtagttgtt | 420 |
| ggctgtggtg | aaagttccc | agttgaggat | gctaaagagg | aagtgcagct | cttcttgggg | 480 |
| aatgctggaa | tcgcaatgcg | gtccttgaca | gcagctgtta | ctgctgctgg | tggaaatgca | 540 |
| acttacgtgc | ttgatggagt | accaagaatg | agggagagac | ccattggcga | cttggttgtc | 600 |
| ggattgaagc | agcttggtgc | agatgttgat | tgtttccttg | gcactgactg | cccacctgtt | 660 |
| cgtgtcaatg | gaatcggagg | gctacctggt | ggcaaggtca | agctgtctgg | ctccatcagc | 720 |
| agtcagtact | tgagtgcctt | gctgatggct | gctccttttgg | ctcttgggga | tgtggagatt | 780 |
| gaaatcattg | ataaattaat | ctccattccg | tacgtcgaaa | tgacattgag | attgatggag | 840 |
| cgttttggtg | tgaaagcaga | gcattctgat | agctgggaca | gattctacat | taagggaggt | 900 |
| caaaaataca | agtcccctaa | aaatgccatt | gttgaaggtg | atgcctcaag | cgcaagctat | 960 |
| ttcttggctg | tgctgcaat | tactggaggg | actgtgactg | tggaaggttg | tggcaccacc | 1020 |
| agtttgcagg | gtgatgtgaa | gtttgctgag | gtactggaga | tgatgggagc | gaaggttaca | 1080 |
| tggaccgaga | ctagcgtaac | tgttactggc | ccaccgcggg | agccatttgg | gaggaaacac | 1140 |
| ctcaaggcga | ttgatgtcaa | catgaacaag | atgcctgatg | tcgccatgac | tcttgctgtg | 1200 |
| gttgccctct | tgccgatgg | cccgacagcc | atcagagacg | tggcttcctg | gagagtaaag | 1260 |
| gagaccgaga | ggatggttgc | gatccggacg | gagctaacca | agctgggagc | atctgttgag | 1320 |
| gaagggccgg | actactgcat | catcacgccg | ccggagaagc | tgaacgtgac | ggcgatcgac | 1380 |
| acgtacgacg | accacaggat | ggccatggcc | ttctcccttg | ccgcctgtgc | cgaggtcccc | 1440 |
| gtcaccatcc | gggaccctgg | gtgcacccgg | aagaccttcc | ccgactactt | cgatgtgctg | 1500 |
| agcactttcg | tcaagaatta | a | | | | 1521 |

```
<210> SEQ ID NO 10
<211> LENGTH: 1521
<212> TYPE: DNA
<213> ORGANISM: Zea mays

<400> SEQUENCE: 10
```

```
atggcggcta tggccacgaa ggcagcggcc ggtacagtaa gcctcgattt ggcggccccc      60
tcccgtaggc accaccggcc aagcagtgcg aggccaccgt tcaggccagc agttcgcggt     120
cttagagcgc ctggtagaag ggttatcgca gcgccaccgg cggctgccgc tgcggcagcg     180
gtgcaggccg gcgcggaaga gatcgtccta cagcctatca aggaaatctc tggtacggta     240
aagttaccag gcagcaaaag tcttagcaac cgaatcctgc tgttggcggc actctctgaa     300
gggaccacgg tcgtagataa tctgctcaac agcgaagacg tgcactatat gttgggtgcc     360
ctgaggacgc taggtctgtc agtggaagcc gataaggccg ccaagcgcgc tgtcgtcgtt     420
ggctgcggcg gtaagttccc cgtggaggac gcgaaagaag aggtgcagtt atttcttggg     480
aacgctggca tcgccatgcg gtcccttacc gcagccgtca ccgctgcggg aggcaacgca     540
acttacgtgc ttgacggtgt tcctcgtatg agagagcggc ccatagggga tctcgtcgtg     600
gggctcaagc agctcggggc cgacgttgat tgcttcctcg gaaccgactg cccccctgtg     660
agggtgaacg gcatcggggg actgccagga ggcaaagtca agttgtccgg ctcaatttcc     720
tcgcagtacc tgagtgccct gcttatggcg gcccctctgg ctctgggaga cgtcgaaatt     780
gagatcattg ataagctgat ctctatccct tatgttgaga tgacactccg tctgatggaa     840
agattcgggg tcaaagctga gcactccgat tcctgggaca ggttctatat caagggcgga     900
cagaaatata agtcaccgaa gaatgcgtac gtcgagggag acgcatcgag cgcgagttac     960
ttccttgcgg gcgctgccat caccggggga accgtgacag tggaaggctg tgggacaacg    1020
agcttgcagg gcgacgtcaa atttgctgag gtgctagaaa tgatgggcgc taaggtgact    1080
tggactgaga cgtccgtgac cgttacggga ccgccccgcg aacctttcgg ccggaagcat    1140
ctgaaagcga ttgatgtgaa catgaataag atgccggacg tcgctatgac acttgccgtg    1200
gtggccctgt tcgctgacgg ccccaccgca atcaggatg tcgctagttg gagggtcaag    1260
gagacagagc gtatggtggc gatccgaacg gagctgacta aactcggggc cagtgtggag    1320
gagggccccgg attactgcat aatcacacct ccagagaagt tgaacgtcac cgctatcgac    1380
acatacgacg atcaccggat ggcaatggcc tttagcttgg cagcgtgcgc cgaagtacct    1440
gtgactataa gagatccagg ttgcacccgc aaaacgtttc ccgactattt cgacgtcctc    1500
tcaaccttcg tgaagaactg a                                               1521
```

<210> SEQ ID NO 11
<211> LENGTH: 76
<212> TYPE: PRT
<213> ORGANISM: Arabidopsis thaliana

<400> SEQUENCE: 11

Met Ala Gln Val Ser Arg Ile Cys Asn Gly Val Gln Asn Pro Ser Leu
1               5                   10                  15

Ile Ser Asn Leu Ser Lys Ser Ser Gln Arg Lys Ser Pro Leu Ser Val
            20                  25                  30

Ser Leu Lys Thr Gln Gln His Pro Arg Ala Tyr Pro Ile Ser Ser Ser
        35                  40                  45

Trp Gly Leu Lys Lys Ser Gly Met Thr Leu Ile Gly Ser Glu Leu Arg
    50                  55                  60

Pro Leu Lys Val Met Ser Ser Val Ser Thr Ala Cys
65                  70                  75

<210> SEQ ID NO 12
<211> LENGTH: 228
<212> TYPE: DNA

<213> ORGANISM: Arabidopsis thaliana

<400> SEQUENCE: 12

```
atggcgcaag ttagcagaat ctgcaatggt gtgcagaacc catctcttat ctccaatctc      60
tcgaaatcca gtcaacgcaa atctccctta tcggtttctc tgaagacgca gcagcatcca     120
cgagcttatc cgatttcgtc gtcgtgggga ttgaagaaga gtgggatgac gttaattggc     180
tctgagcttc gtcctcttaa ggtcatgtct tctgtttcca cggcgtgc                  228
```

<210> SEQ ID NO 13
<211> LENGTH: 228
<212> TYPE: DNA
<213> ORGANISM: Arabidopsis thaliana

<400> SEQUENCE: 13

```
atggcccagg taagtaggat ctgtaacgga gtccaaaacc cttcactaat atcgaacctg      60
tcaaaaagct ctcaaagaaa gtcgccgctt tctgtatcgt tgaaaactca acagcacccg     120
agggcttatc ccatctcaag ctcctggggt ctaaagaaaa gtggaatgac actgatcggt     180
agcgaactac gaccgctgaa agtcatgtcc tcagtcagca ctgcgtgc                  228
```

<210> SEQ ID NO 14
<211> LENGTH: 228
<212> TYPE: DNA
<213> ORGANISM: Arabidopsis thaliana

<400> SEQUENCE: 14

```
atggcgcaag taagtagaat ctgcaacggc gtgcagaacc cgtcgctgat ctccaacctc      60
agcaagtcca gccagcggaa gtcgccgctc tcggtcagcc tcaagaccca acagcacccg     120
agggcctacc ctatcagctc atcctggggc ctcaagaaga gtggcatgac gctgatcggc     180
agcgagctgc ggccactcaa ggtgatgtcc tcggtctcaa cggcgtgc                  228
```

<210> SEQ ID NO 15
<211> LENGTH: 455
<212> TYPE: PRT
<213> ORGANISM: Agrobacterium tumefaciens

<400> SEQUENCE: 15

```
Met Leu His Gly Ala Ser Ser Arg Pro Ala Thr Ala Arg Lys Ser Ser
1               5                   10                  15

Gly Leu Ser Gly Thr Val Arg Ile Pro Gly Asp Lys Ser Ile Ser His
            20                  25                  30

Arg Ser Phe Met Phe Gly Gly Leu Ala Ser Gly Glu Thr Arg Ile Thr
        35                  40                  45

Gly Leu Leu Glu Gly Glu Asp Val Ile Asn Thr Gly Lys Ala Met Gln
    50                  55                  60

Ala Met Gly Ala Arg Ile Arg Lys Glu Gly Asp Thr Trp Ile Ile Asp
65                  70                  75                  80

Gly Val Gly Asn Gly Gly Leu Leu Ala Pro Glu Ala Pro Leu Asp Phe
                85                  90                  95

Gly Asn Ala Ala Thr Gly Cys Arg Leu Thr Met Gly Leu Val Gly Val
            100                 105                 110

Tyr Asp Phe Asp Ser Thr Phe Ile Gly Asp Ala Ser Leu Thr Lys Arg
        115                 120                 125

Pro Met Gly Arg Val Leu Asn Pro Leu Arg Glu Met Gly Val Gln Val
    130                 135                 140
```

Lys Ser Glu Asp Gly Asp Arg Leu Pro Val Thr Leu Arg Gly Pro Lys
145                 150                 155                 160

Thr Pro Thr Pro Ile Thr Tyr Arg Val Pro Met Ala Ser Ala Gln Val
                165                 170                 175

Lys Ser Ala Val Leu Leu Ala Gly Leu Asn Thr Pro Gly Ile Thr Thr
            180                 185                 190

Val Ile Glu Pro Ile Met Thr Arg Asp His Thr Glu Lys Met Leu Gln
        195                 200                 205

Gly Phe Gly Ala Asn Leu Thr Val Glu Thr Asp Ala Asp Gly Val Arg
    210                 215                 220

Thr Ile Arg Leu Glu Gly Arg Gly Lys Leu Thr Gly Gln Val Ile Asp
225                 230                 235                 240

Val Pro Gly Asp Pro Ser Ser Thr Ala Phe Pro Leu Val Ala Ala Leu
                245                 250                 255

Leu Val Pro Gly Ser Asp Val Thr Ile Leu Asn Val Leu Met Asn Pro
            260                 265                 270

Thr Arg Thr Gly Leu Ile Leu Thr Leu Gln Glu Met Gly Ala Asp Ile
        275                 280                 285

Glu Val Ile Asn Pro Arg Leu Ala Gly Gly Glu Asp Val Ala Asp Leu
    290                 295                 300

Arg Val Arg Ser Ser Thr Leu Lys Gly Val Thr Val Pro Glu Asp Arg
305                 310                 315                 320

Ala Pro Ser Met Ile Asp Glu Tyr Pro Ile Leu Ala Val Ala Ala Ala
                325                 330                 335

Phe Ala Glu Gly Ala Thr Val Met Asn Gly Leu Glu Glu Leu Arg Val
            340                 345                 350

Lys Glu Ser Asp Arg Leu Ser Ala Val Ala Asn Gly Leu Lys Leu Asn
        355                 360                 365

Gly Val Asp Cys Asp Glu Gly Glu Thr Ser Leu Val Val Arg Gly Arg
    370                 375                 380

Pro Asp Gly Lys Gly Leu Gly Asn Ala Ser Gly Ala Ala Val Ala Thr
385                 390                 395                 400

His Leu Asp His Arg Ile Ala Met Ser Phe Leu Val Met Gly Leu Val
                405                 410                 415

Ser Glu Asn Pro Val Thr Val Asp Asp Ala Thr Met Ile Ala Thr Ser
            420                 425                 430

Phe Pro Glu Phe Met Asp Leu Met Ala Gly Leu Gly Ala Lys Ile Glu
        435                 440                 445

Leu Ser Asp Thr Lys Ala Ala
    450                 455

<210> SEQ ID NO 16
<211> LENGTH: 1368
<212> TYPE: DNA
<213> ORGANISM: Agrobacterium tumefaciens

<400> SEQUENCE: 16
atgcttcacg gtgcaagcag ccggcccgca accgcccgca atcctctgg cctttccgga      60 accgtccgca ttcccggcga caagtcgatc tcccaccggt ccttcatgtt cggcggtctc    120
gcgagcggtg aaacgcgcat caccggcctt ctggaaggcg aggacgtcat caatacgggc    180
aaggccatgc aggcgatggg cgcccgcatc cgtaaggaag cgacacctg gatcatcgat    240 ggcgtcggca atggcggcct cctggcgcct gaggcgccgc tcgatttcgg caatgccgcc    300
acgggctgcc gcctgacgat gggcctcgtc ggggtctacg atttcgacag caccttcatc    360

```
ggcgacgcct cgctcacaaa gcgcccgatg ggccgcgtgt tgaacccgct gcgcgaaatg    420
ggcgtgcagg tgaaatcgga agacggtgac cgtcttcccg ttaccttgcg cgggccgaag    480
acgccgacgc cgatcaccta ccgcgtgccg atggcctccg cacaggtgaa gtccgccgtg    540
ctgctcgccg gcctcaacac gcccggcatc acgacggtca tcgagccgat catgacgcgc    600
gatcatacgg aaaagatgct gcagggcttt ggcgccaacc ttaccgtcga cggatgcg     660 gacggcgtgc gcaccatccg cctggaaggc gcggcaagc tcaccggcca agtcatcgac    720
gtgccgggcg acccgtcctc gacggccttc ccgctggttg cggccctgct tgttccgggc    780
tccgacgtca ccatcctcaa cgtgctgatg aaccccaccc gcaccggcct catcctgacg    840
ctgcaggaaa tgggcgccga catcgaagtc atcaacccgc gccttgccgg cggcgaagac    900
gtggcggacc tgcgcgttcg ctcctccacg ctgaagggcg tcacggtgcc ggaagaccgc    960
gcgccttcga tgatcgacga atatccgatt ctcgctgtcg ccgccgcctt cgcggaaggg   1020
gcgaccgtga tgaacggtct ggaagaactc gcgtcaagg aaagcgaccg cctctcggcc    1080
gtcgccaatg gcctcaagct caatggcgtg gattgcgatg agggcgagac gtcgctcgtc   1140
gtgcgtggcc gccctgacgg caaggggctc ggcaacgcct cgggcgccgc cgtcgccacc   1200
catctcgatc accgcatcgc catgagcttc ctcgtcatgg gcctcgtgtc ggaaaaccct   1260
gtcacggtgg acgatgccac gatgatcgcc acgagcttcc cggagttcat ggacctgatg   1320
gccgggctgg gcgcgaagat cgaactctcc gatacgaagg ctgcctga               1368

<210> SEQ ID NO 17
<211> LENGTH: 1368
<212> TYPE: DNA
<213> ORGANISM: Agrobacterium tumefaciens

<400> SEQUENCE: 17
atgcttcatg gagcttcatc taggccagct actgccagga agtctagcgg gctcagtggc     60
accgtgcgca tccctggcga taaaagtatt tcacacagga gcttcatgtt cggaggactt    120
gctagtggag agacgagaat cactggtttg cttgagggcg aagatgttat caacaccggt    180
aaggcgatgc aagcaatggg tgccagaatc cgaaaagagg gcgatacgtg gatcatcgac    240
ggtgttggta acggaggatt gctcgctccc gaagcgccac ttgactttgg gaacgcagct    300
acggggtgcc gtcttactat gggactggta ggcgtgtatg actttgactc taccttcatc    360
ggtgacgcga gcctcactaa gagaccaatg ggacgagtgc tgaatcccct gagggagatg    420
ggtgtccagg tgaaatctga ggatggtgat cgtcttccgg ttactctgcg aggccccaag    480 accccacgc caatcacgta cagggttccg atggcgtcag cacaggtcaa gtcagcggta    540 ctcctggcg gcctcaacac acctggaatc acaaccgtga ttgaacccat catgactaga    600
gaccacacgg agaagatgtt gcagggtttc ggcgctaatc taacggtcga aaccgacgcc    660
gacggcgtga ggcaatccg cttggagggc agagtaaac tgactggcca agtcatcgat    720
gtgcctggag atccctcgtc cacagcgttt cccctcgtag ctgcgttgct cgtccctgga    780
tctgatgtga cgatcctgaa tgtcctcatg aatccaacta gaaccggcct catcctcaca    840
ttgcaggaga tgggtgctga catcgaggtt atcaatccta ggttggcagg tggagaggat    900
gtggccgatc tgcgcgtgcg ttctagtaca ctcaaaggcg tgaccgtccc tgaggatcgc    960
gctccatcca tgatcgacga gtaccccatt ctcgccgttg ctgctgcgtt tgccgagggc   1020
gcaactgtaa tgaacggcct tgaggagttg agggttaagg agagtgacag gctgtccgcg   1080
```

```
gtggcgaatg gcctgaagct aaacggcgtg gactgcgacg aaggtgaaac gtcccttgta   1140
gtccgtggtc gcccagacgg aaggggttg gggaatgctt cgggagctgc tgtggcgacg    1200
caccttgatc atagaatcgc catgtcattt ctggtgatgg gacttgtctc cgagaatccg   1260
gtgaccgttg acgatgctac catgatcgcc acctcctttc ctgagttcat ggacctcatg   1320
gcaggcttgg gggccaagat cgagctgtct gatactaagg ccgcttga               1368

<210> SEQ ID NO 18
<211> LENGTH: 1368
<212> TYPE: DNA
<213> ORGANISM: Agrobacterium tumefaciens

<400> SEQUENCE: 18
atgctacacg gtgcaagcag ccggccggca accgctcgca aatcttccgg cctttcggga     60
acggtcagga ttccgggcga taagtccata tcccaccggt cgttcatgtt cggcggtctt   120
gccagcggtg agacgcgcat cacgggcctg cttgaaggtg aggacgtgat caataccggg   180
aaggccatgc aggctatggg agcgcgtatc cgcaaggaag gtgacacatg gatcattgac   240
ggcgttggga atggcggtct gctcgcccct gaggcccctc tcgacttcgg caatgcggcg   300
acgggctgca ggctcactat gggactggtc ggggtgtacg acttcgatag cacgttcatc   360
ggagacgcct cgctcacaaa gcgcccaatg ggccgcgttc tgaacccgtt gcgcgagatg   420
ggcgtacagg tcaaatccga ggatggtgac cgtttgcccg ttacgctgcg cgggccgaag   480
acgcctaccc cgattaccta ccgcgtgcca atggcatccg cccaggtcaa gtcagccgtg   540
ctcctcgccg gactgaacac tccgggcatc accacggtga tcgagcccat catgaccagg   600
gatcataccg aaaagatgct tcaggggttt ggcgccaacc tgacggtcga gacggacgct   660
gacggcgtca ggaccatccg ccttgagggc aggggtaaac tgactggcca agtcatcgat   720
gttccgggag acccgtcgtc cacggccttc ccgttggttg cggcgctgct cgtgccgggg   780
agtgacgtga ccatcctgaa cgtcctcatg aacccgacca ggaccggcct gatcctcacg   840
cttcaggaga tgggagccga catcgaggtg atcaacccgc gcctggcagg cggtgaagac   900
gttgcggatc tgcgcgtgcg ctcctctacc ctgaagggcg tgacggtccc ggaagatcgc   960
gcgccgtcca tgatagacga gtatcctatt ctggccgtcg ccgctgcgtt cgccgaaggg  1020
gccacggtca tgaacggtct tgaggaactc gcgtgaagg aatcggatcg cctgtcggcg  1080
gtggccaatg gcctgaagct caacggtgtt gactgcgacg agggtgagac ctcactcgtg  1140
gtccgtggcc ggcctgatgg caagggcctc ggcaacgcca gtggagcggc cgtcgccacg  1200
caccatgatc atcgcatcgc gatgtccttc ttggtgatgg gtctcgtctc agagaacccg  1260
gtgaccgtcg atgacgccac gatgatagcg acgagcttcc cagagttcat ggatctgatg  1320
gcgggcctcg gggccaagat cgaactgtct gacacgaagg ccgcttga               1368

<210> SEQ ID NO 19
<211> LENGTH: 183
<212> TYPE: PRT
<213> ORGANISM: Streptomyces hygroscopicus

<400> SEQUENCE: 19

Met Ser Pro Glu Arg Arg Pro Ala Asp Ile Arg Arg Ala Thr Glu Ala
1               5                   10                  15

Asp Met Pro Ala Val Cys Thr Ile Val Asn His Tyr Ile Glu Thr Ser
                20                  25                  30

Thr Val Asn Phe Arg Thr Glu Pro Gln Glu Pro Gln Asp Trp Thr Asp
```

```
                    35                  40                  45
Asp Leu Val Arg Leu Arg Glu Arg Tyr Pro Trp Leu Val Ala Glu Val
 50                  55                  60

Asp Gly Glu Val Ala Gly Ile Ala Tyr Ala Gly Pro Trp Lys Ala Arg
 65                  70                  75                  80

Asn Ala Tyr Asp Trp Thr Ala Glu Ser Thr Val Tyr Val Ser Pro Arg
                 85                  90                  95

His Gln Arg Thr Gly Leu Gly Ser Thr Leu Tyr Thr His Leu Leu Lys
            100                 105                 110

Ser Leu Glu Ala Gln Gly Phe Lys Ser Val Val Ala Val Ile Gly Leu
        115                 120                 125

Pro Asn Asp Pro Ser Val Arg Met His Glu Ala Leu Gly Tyr Ala Pro
    130                 135                 140

Arg Gly Met Leu Arg Ala Ala Gly Phe Lys His Gly Asn Trp His Asp
145                 150                 155                 160

Val Gly Phe Trp Gln Leu Asp Phe Ser Leu Pro Val Pro Arg Pro
                165                 170                 175

Val Leu Pro Val Thr Glu Ile
            180

<210> SEQ ID NO 20
<211> LENGTH: 552
<212> TYPE: DNA
<213> ORGANISM: Streptomyces hygroscopicus

<400> SEQUENCE: 20
atgagcccag aacgacgccc ggccgacatc cgccgtgcca ccgaggcgga catgccggcg      60
gtctgcacca tcgtcaacca ctacatcgag acaagcacgg tcaacttccg taccgagccg     120
caggaaccgc aggactggac ggacgacctc gtccgtctgc gggagcgcta tccctggctc     180
gtcgccgagg tggacggcga ggtcgccggc atcgcctacg cgggcccctg gaaggcacgc     240
aacgcctacg actggacggc cgagtcgacc gtgtacgtct cccccccgcca ccagcggacg     300 ggactgggct ccacgctcta cacccacctg ctgaagtccc tggaggcaca gggcttcaag     360
agcgtggtcg ctgtcatcgg gctgcccaac gacccgagcg tgcgcatgca cgaggcgctc     420
ggatatgccc cccgcggcat gctgcgggcg gccggcttca gcacgggaa ctggcatgac     480 gtgggttttct ggcagctgga cttcagcctg ccggtaccgc ccgtccggt cctgcccgtc     540 accgagatct ga                                                         552

<210> SEQ ID NO 21
<211> LENGTH: 552
<212> TYPE: DNA
<213> ORGANISM: Streptomyces hygroscopicus

<400> SEQUENCE: 21
atgagtccag aaaggagacc ggctgatatt cggagagcca ccgaagctga tatgcctgct      60
gtttgtacaa tcgtaaacca ttatatcgag acctcgacag ttaattttcg cactgagccg     120
caggagccac aggattggac ggacgatctg gtacgtttaa gaaacgtta tccgtggcta     180 gttgctgagg ttgacggaga agtcgctggt atagcttacg ctggaccgtg aaagctcgt     240 aacgcttacg actggacagc agaatccact gtctacgtca gccctcgtca tcaaagaacc     300
ggattaggga gcacgttgta cactcatctt ttaaagtcac tggaggcaca aggcttcaag     360
tctgttgtgg cagttattgg attgccaaac gatccgagtg ttcgaatgca cgaagcgctt     420
```

```
ggatacgctc cacgaggtat gctccgtgct gccggattca acatggaaa ttggcacgac      480 gtaggttttt ggcaactgga cttttcactt cccgttcccc ctagacctgt acttccagtt      540
actgaaatct ag                                                         552

<210> SEQ ID NO 22
<211> LENGTH: 552
<212> TYPE: DNA
<213> ORGANISM: Streptomyces hygroscopicus

<400> SEQUENCE: 22
atgtcgcctg agcgccgtcc tgctgacata agacgcgcta ccgaggcaga catgcctgct       60
gtttgcacca ttgtgaatca ctacatcgag acatctacgg taaacttccg cactgagcct      120
caagaaccgc aggattggac cgacgatctc gtgcgtctca gagagcgtta ccgtggctg       180 gttgcagagg tggacggtga agtggctggg atcgcctacg ctggaccgtg aaggctaga      240 aacgcatacg attggactgc ggagtccaca gtctacgtct cacccagaca tcaaagaacc      300
gggctcggct cgaccctcta tacgcatctc ctcaagtcct tagaggcgca gggcttcaaa      360
tctgtagtgg cggtgatcgg cttgccaaac gatcccagtg tgagaatgca cgaggcactc      420
ggttacgctc ctagaggaat gctcagggcg gctggattca agcacggtaa ttggcacgac      480
gttggcttct ggcaactgga cttctctttg ccagttccac ctcgtcctgt gctacccgtc      540
accgaaatct ag                                                         552

<210> SEQ ID NO 23
<211> LENGTH: 1368
<212> TYPE: DNA
<213> ORGANISM: Agrobacterium tumefaciens

<400> SEQUENCE: 23
atgcttcacg gtgcaagcag ccgtccagca actgctcgta agtcctctgg tctttctgga       60
accgtccgta ttccaggtga caagtctatc tcccacaggt ccttcatgtt ggaggtctc      120 gctagcggtg aaactcgtat caccggtctt ttggaaggtg aagatgttat caacactggt      180
aaggctatgc aagctatggg tgccagaatc cgtaaggaag gtgatacttg gatcattgat      240
ggtgttggta acggtggact ccttgctcct gaggctcctc tcgatttcgg taacgctgca      300
actggttgcc gtttgactat gggtcttgtt ggtgtttacg atttcgatag cacttttcatt      360 ggtgacgctt ctctcactaa gcgtccaatg ggtcgtgtgt tgaacccact tcgcgaaatg      420
ggtgtgcagg tgaagtctga agacggtgat cgtcttccag ttaccttgcg tggaccaaag      480
actccaacgc caatcaccta cagggtacct atggcttccg ctcaagtgaa gtccgctgtt      540
ctgcttgctg gtctcaacac cccaggtatc accactgtta tcgagccaat catgactcgt      600
gaccacactg aaaagatgct tcaaggtttt ggtgctaacc ttaccgttga gactgatgct      660
gacggtgtgc gtaccatccg tcttgaaggt cgtggtaagc tcaccggtca agtgattgat      720
gttccaggtg atccatcctc tactgctttc ccattggttg ctgccttgct tgttccaggt      780
tccgacgtca ccatccttaa cgttttgatg aacccaaccc gtactggtct catcttgact      840
ctgcaggaaa tgggtgccga catcgaagtg atcaacccac gtcttgctgg tggagaagac      900
gtggctgact tgcgtgttcg ttcttctact ttgaagggtg ttactgttcc agaagaccgt      960
gctccttcta tgatcgacga gtatccaatt ctcgctgttg cagctgcatt cgctgaaggt     1020
gctaccgtta tgaacggttt ggaagaactc cgtgttaagg aaagcgaccg tctttctgct     1080
gtcgcaaacg gtctcaagct caacggtgtt gattgcgatg aaggtgagac ttctctcgtc     1140
```

```
gtgcgtggtc gtcctgacgg taagggtctc ggtaacgctt ctggagcagc tgtcgctacc    1200
cacctcgatc accgtatcgc tatgagcttc ctcgttatgg gtctcgtttc tgaaaaccct    1260
gttactgttg atgatgctac tatgatcgct actagcttcc cagagttcat ggatttgatg    1320
gctggtcttg gagctaagat cgaactctcc gacactaagg ctgcttga                 1368
```

<210> SEQ ID NO 24
<211> LENGTH: 16
<212> TYPE: DNA
<213> ORGANISM: Artificial sequence
<220> FEATURE:
<223> OTHER INFORMATION: DNA Primer molecule

<400> SEQUENCE: 24

```
catggagctt catcta                                                    16
```

<210> SEQ ID NO 25
<211> LENGTH: 16
<212> TYPE: DNA
<213> ORGANISM: Artificial sequence
<220> FEATURE:
<223> OTHER INFORMATION: DNA Primer molecule

<400> SEQUENCE: 25

```
gcctttgagt gtacta                                                    16
```

<210> SEQ ID NO 26
<211> LENGTH: 16
<212> TYPE: DNA
<213> ORGANISM: Artificial sequence
<220> FEATURE:
<223> OTHER INFORMATION: DNA Primer molecule

<400> SEQUENCE: 26

```
gggagcgcgt atccgc                                                    16
```

<210> SEQ ID NO 27
<211> LENGTH: 16
<212> TYPE: DNA
<213> ORGANISM: Artificial sequence
<220> FEATURE:
<223> OTHER INFORMATION: DNA Primer molecule

<400> SEQUENCE: 27

```
ggatggtcac gtcact                                                    16
```

<210> SEQ ID NO 28
<211> LENGTH: 16
<212> TYPE: DNA
<213> ORGANISM: Artificial sequence
<220> FEATURE:
<223> OTHER INFORMATION: DNA Primer molecule

<400> SEQUENCE: 28

```
cggcatcacg acggtc                                                    16
```

<210> SEQ ID NO 29
<211> LENGTH: 16
<212> TYPE: DNA
<213> ORGANISM: Artificial sequence
<220> FEATURE:
<223> OTHER INFORMATION: DNA Primer molecule

<400> SEQUENCE: 29

-continued

```
ggcatcgtcc accgtg                                                    16

<210> SEQ ID NO 30
<211> LENGTH: 16
<212> TYPE: DNA
<213> ORGANISM: Artificial sequence
<220> FEATURE:
<223> OTHER INFORMATION: DNA Primer molecule

<400> SEQUENCE: 30
gcaactggtt gccgtt                                                    16

<210> SEQ ID NO 31
<211> LENGTH: 16
<212> TYPE: DNA
<213> ORGANISM: Artificial sequence
<220> FEATURE:
<223> OTHER INFORMATION: DNA Primer molecule

<400> SEQUENCE: 31
atcacctgga acatca                                                    16

<210> SEQ ID NO 32
<211> LENGTH: 22
<212> TYPE: DNA
<213> ORGANISM: Zea mays

<400> SEQUENCE: 32
cgtcaagatc ctcttcacct cg                                             22

<210> SEQ ID NO 33
<211> LENGTH: 22
<212> TYPE: DNA
<213> ORGANISM: Zea mays

<400> SEQUENCE: 33
acaccctctc caacactctc ta                                             22

<210> SEQ ID NO 34
<211> LENGTH: 9
<212> TYPE: PRT
<213> ORGANISM: Artificial sequence
<220> FEATURE:
<223> OTHER INFORMATION: Motif providing glyphosate resistance to a
      plant EPSPS

<400> SEQUENCE: 34

Gly Asn Ala Gly Ile Ala Met Lys Ser
1               5

<210> SEQ ID NO 35
<211> LENGTH: 1596
<212> TYPE: DNA
<213> ORGANISM: Agrobacterium tumefaciens

<400> SEQUENCE: 35
atggcccaag ttagccgaat ctgcaacggt gtgcagaatc catcactaat ctccaacctg    60
tccaaatcgt cacaacgtaa gtcgccatta tctgttagct tgaagactca gcaacatcct   120
cgcgcatatc ctatatcaag cagttggggt ttgaagaaat cgggtatgac cttgattggt   180
tcggaactta ggccattgaa ggtgatgtct tcagttagta cagcttgcat gcttcacggt   240
gcttcttcca gacccgcaac ggctagaaag agttctggct tgtctggaac cgtccgtatt   300
ccaggagaca aaagcattag tcaccgctct ttcatgtttg gtgggctggc atctggagag   360
```

```
acgcgcatca ctggtcttct ggaaggagag gacgtcatca atacaggaa ggcaatgcag    420 gctatgggtg cccgtattcg caaggaaggt gatacttgga tcatagacgg agttgggaac    480
ggtggcttac ttgcaccgga ggctcctctc gactttggca acgcagccac agggtgtaga    540
cttactatgg gcctcgtggg tgtttacgat ttcgattcaa cctttattgg ggatgcctct    600
ctcactaaac gcccaatggg aagagtcctt aacccgttga gggagatggg cgtacaagtt    660
aagtccgagg acggcgacag attgcccgtc accttgcgcg ccctaagac acccacccct    720 attacttaca gggttccaat ggcatctgct caagtgaagt ccgcagttct gctcgctgga    780
ttgaacacac cggtattac taccgtgatt gagccgatca tgactcgtga ccacactgag    840
aagatgcttc agggtttcgg tgctaacctc accgttgaaa cagacgcgga cggtgtgagg    900
accattcgcc tggagggaag gggaaaactc actggtcaag tcattgacgt gcccggtgat    960
ccctccagca cggcgttccc actggttgcc gctcttctcg taccaggctc cgatgtgaca   1020
attctaaacg tcctcatgaa tcctactaga accggattga tacttacatt gcaggaaatg   1080
ggtgctgata ttgaagttat caatcctaga ctagccggag gtgaggacgt agctgatttg   1140
cgggtgaggt cttctacatt gaaaggtgtt accgtacctg aagatagggc accttcaatg   1200
attgacgagt atccaattct tgccgtcgcg gctgcctttg ctgagggcgc gaccgtgatg   1260
aatggactag aggagttgag agtgaaggaa tccgacagat tgagcgcagt cgctaacgga   1320
cttaaactca atggcgttga ttgtgatgag ggtgagacta gcttggtagt ccgtgggcga   1380
ccagacggaa agggtttggg caacgcttcg ggtgctgccg ttgcaactca cttggatcat   1440
cggatagcga tgagttttct ggtgatgggt ctcgtaagcg agaatcctgt gacagtcgac   1500
gatgcaacta tgatcgctac ttccttccct gagtttatgg atttaatggc aggactaggt   1560
gcaaagattg aactctctga taccaaagcg gcctaa                             1596
```

<210> SEQ ID NO 36
<211> LENGTH: 1596
<212> TYPE: DNA
<213> ORGANISM: Artificial sequence
<220> FEATURE:
<223> OTHER INFORMATION: Hybrid

<400> SEQUENCE: 36

```
atggcgcaag ttagcagaat ctgcaatggt gtgcagaacc catctcttat ctccaatctc     60
tcgaaatcca gtcaacgcaa atctcccta tcggtttctc tgaagacgca gcagcatcca    120
cgagcttatc cgatttcgtc gtcgtgggga ttgaagaaga gtgggatgac gttaattggc    180
tctgagcttc gtcctcttaa ggtcatgtct tctgtttcca cggcgtgcat gcttcacggt    240
gcaagcagcc ggcccgcaac cgcccgcaaa tcctctggcc tttccggaac cgtccgcatt    300
cccggcgaca gtcgatctc ccaccggtcc ttcatgttcg gcggtctcgc gagcggtgaa    360
acgcgcatca ccggccttct ggaaggcgag gacgtcatca atacgggcaa ggccatgcag    420
gcgatgggcg cccgcatccg taaggaaggc gacacctgga tcatcgatgg cgtcggcaat    480
ggcggcctcc tggcgcctga ggcgccgctc gatttcggca atgccgccac gggctgccgc    540
ctgacgatgg gcctcgtcgg ggtctacgat ttcgacagca ccttcatcgg cgacgcctcg    600
ctcacaaagc gcccgatggg ccgcgtgttg aacccgctgc gcgaaatggg cgtgcaggtg    660
aaatcggaag acggtgaccg tcttcccgtt accttgcgcg ggccgaagac gccgacgccg    720
atcacctacc gcgtgccgat ggcctccgca caggtgaagt ccgccgtgct gctcgccggc    780
```

| | |
|---|---|
| ctcaacacgc cggcatcac gacggtcatc gagccgatca tgacgcgcga tcatacggaa | 840 |
| aagatgctgc agggctttgg cgccaacctt accgtcgaga cggatgcgga cggcgtgcgc | 900 |
| accatccgcc tggaaggccg cggcaagctc accggccaag tcatcgacgt gccgggcgac | 960 |
| ccgtcctcga cggccttccc gctggttgcg gccctgcttg ttccgggctc cgacgtcacc | 1020 |
| atcctcaacg tgctgatgaa ccccacccgc accgcctca tcctgacgct gcaggaaatg | 1080 |
| ggcgccgaca tcgaagtcat caacccgcgc cttgccggcg gcgaagacgt ggcggacctg | 1140 |
| cgcgttcgct cctccacgct gaagggcgtc acggtgccgg aagaccgcgc gccttcgatg | 1200 |
| atcgacgaat atccgattct cgctgtcgcc gccgccttcg cggaaggggc gaccgtgatg | 1260 |
| aacggtctgg aagaactccg cgtcaaggaa agcgaccgcc tctcggccgt cgccaatggc | 1320 |
| ctcaagctca atggcgtgga ttgcgatgag ggcgagacgt cgctcgtcgt gcgtggccgc | 1380 |
| cctgacggca aggggctcgg caacgcctcg ggcgccgccg tcgccaccca tctcgatcac | 1440 |
| cgcatcgcca tgagcttcct cgtcatgggc ctcgtgtcgg aaaaccctgt cacggtggac | 1500 |
| gatgccacga tgatcgccac gagcttcccg gagttcatgg acctgatggc cgggctgggc | 1560 |
| gcgaagatcg aactctccga tacgaaggct gcctga | 1596 |

<210> SEQ ID NO 37
<211> LENGTH: 1596
<212> TYPE: DNA
<213> ORGANISM: Artificial sequence
<220> FEATURE:
<223> OTHER INFORMATION: Hybrid

<400> SEQUENCE: 37

| | |
|---|---|
| atggcccagg taagtaggat ctgtaacgga gtccaaaacc cttcactaat atcgaacctg | 60 |
| tcaaaaagct ctcaaagaaa gtcgccgctt tctgtatcgt tgaaaactca acagcacccg | 120 |
| agggcttatc ccatctcaag ctcctggggt ctaaagaaaa gtggaatgac actgatcggt | 180 |
| agcgaactac gaccgctgaa agtcatgtcc tcagtcagca ctgcgtgcat gcttcatgga | 240 |
| gcttcatcta ggccagctac tgccaggaag tctagcgggc tcagtggcac cgtgcgcatc | 300 |
| cctggcgata aaagtatttc acacaggagc ttcatgttcg gaggacttgc tagtggagag | 360 |
| acgagaatca ctggtttgct tgagggcgaa gatgttatca acaccggtaa ggcgatgcaa | 420 |
| gcaatgggtg ccagaatccg aaaagagggc gatacgtgga tcatcgacgg tgttggtaac | 480 |
| ggaggattgc tcgctcccga agcgccactt gactttggga acgcagctac ggggtgccgt | 540 |
| cttactatgg gactggtagg cgtgtatgac tttgactcta ccttcatcgg tgacgcgagc | 600 |
| ctcactaaga gaccaatggg acgagtgctg aatcccctga gggagatggg tgtccaggtg | 660 |
| aaatctgagg atggtgatcg tcttccggtt actctgcgag gccccaagac ccccacgcca | 720 |
| atcacgtaca gggttccgat ggcgtcagca caggtcaagt cagcggtact cctggcgggc | 780 |
| ctcaacacac ctggaatcac aaccgtgatt gaacccatca tgactagaga ccacacggag | 840 |
| aagatgttgc agggtttcgg cgctaatcta acggtcgaaa ccgacgccga cggcgtgagg | 900 |
| acaatccgct ggagggcag aggtaaactg actggccaag tcatcgatgt gcctggagat | 960 |
| ccctcgtcca cagcgtttcc cctcgtagct cgttgctcg tccctggatc tgatgtgacg | 1020 |
| atcctgaatg tcctcatgaa tccaactaga accggcctca tcctcacatt gcaggagatg | 1080 |
| ggtgctgaca tcgaggttat caatcctagg ttggcaggtg gagaggatgt ggccgatctg | 1140 |
| cgcgtgcgtt ctagtacact caaaggcgtg accgtccctg aggatcgcgc tccatccatg | 1200 |
| atcgacgagt accccattct cgccgttgct gctgcgtttg ccgagggcgc aactgtaatg | 1260 |

```
aacggccttg aggagttgag ggttaaggag agtgacaggc tgtccgcggt ggcgaatggc    1320
ctgaagctaa acggcgtgga ctgcgacgaa ggtgaaacgt cccttgtagt ccgtggtcgc    1380
ccagacggga aggggttggg gaatgcttcg ggagctgctg tggcgacgca ccttgatcat    1440
agaatcgcca tgtcatttct ggtgatggga cttgtctccg agaatccggt gaccgttgac    1500
gatgctacca tgatcgccac ctcctttcct gagttcatgg acctcatggc aggcttgggg    1560
gccaagatcg agctgtctga tactaaggcc gcttga                              1596
```

<210> SEQ ID NO 38
<211> LENGTH: 1596
<212> TYPE: DNA
<213> ORGANISM: Artificial sequence
<220> FEATURE:
<223> OTHER INFORMATION: Hybrid

<400> SEQUENCE: 38

```
atggcgcaag taagtagaat ctgcaacggc gtgcagaacc cgtcgctgat ctccaacctc      60
agcaagtcca gccagcggaa gtcgccgctc tcggtcagcc tcaagaccca acagcacccg     120
agggcctacc ctatcagctc atcctggggc ctcaagaaga gtggcatgac gctgatcggc     180
agcgagctgc ggccactcaa ggtgatgtcc tcggtctcaa cggcgtgcat gctacacggt     240
gcaagcagcc ggccggcaac cgctcgcaaa tcttccggcc tttcgggaac ggtcaggatt     300
ccgggcgata agtccatatc ccaccggtcg ttcatgttcg gcggtcttgc cagcggtgag     360
acgcgcatca cgggcctgct tgaaggtgag gacgtgatca ataccgggaa ggccatgcag     420
gctatgggag cgcgtatccg caaggaaggt gacacatgga tcattgacgg cgttgggaat     480
ggcggtctgc tcgcccctga ggcccctctc gacttcggca atgcggcgac gggctgcagg     540
ctcactatgg gactggtcgg ggtgtacgac ttcgatagca cgttcatcgg agacgcctcg     600
ctcacaaagc gcccaatggg ccgcgttctg aacccgttgc gcgagatggg cgtacaggtc     660
aaatccgagg atggtgaccg tttgcccgtt acgctgcgcg ggccgaagac gcctaccccg     720
attacctacc gcgtgccaat ggcatccgcc caggtcaagt cagccgtgct cctcgccgga     780
ctgaacactc cgggcatcac cacggtgatc gagcccatca tgaccaggga tcataccgaa     840
aagatgcttc aggggtttgg cgccaacctg acggtcgaga cggacgctga cggcgtcagg     900
accatccgcc ttgagggcag gggtaaactg actggccaag tcatcgatgt tccgggagac     960
ccgtcgtcca cggccttccc gttggttgcg cgctgctcg tgccggggag tgacgtgacc    1020
atcctgaacg tcctcatgaa cccgaccagg accggcctga tcctcacgct tcaggagatg    1080
ggagccgaca tcgaggtgat caacccgcgc ctggcaggcg gtgaagacgt tgcggatctg    1140
cgcgtgcgct cctctaccct gaagggcgtg acggtcccgg aagatcgcgc gccgtccatg    1200
atagacgagt atcctattct ggccgtcgcc gctgcgttcg ccgaaggggc cacggtcatg    1260
aacggtcttg aggaactccg cgtgaaggaa tcggatcgcc tgtcggcggt ggccaatggc    1320
ctgaagctca acggtgttga ctgcgacgag ggtgagacct cactcgtggt ccgtggccgg    1380
cctgatggca agggcctcgg caacgccagt ggagcggccg tcgccacgca cctcgatcat    1440
cgcatcgcga tgtccttctt ggtgatgggt ctcgtctcag agaacccggt gaccgtcgat    1500
gacgccacga tgatagcgac gagcttccca gagttcatgg atctgatggc gggcctcggg    1560
gccaagatcg aactgtctga cacgaaggcc gcttga                              1596
```

METHODS FOR USING ARTIFICIAL POLYNUCLEOTIDES AND COMPOSITIONS THEREOF TO REDUCE TRANSGENE SILENCING

This application is a divisional of U.S. application Ser. No. 13/035,898, filed Feb. 25, 2011, which application is a divisional of U.S. application Ser. No. 12/589,141, filed Oct. 19,2009, now issued as U.S Pat. No. 7,979,321 which application is a divisional of U.S. application Ser. No. 10/521,288 filed Jan. 14, 2005, now issued as U.S. Pat. No. 7,615,678, which is a National Stage Entry of PCT/US03/21551, filed on Jul. 10, 2003, which application claims benefit of priority of U.S. Provisional Application No. 60/396,665, filed Jul. 18, 2002, the entire disclosure of all of which are incorporated herein by reference in their entirety.

INCORPORATION OF SEQUENCE LISTING

A computer readable form of the sequence listing is contained in the file named "MONS270USD3_ST25.txt" which is 55.8 kb (measured in MS-Windows) and was created on Sep. 16, 2013, which is filed herewith and herein incorporated by reference.

BACKGROUND OF THE INVENTION

1. Field of the Invention

The present invention relates to plant genetic engineering. More particularly, to a method for constructing an artificial polynucleotide and methods of use to reduce transgene silencing in plants. The invention also relates to the plant cells containing the artificial polynucleotide in which a plant cell is transformed to express the artificial polynucleotide and the plant regenerated therefrom.

2. Description of the Related Art

Heterologous genes may be isolated from a source other than the plant into which it will is be transformed or they may be modified or designed to have different or improved qualities. Particularly desirable traits or qualities of interest for plant genetic engineering would include but are not limited to resistance to insects, fungal diseases, and other pests and disease-causing agents, tolerances to herbicides, enhanced stability or shelf-life, yield, environmental stress tolerances, and nutritional enhancements.

Traditional molecular biological methods for generating novel genes and proteins generally involved random or directed mutagenesis. An example of random mutagenesis is a recombination technique known as "DNA shuffling" as disclosed in U.S. Pat. Nos. 5,605,793; 5,811,238; 5,830,721; 5,837,458 and International Applications WO 98/31837, WO 99/65927, the entirety of all of which is incorporated herein by reference. An alternative method of molecular evolution involves a staggered extension process (StEP) for in vitro mutagenesis and recombination of nucleic acid molecule sequences, as disclosed in U.S. Pat. No. 5,965,408, incorporated herein by reference. An example of directed mutagenesis is the introduction of a point mutation at a specific site in a polypeptide.

An alternative approach, useful when the heterologous gene is from a non-plant source, is to design an artificial insecticidal gene that uses the most often used codon in maize plant codon usage table (Koziel et al., 1993, Biotechnology 11, 194-200). Fischhoff and Perlak (U.S. Pat. No. 5,500,365, incorporated herein by reference) report higher expression of *Bacillus thuringiensis* (Bt) insecticidal protein compared in crop plants when the polynucleotide sequence was modified to reduce the occurrence of destabilizing sequences. It was necessary to modify the wild type Bt polynucleotide sequence because the wild type full length Bt polynucleotide did not express sufficient levels of insecticidal protein in plants to be agronomically useful.

Heterologous genes are cloned into vectors suitable for plant transformation. Transformation and regeneration techniques useful to incorporate heterologous genes into a plant's genome are well known in the art. The gene can then be expressed in the plant cell to exhibit the added characteristic or trait. However, heterologous genes that normally express well as transgenes may experience gene silencing when more than one copy of the same genes are expressed in the same plant. This may occur when a first heterologous gene is too similar to an endogenous gene DNA sequence in the plant. Other examples include when a transgenic plant is subsequently crossed to other transgenic plants having the same or similar transgenes or when the transgenic plant is retransformed with a plant expression cassette that contains the same or is similar gene. Similarly, gene silencing may occur if trait stacking employs the same genetic elements used to direct expression of the transgene gene of interest. In order to stack traits, stable transgenic lines should be done with different combinations of genes and genetic elements to avoid gene silencing.

N-phosphonomethylglycine, also known as glyphosate, is a well-known herbicide that has activity on a broad spectrum of plant species. Glyphosate is the active ingredient of Roundup® (Monsanto Co.), a safe herbicide having a desirably short half-life in the environment. When applied to a plant surface, glyphosate moves systemically through the plant. Glyphosate is phytotoxic due to its inhibition of the shikimic acid pathway, which provides a precursor for the synthesis of aromatic amino acids. Glyphosate inhibits the enzyme 5-enolpyruvyl-3-phosphoshikimate synthase (EPSPS).

Glyphosate tolerance can also be achieved by the expression of EPSPS variants that have lower affinity for glyphosate and therefore retain their catalytic activity in the presence of glyphosate (U.S. Pat. No. 5,633,435, herein incorporated by reference). Enzymes that degrade glyphosate in plant tissues (U.S. Pat. No. 5,463,175) are also capable of conferring cellular tolerance to glyphosate. Such genes are used for the production of transgenic crops that are tolerant to glyphosate, thereby allowing glyphosate to be used for effective weed control with minimal concern of crop damage. For example, glyphosate tolerance has been genetically engineered into corn (U.S. Pat. No. 5,554,798), wheat (U.S. Patent Application No. 20020062503), soybean (U.S. Patent Application No. 20020157139) and canola (WO 9204449), all of which are incorporated by reference. The transgenes for glyphosate tolerance and the transgenes for tolerance to other herbicides, e.g. bar gene, (Toki et al. Plant Physiol., 100:1503-1507, 1992; Thompson et al. EMBO J. 6:2519-2523, 1987, phosphinothricin acetyltransferase, BAR gene isolated from *Streptomyces*; DeBlock et al. EMBO J., 6:2513-2522, 1987, glufosinate herbicide) are also useful as selectable markers or scorable markers and can provide a useful phenotype for selection of plants linked with other agronomically useful traits.

What is needed in the art are methods to design genes for expression in plants to improve agronomically useful traits that avoid gene silencing when multiple copies are inserted and recombination with endogenous plant genes.

BRIEF DESCRIPTION OF THE DRAWINGS

FIG. 1. Pileup comparison of the polynucleotide sequences changes of two artificial rice EPSPS versions (OsEPSPS_AT (SEQ ID NO:3), OsEPSPS_ZM (SEQ ID NO:4)) and a native rice EPSPS (OsEPSPS_Nat (SEQ ID NO:2)) the polypeptide of each modified to be glyphosate resistant.

FIG. 2. Pileup comparison of the polynucleotide sequences of a native (ZmEPSPS_Nat (SEQ ID NO:9)) and an artificial corn EPSPS (ZmEPSPS_ZM (SEQ ID NO:10)) the polypeptide of each modified to be glyphosate resistant.

FIG. 3. Pileup comparison of the polynucleotide sequences of a soybean native EPSPS (GmEPSPS_Nat (SEQ ID NO:6)) and artificial version (GmEPSPS_GM (SEQ ID NO:7)) the polypeptide of each modified to be glyphosate resistant.

FIG. 4. Pileup comparison of the polynucleotide sequences of a native BAR gene (BAR1_Nat (SEQ ID NO:20)) and two artificial versions with *Zea mays* (BAR1_ZM (SEQ ID NO:22)) and *Arabidopsis thaliana* (BAR1_AT (SEQ ID NO:21)) codon bias.

FIG. 5. Pileup comparison of the polynucleotide sequences of CTP2 and CP4EPSPS native (CTP2CP4_Nat (SEQ ID NO:36) and artificial versions (CTP2CP4_AT (SEQ ID 0:37), CTP2CP4_ZM (SEQ ID NO:38), and CTP2CP4_GM (SEQ ID NO:35)).

Figure 6:
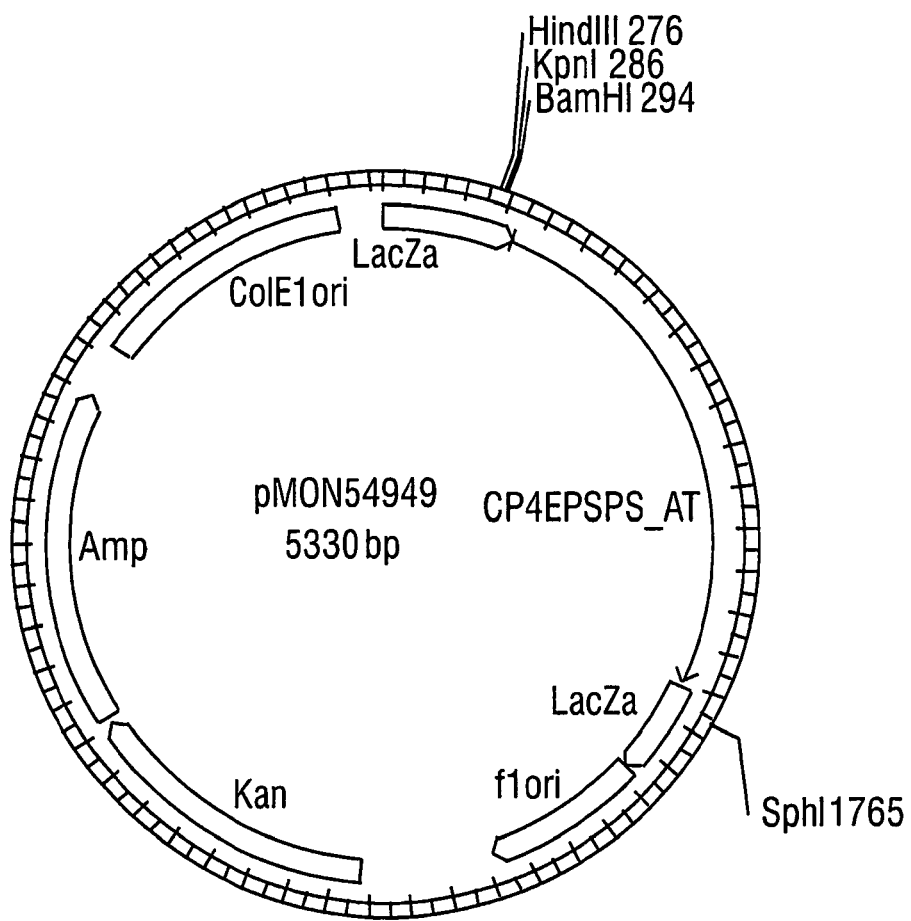
FIG. 6. Plasmid map of pMON54949.

| BRIEF DESCRIPTION OF SEQUENCE LISTING | | |
|---|---|---|
| SEQ ID NO: 1 | OsEPSPS_TIPS | A rice EPSPS protein sequence modified to be glyphosate resistant, with chloroplast transit peptide. |
| SEQ ID NO: 2 | OsEPSPS_Nat | Polynucleotide sequence of a rice native EPSPS polynucleotide modified to encode a glyphosate resistant protein. |
| SEQ ID NO: 3 | OsEPSPS_AT | Polynucleotide sequence of an artificial rice EPSPS polynucleotide using the *Arabidopsis* codon usage table and the methods of the present invention, and further modified to encode a glyphosate resistant protein. |
| SEQ ID NO: 4 | OsEPSPS_ZM | Polynucleotide sequence of an artificial rice EPSPS polynucleotide using the *Zea mays* codon usage table and the methods of the present invention, and further modified to encode a glyphosate resistant protein. |
| SEQ ID NO: 5 | GmEPSPS_IKS | A soybean EPSPS protein sequence modified to be glyphosate resistant, with chloroplast transit peptide. |
| SEQ ID NO: 6 | GmEPSPS_Nat | Polynucleotide sequence of a soybean native EPSPS polynucleotide modified to encode a glyphosate resistant protein. |
| SEQ ID NO: 7 | GmEPSPS_GM | Polynucleotide sequence of an artificial soybean EPSPS polynucleotide using the *Glycine max* codon usage table and the methods of the present invention, and further modified to encode a glyphosate resistant protein. |
| SEQ ID NO: 8 | ZmEPSPS_TIPS | A corn EPSPS protein sequence modified to be glyphosate resistant, with chloroplast transit peptide. |
| SEQ ID NO: 9 | ZmEPSPS_Nat | Polynucleotide sequence of a corn native EPSPS polynucleotide modified to encode a glyphosate resistant protein. |
| SEQ ID NO: 10 | ZmEPSPS_ZM | Polynucleotide sequence of an artificial corn EPSPS polynucleotide using the *Zea mays* codon usage table and the methods of the present invention, and further modified to encode a glyphosate resistant protein. |
| SEQ ID NO: 11 | CTP2 | Protein sequence of the chloroplast transit peptide 2 from *Arabidopsis* EPSPS gene. |
| SEQ ID NO: 12 | CTP2_Nat | Polynucleotide sequence of the chloroplast transit peptide from *Arabidopsis* EPSPS. |
| SEQ ID NO: 13 | CTP2_AT | Polynucleotide sequence of an artificial polynucleotide encoding the CTP2 using the *Arabidopsis* codon usage table and the methods of the present invention. |
| SEQ ID NO: 14 | CTP2_ZM | Polynucleotide sequence of an artificial polynucleotide encoding the CTP2 using the *Zea mays* codon usage table and the methods of the present invention. |

| BRIEF DESCRIPTION OF SEQUENCE LISTING | | |
|---|---|---|
| SEQ ID NO: 15 | CP4EPSPS | The protein sequence of the glyphosate resistant EPSPS protein from *Agrobacterium* strain CP4. |
| SEQ ID NO: 16 | CP4EPSPS_Nat | Polynucleotide sequence of the native polynucleotide encoding the CP4EPSPS protein (U.S. Pat. No. 5,633,435). |
| SEQ ID NO: 17 | CP4EPSPS_AT | Polynucleotide sequence of an artificial polynucleotide encoding the CP4EPSPS protein using the *Arabidopsis* codon usage table and the methods of the present invention. |
| SEQ ID NO: 18 | CP4EPSPS_ZM | Polynucleotide sequence of an artificial polynucleotide encoding the CP4EPSPS protein using the *Zea mays* codon usage table and the methods of the present invention. |
| SEQ ID NO: 19 | BAR1 | The protein sequence of a phosphinothricin acetyltransferase. |
| SEQ ID NO: 20 | BAR1_Nat | Polynucleotide sequence of the native polynucleotide isolated from *Streptomyces* encoding the phosphinothricin acetyltransferase. |
| SEQ ID NO: 21 | BAR1_AT | Polynucleotide sequence of an artificial polynucleotide encoding the phosphinothricin acetyltransferase using the *Arabidopsis* codon usage table and the methods of the present invention. |
| SEQ ID NO: 22 | BAR1_ZM | Polynucleotide sequence of an artificial polynucleotide encoding the phosphinothricin acetyltransferase using the *Zea mays* codon usage table and the methods of the present invention. |
| SEQ ID NO: 23 | CP4EPSPS_Syn | Polynucleotide sequence of an artificial polynucleotide with dicot codon bias. |
| SEQ ID NO: 24 | CP4EPSPS_AT_p1 | DNA primer molecule diagnostic for the CP4EPSPS_AT polynucleotide. |
| SEQ ID NO: 25 | CP4EPSPS_AT_p2 | DNA primer molecule diagnostic for the CP4EPSPS_AT polynucleotide. |
| SEQ ID NO: 26 | CP4EPSPS_ZM_p1 | DNA primer molecule diagnostic for the CP4EPSPS_ZM polynucleotide. |
| SEQ ID NO: 27 | CP4EPSPS_ZM_p2 | DNA primer molecule diagnostic for the CP4EPSPS_ZM polynucleotide. |
| SEQ ID NO: 28 | CP4EPSPS_Nat_p1 | DNA primer molecule diagnostic for the CP4EPSPS_Nat polynucleotide. |
| SEQ ID NO: 29 | CP4EPSPS_Nat_p2 | DNA primer molecule diagnostic for the CP4EPSPS_Nat polynucleotide. |
| SEQ ID NO: 30 | CP4EPSPS_Syn_p1 | DNA primer molecule diagnostic for the CP4EPSPS_Syn polynucleotide. |
| SEQ ID NO: 31 | CP4EPSPS_Syn_p2 | DNA primer molecule diagnostic for the CP4EPSPS_Syn polynucleotide. |
| SEQ ID NO: 32 | ZmAdh1 primer1 | Control primer 1 diagnostic for endogenous corn Adh1 gene. |
| SEQ ID NO: 33 | ZmAdh1 primer2 | Control primer 2 diagnostic for endogenous corn Adh1 gene. |
| SEQ ID NO: 34 | GNAGIAMKS | Motif providing glyphosate resistance to a plant EPSPS. |
| SEQ ID NO: 35 | CTPEPSPSCP4_GM | Polynucleotide sequence of an artificial polynucleotide encoding the CP4EPSPS protein using the *Glycine max* codon usage table. |

SUMMARY OF THE INVENTION

The present invention provides methods and compositions to design an artificial polynucleotide sequence that encodes a protein of interest, wherein the artificial polynucleotide is substantially divergent from a polynucleotide naturally occurring in a plant or a polynucleotide that has been introduced as a transgene into a plant and the artificial polynucleotide and polynucleotide encode a substantially identical polypeptide.

The artificial polynucleotides of the present invention that encodes proteins that provide agronomically useful phenotypes to a transgenic plant containing a DNA construct comprising the artificial polynucleotide. The agronomically useful phenotypes include, but are not limited to: drought tolerance, increased yield, cold tolerance, disease resistance, insect resistance and herbicide tolerance.

Another aspect of the present invention are artificial polynucleotides that encode a herbicide resistant EPSPS protein, a phosphinothricin acetyltransferase protein, a chloroplast transit peptide protein. In preferred embodiments of the present invention, the artificial polynucleotide molecule is selected from the group consisting of SEQ ID NO:3, SEQ ID NO:4, SEQ ID NO:6, SEQ ID NO:7, SEQ ID NO:10, SEQ ID NO:13, SEQ ID NO:14, SEQ ID NO:17, SEQ ID NO:18, SEQ ID NO:21, SEQ ID NO:22, and SEQ ID NO:35.

The present invention provides DNA constructs comprising: a promoter molecule that functions in plants, operably linked to an artificial polynucleotide molecule of the present invention, wherein the artificial polynucleotide molecule is selected from the group consisting of SEQ ID NO:3, SEQ ID NO:4, SEQ ID NO:6, SEQ ID NO:7, SEQ ID NO:10, SEQ ID NO:13, SEQ ID NO:14, SEQ ID NO:17, SEQ ID NO:18, SEQ ID NO:21, SEQ ID NO:22, and SEQ ID NO:35, operably linked to a transcription termination region.

The present invention further provides DNA constructs comprising: a promoter molecule that functions in plants, operably linked to an artificial polynucleotide molecule that encodes a chloroplast transit peptide, operably linked to a heterologous glyphosate resistant EPSPS, operably linked to a transcription termination signal region, wherein the artificial polynucleotide is substantially divergent in polynucleotide sequence from known polynucleotides encoding an identical chloroplast transit peptide.

The present invention provides DNA constructs comprising at least two expression cassettes, the first expression cassette comprising a promoter molecule that functions in plants, operably linked to an artificial polynucleotide molecule of the present invention, operably linked to a transcription termination signal region, and the second expression cassette comprising a promoter molecule that functions in plants, operably linked to a polynucleotide molecule that encodes a substantially identical polypeptide as said artificial polynucleotide and is less than eight-five percent similar in polynucleotide sequence to said artificial polynucleotide, operably linked to a transcription termination signal region.

The present invention provides plant cells, plants or progeny thereof comprising a DNA construct of the present invention. Of particular interest are plants of progeny thereof selected from the group consisting of wheat, corn, rice, soybean, cotton, potato, canola, turf grass, forest trees, grain sorghum, vegetable crops, ornamental plants, forage crops, and fruit crops.

A method of the present invention reduces gene silencing during breeding of transgenic plants comprising the steps of:
a) constructing an artificial polynucleotide that is substantially divergent from known polynucleotides that encode a substantially identical protein, and
b) constructing a DNA construct containing said artificial polynucleotide molecule; and
c) transforming said DNA construct into a plant cell; and
d) regenerating said plant cell into a transgenic plant; and
e) crossing said transgenic plant with a fertile plant, wherein said fertile plant contains a polynucleotide molecule that encodes a protein substantially identical to a protein encoded by said artificial polynucleotide molecule and wherein said artificial polynucleotide molecule and said polynucleotide molecule are substantially divergent.

Another aspect of the invention is a transgenic plant cell comprising two polynucleotides, wherein at least one of the polynucleotides is a transgene and the two polynucleotides encode a substantially identical protein and are less than eight-five percent similar in polynucleotide sequence.

Another aspect of the present invention in a method to reduce gene silencing during production of transgenic plants comprises the steps of:
a) constructing an artificial polynucleotide that is substantially divergent from known polynucleotides that encode a substantially identical protein, and
b) constructing a first DNA construct containing said artificial polynucleotide molecule; and
c) transforming said DNA construct into a plant cell; and
d) regenerating said plant cell into a transgenic plant; and
e) retransforming a cell from said transgenic plant with a second DNA construct comprising a polynucleotide molecule that encodes a substantially identical protein to said artificial polynucleotide and said polynucleotide and artificial polynucleotide are substantially divergent in polynucleotide sequence; and
f) regenerating said cell of step d into a transgenic plant comprising both said artificial polynucleotide and said polynucleotide.

Further provided by the present invention are methods for selection of a plants transformed with a DNA construct of the invention comprising the steps of:
a) transforming a plant cell with a DNA construct of the present invention; and
b) culturing said plant cell in a selective medium containing a herbicide selected from the group consisting of: glyphosate and glufosinate, to selectively kill cells which have not been transformed with said DNA constructs; and
c) regenerating said plant cell into a fertile plant.

Another aspect of the invention is a method of detecting an artificial polynucleotide in a transgenic plant cell, plant or progeny thereof comprising the steps:
a) contacting a DNA sample isolated from said plant cell, plant or progeny thereof with a DNA molecule, wherein said DNA molecule comprises at least one DNA molecule of a pair of DNA molecules that when used in a nucleic-acid amplification reaction produces an amplicon that is diagnostic for said artificial polynucleotide molecule selected from the group consisting of: SEQ ID NO:3, SEQ ID NO:4, SEQ ID NO:6, SEQ ID NO:7, SEQ ID NO:10, SEQ ID NO:13, SEQ ID NO:14, SEQ ID NO:17, SEQ ID NO:18, SEQ ID NO:21, SEQ ID NO:22, and SEQ ED NO:35.
(a) performing a nucleic acid amplification reaction, thereby producing the amplicon; and
(b) detecting the amplicon.

Reagents provided for performing the detection method above include, but are not limited to: DNA molecules that specifically hybridize to an artificial polynucleotide molecule selected from the group consisting of: SEQ ID NO:3, SEQ ID NO:4, SEQ ID NO:6, SEQ ID NO:7, SEQ ID NO:10, SEQ ID NO:13, SEQ ID NO:14, SEQ ID NO:17, SEQ ID NO:18, SEQ ID NO:21, and SEQ ID NO:22; and isolated DNA molecules selected from the group consisting of: SEQ ID NO:24, SEQ ID NO:25, SEQ ID NO:26, and SEQ ID NO:27.

The present invention provides plants, and progeny comprising a DNA molecule selected from the group consisting of: SEQ ID NO:3, SEQ ID NO:4, SEQ ID NO:6, SEQ ID NO:7, SEQ ID NO:10, SEQ ID NO:13, SEQ ID NO:14, SEQ ID NO:17, SEQ ID NO:18, SEQ ID NO:21 SEQ ID NO:22, SEQ ID NO:24, SEQ ID NO:25, SEQ ID NO:26, and SEQ ID NO:27.

The present invention provides pairs of DNA molecules selected from the group comprising: a first DNA molecule and a second DNA molecule, wherein the first DNA molecule is SEQ ID NO:24 or its complement and the second DNA molecule is SEQ ID NO:25 or its complement and the pair of DNA molecules when used in a DNA amplification method produce an amplicon, and a first DNA molecule and a second DNA molecule, wherein the first DNA molecule is SEQ ID NO:26 or its complement and the second DNA molecule is SEQ ID NO:27 or its complement and the pair of DNA molecules when used in a DNA amplification method produce an amplicon, wherein the amplicon is diagnostic for the presence of an artificial polynucleotide of the present invention in the genome of a transgenic plant.

The present invention provides for a plant and progeny thereof identified by a DNA amplification method to contain in its genome a DNA molecule selected from the group consisting of: SEQ ID NO:3, SEQ ID NO:4, SEQ ID NO:6, SEQ ID NO:7, SEQ ID NO:10, SEQ ID NO:13, SEQ ID NO:14, SEQ ID NO:17, SEQ ID NO:18, SEQ ID NO:21 SEQ ID NO:22, SEQ ID NO:24, SEQ ID NO:25, SEQ ID NO:26, and SEQ ID NO:27.

The present invention provides and contemplates DNA detection kits comprising: at least one DNA molecule of sufficient length to be specifically homologous or complementary to an artificial polynucleotide selected from the group consisting of SEQ ID NO:3, SEQ ID NO:4, SEQ ID NO:6, SEQ ID NO:7, SEQ ID NO:10, SEQ ID NO:13, SEQ ID NO:14, SEQ ID NO:17, SEQ ID NO:18, SEQ ID NO:21, and SEQ ID NO:22, wherein said DNA molecule is useful as a DNA probe or DNA primer; or at least one DNA molecule homologous or complementary to a DNA primer molecule selected from the group consisting of: SEQ ID NO:24, SEQ ID NO:25, SEQ ID NO:26, and SEQ ID NO:27.

The present invention further provides a method of detecting the presence of an artificial polynucleotide encoding a glyphosate resistant EPSPS in a DNA sample, the method comprising:

(a) extracting a DNA sample from a plant; and
(b) contacting the DNA sample with a labeled DNA molecule of sufficient length to be specifically homologous or complementary to an artificial polynucleotide selected from the group consisting of: SEQ ID NO:3, SEQ ID NO:4, SEQ ID NO:6, SEQ ID NO:7, SEQ ID NO:10, SEQ ID NO:13, SEQ ID NO:14, SEQ ID NO:17, and SEQ ID NO:18, wherein said labeled DNA molecule is a DNA probe; and
(c) subjecting the sample and DNA probe to stringent hybridization conditions; and
(d) detecting the DNA probe hybridized to the DNA sample.

The present invention provides for an isolated polynucleotide that encodes an EPSPS enzyme, the EPSPS enzyme contains the motif of SEQ ID NO:34. The present invention provides for a DNA construct containing a polynucleotide that encodes for the EPSPS enzyme with the motif of SEQ ID NO:34. A plant cell, plant or progeny thereof that is tolerant to glyphosate as a result of expressing an EPSPS enzyme that contains the motif of SEQ ID NO:34 is an aspect of the invention.

DETAILED DESCRIPTION OF THE INVENTION

The following definitions are provided to better define the present invention and to guide those of ordinary skill in the art in the practice of the present invention. Unless otherwise noted, terms are to be understood according to conventional usage by those of ordinary skill in the relevant art. Definitions of common terms in molecular biology may also be found in Rieger et al., Glossary of Genetics: Classical and Molecular, 5th edition, Springer-Verlag: New York, (1991); and Lewin, Genes V, Oxford University Press: New York, (1994). The nomenclature for DNA bases as set forth at 37 CFR §1.822 is used. The standard one- and three-letter nomenclature for amino acid residues is used.

"Amino-acid substitutions", "Amino-acid variants", are preferably substitutions of single amino-acid residue for another amino-acid residue at any position within the protein. Substitutions, deletions, insertions or any combination thereof can be combined to arrive at a final construct.

An "artificial polynucleotide" as used in the present invention is a DNA sequence designed according to the methods of the present invention and created as an isolated DNA molecule for use in a DNA construct that provides expression of a protein in host cells, and for the purposes of cloning into appropriate constructs or other uses known to those skilled in the art. Computer programs are available for these purposes, including but not limited to the "BestFit" or "Gap" programs of the Sequence Analysis Software Package, Genetics Computer Group (GCG), Inc., University of Wisconsin Biotechnology Center, Madison, Wis. 53711. The artificial polynucleotide may be created by a one or more methods known in the art, that include, but are not limited to: overlapping PCR. An artificial polynucleotide of the present invention is substantially divergent from other polynucleotides that code for the identical or nearly identical protein.

The term "chimeric" refers to a fusion nucleic acid or protein sequence. A chimeric nucleic acid coding sequence is comprised of two or more sequences joined in-frame that encode a chimeric protein. A chimeric gene refers to the multiple genetic elements derived from heterologous sources comprising a gene.

The phrases "coding sequence", "open reading frame", and "structural sequence" refer to the region of continuous sequential nucleic acid triplets encoding a protein, polypeptide, or peptide sequence.

"Codon" refers to a sequence of three nucleotides that specify a particular amino acid.

"Codon usage" or "codon bias" refers to the frequency of use of codons encoding amino acids in the coding sequences of organisms.

"Complementarity" and "complement" when referring to nucleic acid sequences, refers to the specific binding of adenine to thymine (uracil in RNA) and cytosine to guanine on opposite strands of DNA or RNA.

"Construct" refers to the heterologous genetic elements operably linked to each other making up a recombinant DNA molecule and may comprise elements that provide expression of a DNA polynucleotide molecule in a host cell and elements that provide maintenance of the construct.

"C-terminal region" refers to the region of a peptide, polypeptide, or protein chain from the middle thereof to the end that carries the amino acid having a free carboxyl group.

The term "divergent", as used herein, refers to the comparison of polynucleotide molecules that encode the same or nearly the same protein or polypeptide. The four letter genetic code (A, G, C, and T/U) comprises three letter codons that direct t-RNA molecules to assemble amino acids into a polypeptide from an mRNA template. Having more than one codon that may code for the same amino acid is referred to as degenerate. Degenerate codons are used to construct substantially divergent polynucleotide molecules that encode the same polypeptide where these molecules have a sequence of nucleotides of their entire length in which they are less than 85% identical, and there are no lengths of polynucleotide sequence greater than 23 nucleotides that are identical.

The term "encoding DNA" refers to chromosomal DNA, plasmid DNA, cDNA, or artificial DNA polynucleotide that encodes any of the proteins discussed herein.

The term "endogenous" refers to materials originating from within an organism or cell.

"Endonuclease" refers to an enzyme that hydrolyzes double stranded DNA at internal locations.

"Exogenous" refers to materials originating from outside of an organism or cell. This typically applies to nucleic acid molecules used in producing transformed or transgenic host cells and plants.

"Exon" refers to the portion of a gene that is actually translated into protein, i.e., a coding sequence.

The term "expression" refers to the transcription or translation of a polynucleotide to produce a corresponding gene product, a RNA or protein.

"Fragments". A fragment of a gene is a portion of a full-length polynucleic acid molecule that is of at least a minimum length capable of transcription into a RNA, translation into a peptide, or useful as a probe or primer in a DNA detection method.

The term "gene" refers to chromosomal DNA, plasmid DNA, cDNA, artificial DNA polynucleotide, or other DNA that encodes a peptide, polypeptide, protein, or RNA molecule, and the genetic elements flanking the coding sequence that are involved in the regulation of expression.

The term "genome" as it applies to viruses encompasses all of the nucleic acid sequence contained within the capsid of the virus. The term "genome" as it applies to bacteria encompasses both the chromosome and plasmids within a bacterial host cell. Encoding nucleic acids of the present invention introduced into bacterial host cells can therefore be either chromosomally-integrated or plasmid-localized. The term "genome" as it applies to plant cells encompasses not only chromosomal DNA found within the nucleus, but organelle DNA found within subcellular components of the cell. Nucleic acids of the present invention introduced into plant cells can therefore be either chromosomally-integrated or organelle-localized.

"Glyphosate" refers to N-phosphonomethylglycine and its' salts, Glyphosate is the active ingredient of Roundup® herbicide (Monsanto Co.). Plant treatments with "glyphosate" refer to treatments with the Roundup® or Roundup Ultra® herbicide formulation, unless otherwise stated. Glyphosate as N-phosphonomethylglycine and its' salts (not formulated Roundup® herbicide) are components of synthetic culture media used for the selection of bacteria and plant tolerance to glyphosate or used to determine enzyme resistance in in vitro biochemical assays.

"Heterologous DNA" sequence refers to a polynucleotide sequence that originates from a foreign source or species or, if from the same source, is modified from its original form.

"Homologous DNA" refers to DNA from the same source as that of the recipient cell.

"Hybridization" refers to the ability of a strand of nucleic acid to join with a complementary strand via base pairing. Hybridization occurs when complementary sequences in the two nucleic acid strands bind to one another. The nucleic acid probes and primers of the present invention hybridize under stringent conditions to a target DNA sequence. Any conventional nucleic acid hybridization or amplification method can be used to identify the presence of DNA from a transgenic event in a sample. Nucleic acid molecules or fragments thereof are capable of specifically hybridizing to other nucleic acid molecules under certain circumstances. As used herein, two nucleic acid molecules are said to be capable of specifically hybridizing to one another if the two molecules are capable of forming an anti-parallel, double-stranded nucleic acid structure. A nucleic acid molecule is said to be the "complement" of another nucleic acid molecule if they exhibit complete complementarity. As used herein, molecules are said to exhibit "complete complementarity" when every nucleotide of one of the molecules is complementary to a nucleotide of the other. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Conventional stringency conditions are described by Sambrook et al., 1989, and by Haymes et al., In: *Nucleic Acid Hybridization, A Practical Approach*, IRL Press, Washington, D.C. (1985), herein incorporated by reference in its entirety. Departures from complete complementarity are therefore permissible, as long as such departures do not completely preclude the capacity of the molecules to form a double-stranded structure. In order for a nucleic acid molecule to serve as a primer or probe it need only be sufficiently complementary in sequence to be able to form a stable double-stranded structure under the particular solvent and salt concentrations employed.

As used herein, a substantially homologous sequence is a nucleic acid sequence that will specifically hybridize to the complement of the nucleic acid sequence to which it is being compared under high stringency conditions. The term "stringent conditions" is functionally defined with regard to the hybridization of a nucleic-acid probe to a target nucleic acid (i.e., to a particular nucleic-acid sequence of interest) by the specific hybridization procedure discussed in Sambrook et al., 1989, at 9.52-9.55. See also, Sambrook et al., 1989 at 9.47-9.52, 9.56-9.58 herein incorporated by reference in its entirety; Kanehisa, (Nucl. Acids Res. 12:203-213, 1984, herein incorporated by reference in its entirety); and Wetmur and Davidson, (J. Mol. Biol. 31:349-370, 1988, herein incorporated by reference in its entirety). Accordingly, the nucleotide sequences of the invention may be used for their ability to selectively form duplex molecules with complementary stretches of DNA fragments. Depending on the application envisioned, one will desire to employ varying conditions of hybridization to achieve varying degrees of selectivity of probe towards target sequence. For applications requiring high selectivity, one will typically desire to employ relatively stringent conditions to form the hybrids, e.g., one will select relatively low salt and/or high temperature conditions, such as provided by about 0.02 M to about 0.15 M NaCl at temperatures of about 50° C. to about 70° C. A stringent conditions, for example, is to wash the hybridization filter at least twice with high-stringency wash buffer (0.2×SSC, 0.1% SDS, 65° C.). Appropriate stringency conditions which promote DNA hybridization, for example, 6.0× sodium chloride/sodium citrate (SSC) at about 45° C., followed by a wash of 2.0×SSC at 50° C., are known to those skilled in the art or can be found in *Current Protocols in Molecular Biology*, John Wiley & Sons, N.Y. (1989), 6.3.1-6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed. Such selective conditions tolerate little, if any, mismatch between the probe and the template or target strand. Detection of DNA sequences via hybridization is well-known to those of skill in the art, and the teachings of U.S. Pat. Nos. 4,965,188 and 5,176,995 are exemplary of the methods of hybridization analyses.

"Identity" refers to the degree of similarity between two polynucleic acid or protein sequences. An alignment of the two sequences is performed by a suitable computer program. A widely used and accepted computer program for performing sequence alignments is CLUSTALW v1.6 (Thompson, et al. Nucl. Acids Res., 22: 4673-4680, 1994). The number of matching bases or amino acids is divided by the total number of bases or amino acids, and multiplied by 100 to obtain a percent identity. For example, if two 580 base pair sequences had 145 matched bases, they would be 25 percent identical. If the two compared sequences are of different lengths, the number of matches is divided by the shorter of the two lengths. For example, if there are 100 matched amino acids between a 200 and a 400 amino acid protein, they are 50 percent identical with respect to the shorter sequence. If the shorter sequence is less than 150 bases or 50 amino acids in length, the number of matches are divided by 150 (for nucleic acid bases) or 50 (for amino acids), and multiplied by 100 to obtain a percent identity.

As described herein a protein can be "substantially identical" to related proteins. These proteins with substantial identity generally comprise at least one polypeptide sequence that has at least ninety-eight sequence percent identity compared to its related other polypeptide sequence. The Gap program in the WISCONSIN PACKAGE version 10.0-UNIX from Genetics Computer Group, Inc. is based on the method of Needleman and Wunsch (J. Mol. Biol. 48:443-453, 1970) using the set of default parameters for pairwise comparison (for amino acid sequence comparison: Gap Creation Penalty=8, Gap Extension Penalty=20); or using the TBLASTN program in the BLAST 2.2.1 software suite (Altschul et al., Nucleic Acids Res. 25:3389-3402), using BLOSUM62 matrix (Henikoff and Henikoff, Proc. Natl. Acad. Sci. U.S.A. 89:10915-10919, 1992) and the set of default parameters for pair-wise comparison (gap creation cost=11, gap extension cost=1). In BLAST, the E-value, or expectation value, represents the number of different alignments with scores equivalent to or better than the raw alignment score, S, that are expected to occur in a database search by chance. The lower the E value, the more significant the match. Because database size is an element in E-value calculations, E-values obtained by "BLASTing" against public databases, such as GenBank, have generally increased over time for any given query/entry match. Percent identity refers to the percentage of identically matched amino acid residues that exist along the length of that portion of the sequences which is aligned by the BLAST algorithm.

"Intron" refers to a portion of a gene not translated into protein, even though it is transcribed into RNA.

An "isolated" nucleic acid sequence is substantially separated or purified away from other nucleic acid sequences with which the nucleic acid is normally associated in the cell of the organism in which the nucleic acid naturally occurs, i.e., other chromosomal or extrachromosomal DNA. The term embraces nucleic acids that are biochemically purified so as to substantially remove contaminating nucleic acids and other cellular components. The term also embraces recombinant nucleic acids and chemically synthesized nucleic acids.

"Isolated," "Purified," "Homogeneous" polypeptides. A polypeptide is "isolated" if it has been separated from the cellular components (nucleic acids, lipids, carbohydrates, and other polypeptides) that naturally accompany it or that is chemically synthesized or recombinant. A monomeric polypeptide is isolated when at least 60% by weight of a sample is composed of the polypeptide, preferably 90% or more, more preferably 95% or more, and most preferably more than 99%. Protein purity or homogeneity is indicated, for example, by polyacrylamide gel electrophoresis of a protein sample, followed by visualization of a single polypeptide band upon staining the polyacrylamide gel; high pressure liquid chromatography; or other conventional methods. Proteins can be purified by any of the means known in the art, for example as described in *Guide to Protein Purification*, ed. Deutscher, Meth. Enzymol. 185, Academic Press, San Diego, 1990; and *Scopes, Protein Purification: Principles and Practice*, Springer Verlag, New York, 1982.

"Labeling" or "labeled". There are a variety of conventional methods and reagents for labeling polynucleotides and polypeptides and fragments thereof. Typical labels include radioactive isotopes, ligands or ligand receptors, fluorophores, chemiluminescent agents, and enzymes. Methods for labeling and guidance in the choice of labels appropriate for various purposes are discussed, e.g., in Sambrook et al., *Molecular Cloning: A Laboratory Manual*, Cold Spring Harbor Press (1989) and *Current Protocols in Molecular Biology*, ed. Ausubel et al., Greene Publishing and Wiley-Interscience, New York, (1992).

"Mature protein coding region", this term refers to the sequence of a processed protein product, i.e., a mature EPSP synthase remaining after the chloroplast transit peptide has been removed.

"Native", the term "native" generally refers to a naturally-occurring ("wild-type") polynucleic acid or polypeptide. However, in the context of the present invention, some modification of an isolated polynucleotide and polypeptide may have occurred to provide a polypeptide with a particular phenotype, e.g., amino acid substitution in glyphosate sensitive EPSPS to provide a glyphosate resistant EPSPS. For comparative purposes in the present invention, the isolated polynucleotide that contains a few substituted nucleotides to provide amino acid modification for herbicide tolerance is referred to as the "native" polynucleotide when compared to the substantially divergent polynucleotide created by the methods of the present invention. However, the "native" polynucleotide modified in this manner is normative with respect to the genetic elements normally found linked to a naturally occurring unmodified polynucleotide.

"N-terminal region" refers to a region of a peptide, polypeptide, or protein chain from the amino acid having a free amino group to the middle of the chain.

"Nucleic acid" refers to deoxyribonucleic acid (DNA) and ribonucleic acid (RNA).

Nucleic acid codes: A=adenosine; C=cytosine; G=guanosine; T=thymidine. Codes used for synthesis of oligonucleotides: N=equimolar A, C, G, and T; I=deoxyinosine; K=equimolar G and T; R=equimolar A and G; S=equimolar C and G; W=equimolar A and T; Y=equimolar C and T.

A "nucleic acid segment" or a "nucleic acid molecule segment" is a nucleic acid molecule that has been isolated free of total genomic DNA of a particular species, or that has been synthesized. Included with the term "nucleic acid segment" are DNA segments, recombinant vectors, plasmids, cosmids, phagemids, phage, viruses, et cetera.

"Nucleotide Sequence Variants", using well-known methods, the skilled artisan can readily produce nucleotide and amino acid sequence variants of genes and proteins, respectively. For example, "variant" DNA molecules of the present invention are DNA molecules containing changes in an EPSPS gene sequence, i.e., changes that include one or more nucleotides of the EPSPS gene sequence are deleted, added, and/or substituted, such that the variant EPSPS gene encodes a protein that retains EPSPS activity. Variant DNA molecules can be produced, for example, by standard DNA mutagenesis techniques or by chemically synthesizing the variant DNA molecule or a portion thereof. Methods for chemical synthesis of nucleic acids are discussed, for example, in Beaucage et al., Tetra. Letts. 22:1859-1862 (1981), and Matteucci et al., J. Am. Chem. Soc. 103:3185- (1981). Chemical synthesis of nucleic acids can be performed, for example, on automated oligonucleotide synthesizers. Such variants preferably do not change the reading frame of the protein-coding region of the nucleic acid and preferably encode a protein having no change, or only a minor reduction.

"Open reading frame (ORF)" refers to a region of DNA or RNA encoding a peptide, polypeptide, or protein.

"Operably Linked". A first nucleic-acid sequence is "operably" linked with a second nucleic-acid sequence when the first nucleic-acid sequence is placed in a functional relationship with the second nucleic-acid sequence. For example, a promoter is operably linked to a protein-coding sequence if the promoter effects the transcription or expression of the coding sequence. Generally, operably linked DNA sequences are contiguous and, where necessary to join two protein-coding regions, in reading frame.

"Overexpression" refers to the expression of a RNA or polypeptide or protein encoded by a DNA introduced into a host cell, wherein the RNA or polypeptide or protein is either not normally present in the host cell, or wherein the RNA or polypeptide or protein is present in said host cell at a higher level than that normally expressed from the endogenous gene encoding the RNA or polypeptide or protein.

The term "plant" encompasses any higher plant and progeny thereof, including monocots (e.g., corn, rice, wheat, barley, etc.), dicots (e.g., soybean, cotton, canola, tomato, potato, *Arabidopsis*, tobacco, etc.), gymnosperms (pines, firs, cedars, etc.) and includes parts of plants, including reproductive units of a plant (e.g., seeds, bulbs, tubers, fruit, flowers, etc.) or other parts or tissues from that the plant can be reproduced.

"Plant expression cassette" refers to chimeric DNA segments comprising the regulatory elements that are operably linked to provide the expression of a transgene product in plants "Plasmid" refers to a circular, extrachromosomal, self-replicating piece of DNA.

"Polyadenylation signal" or "polyA signal" refers to a nucleic acid sequence located 3' to a coding region that causes the addition of adenylate nucleotides to the 3' end of the mRNA transcribed from the coding region.

"Polymerase chain reaction (PCR)" refers to a DNA amplification method that uses an enzymatic technique to create multiple copies of one sequence of nucleic acid (amplicon). Copies of a DNA molecule are prepared by shuttling a DNA polymerase between two amplimers. The basis of this amplification method is multiple cycles of temperature changes to denature, then re-anneal amplimers (DNA primer molecules), followed by extension to synthesize new DNA strands in the region located between the flanking amplimers. Nucleic-acid amplification can be accomplished by any of the various nucleic-acid amplification methods known in the art, including the polymerase chain reaction (PCR). A variety of amplification methods are known in the art and are described, inter alfa, in U.S. Pat. Nos. 4,683,195 and 4,683,202 and in *PCR Protocols: A Guide to Methods and Applications*, ed. Innis et al., Academic Press, San Diego, 1990. PCR amplification methods have been developed to amplify up to 22 kb of genomic DNA and up to 42 kb of bacteriophage DNA (Cheng et al., Proc. Natl. Acad. Sci. USA 91:5695-5699, 1994). These methods as well as other methods known in the art of DNA amplification may be used in the practice of the present invention.

Polynucleotide refers to a length of deoxyribonucleic acid (DNA) and ribonucleic acid (RNA) molecules greater than two, which are connected to form a larger molecule.

Polypeptide fragments. The present invention also encompasses fragments of a protein that lacks at least one residue of a native full-length protein, but that substantially maintains activity of the protein.

The term "promoter" or "promoter region" refers to a polynucleic acid molecule that functions as a regulatory element, usually found upstream (5') to a coding sequence, that controls expression of the coding sequence by controlling production of messenger RNA (mRNA) by providing the recognition site for RNA polymerase and/or other factors necessary for start of transcription at the correct site. As contemplated herein, a promoter or promoter region includes variations of promoters derived by means of ligation to various regulatory sequences, random or controlled mutagenesis, and addition or duplication of enhancer sequences. The promoter region disclosed herein, and biologically functional equivalents thereof, are responsible for driving the transcription of coding sequences under their control when introduced into a host as part of a suitable recombinant vector, as demonstrated by its ability to produce mRNA.

"Recombinant". A "recombinant" nucleic acid is made by a combination of two otherwise separated segments of sequence, e.g., by chemical synthesis or by the manipulation of isolated segments of nucleic acids by genetic engineering techniques.

The term "recombinant DNA construct" or "recombinant vector" refers to any agent such as a plasmid, cosmid, virus, autonomously replicating sequence, phage, or linear or circular single-stranded or double-stranded DNA or RNA nucleotide sequence, derived from any source, capable of genomic integration or autonomous replication, comprising a DNA molecule that one or more DNA sequences have been linked in a functionally operative manner. Such recombinant DNA constructs or vectors are capable of introducing a 5' regulatory sequence or promoter region and a DNA sequence for a selected gene product into a cell in such a manner that the DNA sequence is transcribed into a functional mRNA that is translated and therefore expressed. Recombinant DNA constructs or recombinant vectors may be constructed to be capable of expressing antisense RNAs, in order to inhibit translation of a specific RNA of interest.

"Regeneration" refers to the process of growing a plant from a plant cell (e.g., plant protoplast or explant).

"Reporter" refers to a gene and corresponding gene product that when expressed in transgenic organisms produces a product detectable by chemical or molecular methods or produces an observable phenotype.

"Resistance" refers to an enzyme that is able to function in the presence of a toxin, for example, glyphosate resistant class II EPSP synthases. An enzyme that has resistance to a toxin may have the function of detoxifying the toxin, e.g., the phosphinothricin acetyltransferase, glyphosate oxidoreductase, or may be a mutant enzyme having catalytic activity which is unaffected by an herbicide which disrupts the same activity in the wild type enzyme, e.g., acetolactate synthase, mutant class I EPSP synthases.

"Restriction enzyme" refers to an enzyme that recognizes a specific palindromic sequence of nucleotides in double stranded DNA and cleaves both strands; also called a restriction endonuclease. Cleavage typically occurs within the restriction site.

"Selectable marker" refers to a polynucleic acid molecule that encodes a protein, which confers a phenotype facilitating identification of cells containing the polynucleic acid molecule. Selectable markers include those genes that confer resistance to antibiotics (e.g., ampicillin, kanamycin), complement a nutritional deficiency (e.g., uracil, histidine, leucine), or impart a visually distinguishing characteristic (e.g., color changes or fluorescence). Useful dominant selectable marker genes include genes encoding antibiotic resistance genes (e.g., neomycin phosphotransferase, aad); and herbicide resistance genes (e.g., phosphinothricin acetyltransferase, class II EPSP synthase, modified class I EPSP synthase). A useful strategy for selection of transformants for herbicide resistance is described, e.g., in Vasil, *Cell Culture and Somatic Cell Genetics of Plants*, Vols. I-III, Laboratory Procedures and Their Applications Academic Press, New York (1984).

The term "specific for (a target sequence)" indicates that a DNA probe or DNA primer hybridizes under given hybridization conditions only to the target sequence in a sample comprising the target sequence.

The term "substantially purified", as used herein, refers to a molecule separated from other molecules normally associated with it in its native state. More preferably, a substantially purified molecule is the predominant species present in a preparation. A substantially purified molecule may be greater than 60% free, preferably 75% free, more preferably 90% free from the other molecules (exclusive of solvent) present in the natural mixture. The term "substantially purified" is not intended to encompass molecules present in their native state.

"Tolerant" or "tolerance" refers to a reduced effect of a biotic or abiotic agent on the growth and development of organisms and plants, e.g. a pest or a herbicide.

"Transcription" refers to the process of producing an RNA copy from a DNA template.

"Transformation" refers to a process of introducing an exogenous polynucleic acid molecule (e.g., a DNA construct, a recombinant polynucleic acid molecule) into a cell or protoplast and that exogenous polynucleic acid molecule is incorporated into a chromosome or is capable of autonomous replication.

"Transformed" or "transgenic" refers to a cell, tissue, organ, or organism into which a foreign polynucleic acid, such as a DNA vector or recombinant polynucleic acid molecule. A "transgenic" or "transformed" cell or organism also includes progeny of the cell or organism and progeny produced from a breeding program employing such a "transgenic" plant as a parent in a cross and exhibiting an altered phenotype resulting from the presence of the foreign polynucleic acid molecule.

The term "transgene" refers to any polynucleic acid molecule normative to a cell or organism transformed into the cell or organism. "Transgene" also encompasses the component parts of a native plant gene modified by insertion of a normative polynucleic acid molecule by directed recombination or site specific mutation.

"Transit peptide" or "targeting peptide" molecules, these terms generally refer to peptide molecules that when linked to a protein of interest directs the protein to a particular tissue, cell, subcellular location, or cell organelle. Examples include, but are not limited to, chloroplast transit peptides, nuclear targeting signals, and vacuolar signals. The chloroplast transit peptide is of particular utility in the present invention to direct expression of the EPSPS enzyme to the chloroplast.

The term "translation" refers to the production the corresponding gene product, i.e., a peptide, polypeptide, or protein from a mRNA.

"Vector" refers to a plasmid, cosmid, bacteriophage, or virus that carries foreign DNA into a host organism.

Polynucleotides

Methods of the present invention include designing genes that confer a trait of interest to the plant into which they are introduced. The transgenes of agronomic interest that provide beneficial agronomic traits to crop plants, for example, including, but not limited to genetic elements comprising herbicide resistance (U.S. Pat. Nos. 5,633,435; 5,463,175), increased yield (U.S. Pat. No. 5,716,837), insect control (U.S. Pat. Nos. 6,063,597; 6,063,756; 6,093,695; 5,942,664; 6,110,464), fungal disease resistance (U.S. Pat. Nos. 5,516, 671; 5,773,696; 6,121,436; 6,316,407, and 6,506,962), virus resistance (U.S. Pat. Nos. 5,304,730 and 6,013,864), nematode resistance (U.S. Pat. No. 6,228,992), bacterial disease resistance (U.S. Pat. No. 5,516,671), starch production (U.S. Pat. Nos. 5,750,876 and 6,476,295), modified oils production (U.S. Pat. No. 6,444,876), high oil production (U.S. Pat. Nos. 5,608,149 and 6,476,295), modified fatty acid content (U.S. Pat. No. 6,537,750), high protein production (U.S. Pat. No. 6,380,466), fruit ripening (U.S. Pat. No. 5,512,466), enhanced animal and human nutrition (U.S. Pat. Nos. 5,985, 605 and 6,171,640), biopolymers (U.S. Pat. No. 5,958,745 and US Patent Publication No. US20030028917), environmental stress resistance (U.S. Pat. No. 6,072,103), pharmaceutical peptides (U.S. Pat. No. 6,080,560), improved processing traits (U.S. Pat. No. 6,476,295), improved digestibility (U.S. Pat. No. 6,531,648) low raffinose (U.S. Pat. No. 6,166,292), industrial enzyme production (U.S. Pat. No. 5,543,576), improved flavor (U.S. Pat. No. 6,011,199), nitrogen fixation (U.S. Pat. No. 5,229,114), hybrid seed production (U.S. Pat. No. 5,689,041), and biofuel production (U.S. Pat. No. 5,998,700), the genetic elements and transgenes described in the patents listed above are herein incorporated by reference.

Herbicides for which transgenic plant tolerance has been demonstrated and the method of the present invention can be applied, include but are not limited to: glyphosate, glufosinate, sulfonylureas, imidazolinones, bromoxynil, delapon, cyclohezanedione, protoporphyrionogen oxidase inhibitors, and isoxasflutole herbicides. Polynucleotide molecules encoding proteins involved in herbicide tolerance are known in the art, and include, but are not limited to a is polynucleotide molecule encoding 5-enolpyruvylshikimate-3-phosphate synthase (EPSPS, described in U.S. Pat. Nos. 5,627, 061, 5,633,435, 6,040,497; Padgette et al. *Herbicide Resistant Crops*, Lewis Publishers, 53-85, 1996; and Penaloza-Vazquez, et al. Plant Cell Reports 14:482-487, 1995; and aroA (U.S. Pat. No. 5,094,945) for glyphosate tolerance; bromoxynil nitrilase (Bxn) for Bromoxynil tolerance (U.S. Pat. No. 4,810,648); phytoene desaturase (crtI, Misawa et al, (1993) *Plant J.* 4:833-840, and (1994) *Plant J* 6:481-489); for tolerance to norflurazon, acetohydroxyacid synthase (AHAS, aka ALS, Sathasiivan et al. Nucl. Acids Res. 18:2188-2193, 1990); and the bar gene for tolerance to glufosinate and bialaphos (DeBlock, et al. EMBO J. 6:2513-2519, 1987).

Herbicide tolerance is a desirable phenotype for crop plants. N-phosphonomethylglycine, also known as glyphosate, is a well known herbicide that has activity on a broad spectrum of plant species. Glyphosate is the active ingredient of Roundup® (Monsanto Co.), a safe herbicide having a desirably short half life in the environment. When applied onto a plant surface, glyphosate moves systemically through the plant. Glyphosate is toxic to plants by inhibiting the shikimic acid pathway, which provides a precursor for the synthesis of aromatic amino acids. Specifically, glyphosate affects the conversion of phosphoenolpyruvate and 3-phosphoshikimic acid to 5-enolpyruvyl-3-phosphoshikimic acid by inhibiting the enzyme 5-enolpyruvyl-3-phosphoshikimate synthase (hereinafter referred to as EPSP synthase or EPSPS). For purposes of the present invention, the term glyphosate" should be considered to include any herbicidally effective form of N-phosphonomethylglycine (including any salt thereof) and other forms which result in the production of the glyphosate anion in planta.

Through plant genetic engineering methods, it is possible to produce glyphosate tolerant plants by inserting into the plant genome a DNA molecule that causes the production of higher levels of wild-type EPSPS (Shah et al., Science 233:478-481, 1986). Glyphosate tolerance can also be achieved by the expression of EPSPS variants that have lower affinity for glyphosate and therefore retain their catalytic activity in the presence of glyphosate (U.S. Pat. No. 5,633,435). Enzymes that degrade glyphosate in the plant tissues (U.S. Pat. No. 5,463,175) are also capable of conferring cellular tolerance to glyphosate. Such genes, therefore, allow for the production of transgenic crops that are tolerant to glyphosate, thereby allowing glyphosate to be used for effective weed control with minimal concern of crop damage. For example, glyphosate tolerance has been genetically engineered into corn (U.S. Pat. Nos. 5,554,798, 6,040,497), wheat (Zhou et al. Plant Cell Rep. 15:159-163, 1995), soybean (WO 9200377) and canola (WO 9204449).

Variants of the wild-type EPSPS enzyme have been isolated that are glyphosate-resistant as a result of alterations in the EPSPS amino acid coding sequence (Kishore et al., Annu. Rev. Biochem. 57:627-663, 1988; Schulz et al., Arch. Microbiol. 137:121-123, 1984; Sost et al., FEBS Lett. 173: 238-241, 1984; Kishore et al., In "Biotechnology for Crop Protection" ACS Symposium Series No. 379. eds. Hedlin et al., 37-48, 1988). These variants typically have a higher $K_i$ for glyphosate than the wild-type EPSPS enzyme that confers the glyphosate-tolerant phenotype, but these variants are also characterized by a high $K_m$ for PEP that make the enzyme kinetically less efficient. For example, the apparent $K_m$ for PEP and the apparent $K_i$ for glyphosate for the native EPSPS from E. coli are 10 µM and 0.5 µM while for a glyphosate-resistant isolate having a single amino acid substitution of an alanine for the glycine at position 96 these values are 220 µM and 4.0 mM, respectively. U.S. Pat. No. 6,040,497 reports that the mutation known as the TIPS mutation (a substitution of isoleucine for threonine at amino acid position 102 and a substitution of serine for proline at amino acid position 106) comprises two mutations that when introduced into the polypeptide sequence of Zea mays EPSPS confers glyphosate resistance to the enzyme. Transgenic plants containing this mutant enzyme are tolerant to glyphosate. Identical mutations may be made in glyphosate sensitive EPSPS enzymes from other plant sources to create glyphosate resistant enzymes.

A variety of native and variant EPSPS enzymes have been expressed in transgenic plants in order to confer glyphosate tolerance (Singh, et al., In "Biosynthesis and Molecular Regulation of Amino Acids in Plants", Amer Soc Plant Phys. Pubs., 1992). Examples of some of these EPSPSs include those described and/or isolated in accordance with U.S. Pat. Nos. 4,940,835, 4,971,908, 5,145,783, 5,188,642, 5,310, 667, and 5,312,910. They can also be derived from a structurally distinct class of non-homologous EPSPS genes, such as the class II EPSPS genes isolated from Agrobacterium sp. strain CP4 as described in U.S. Pat. Nos. 5,633,435 and 5,627,061.

Chloroplast transit peptides (CTPs) are engineered to be fused to the N terminus of the bacterial EPSPS to direct the glyphosate resistant enzymes into the plant chloroplast. In the native plant EPSPS, chloroplast transit peptide regions are contained in the native coding sequence (e.g., CTP2, Klee et al., Mol. Gen. Genet. 210:47-442, 1987, herein incorporated by reference in its entirety). The native CTP may be substituted with a heterologous CTP during construction of a transgene plant expression cassette. Many chloroplast-localized proteins, including EPSPS, are expressed from nuclear genes as precursors and are targeted to the chloroplast by a chloroplast transit peptide (CTP) that is removed during the import steps. Examples of other such chloroplast proteins include the small subunit (SSU) of Ribulose-1,5,-bisphosphate carboxylase, Ferredoxin, Ferredoxin oxidoreductase, the light-harvesting complex protein I and protein II, and Thioredoxin F. It has been demonstrated in vivo and in vitro that non-chloroplast proteins may be targeted to the chloroplast by use of protein fusions with a CTP and that a CTP sequence is sufficient to target a protein to the chloroplast. Incorporation of a suitable chloroplast transit peptide, such as, the Arabidopsis thaliana EPSPS CTP (Klee et al., Mol. Gen. Genet. 210:437-442 (1987), and the Petunia hybrida EPSPS CTP (della-Cioppa et al., Proc. Natl. Acad. Sci. USA 83:6873-6877 (1986) has been shown to target heterologous EPSPS protein sequences to chloroplasts in transgenic plants. The production of glyphosate tolerant plants by expression of a fusion protein comprising an amino-terminal CTP with a glyphosate resistant EPSPS enzyme is well known by those skilled in the art, (U.S. Pat. Nos. 5,627,061, 5,633,435, 5,312,910, EP 0218571, EP 189707, EP 508909, and EP 924299). Those skilled in the art will recognize that various chimeric constructs can be made that utilize the functionality of a particular CTP to import glyphosate resistant EPSPS enzymes into the plant cell chloroplast.

Modification and changes may be made in the structure of the polynucleotides of the invention and still obtain a molecule that encodes a functional protein or peptide with desirable characteristics. The following is a method based upon substituting the codon(s) of a first polynucleotide to create an equivalent, or even an improved, second-generation artificial polynucleotide, where this new artificial polynucleotide is useful in methods of transgene gene stacking and enhanced expression. It is contemplated that the codon substitutions in the second-generation polynucleotide can in certain instances result in at least one amino acid different from that of the first polynucleotide. The amino acid substitution may provide an improved characteristic to the protein, e.g., a glyphosate resistant EPSP synthase, or it may be a conserved change that does not substantially affect the characteristics of the protein. The method provides for an artificial polynucleotide created by the backtranslation of a polypeptide sequence into a polynucleotide using a codon usage table, followed by steps to enhance characteristics of the artificial polypeptide that make it particularly useful in transgenic plants.

In particular embodiments of the invention, modified polypeptides encoding herbicide is resistant proteins are contemplated to be useful for at least one of the following: to confer herbicide tolerance in a transformed or transgenic plant, to improve expression of herbicide resistance genes in plants, for use as selectable markers for introduction of other traits of interest into a plant, and to prevent recombination with a similar endogenous plant gene or existing transgene further allowing gene stacking without gene silencing.

It is known that the genetic code is degenerate. The amino acids and their RNA codon(s) are listed below in Table 1.

TABLE 1

Amino acids and the RNA codons that encode them.

Amino Acid
Full name; 3 letter code; 1 letter code   Codons

| | |
|---|---|
| Alanine; Ala; A | GCA GCC GCG GCU |
| Cysteine; Cys; C | UGC UGU |
| Aspartic acid; Asp; D | GAC GAU |
| Glutamic acid; Glu; E | GAA GAG |
| Phenylalanine; Phe; F | UUC UUU |
| Glycine; Gly; G | GGA GGC GGG GGU |
| Histidine; His; H | CAC CAU |
| Isoleucine; Ile; I | AUA AUC AUU |
| Lysine; Lys; K | AAA AAG |
| Leucine; Leu; L | UUA UUG CUA CUC CUG CUU |
| Methionine; Met; M | AUG |
| Asparagine; Asn; N | AAC AAU |
| Proline; Pro; P | CCA CCC CCG CCU |
| Glutamine; Gln; Q | CAA CAG |
| Arginine; Arg; R | AGA AGG CGA CGC CGG CGU |
| Serine; Ser; S | AGC AGU UCA UCC UCG UCU |
| Threonine; Thr; T | ACA ACC ACG ACU |
| Valine; Val; V | GUA GUC GUG GUU |
| Tryptophan; Trp; W | UGG |
| Tyrosine; Tyr; Y | UAC UAU |

The codons are described in terms of RNA bases, e.g. adenine, uracil, guanine and cytosine, it is the mRNA that is directly translated into polypeptides. It is understood that when designing a DNA polynucleotide for use in a construct, the DNA bases would be substituted, e.g. thymine instead of uracil.

It is desirable to provide transgenic plants that have multiple agronomically improved phenotypes. Often herbicide tolerance is used as a selectable marker to assist in the production of transgenic plants that may possess additional genes of agronomic importance. The stacking of the transgenes by traditional breeding methods or by retransformation of a first transgenic plant with an additional plant expression cassette may include the introduction of genes or genetic elements that have identical or nearly identical polynucleotide sequence. The progeny containing these stacked genes may be susceptible to loss of gene expression due to gene silencing. The method of the present invention provides a modified polynucleotide molecule that encodes a herbicide resistant protein. The polynucleotide molecules are designed to be sufficiently divergent in polynucleotide sequence from other polynucleotide molecules that encode the same herbicide resistance protein. These molecules can then coexist in the same plant cell without the concern of gene silencing.

The divergent polynucleotide sequence is created by using a codon usage table built from the known coding sequences of various plant species. For example, codon usage tables for *Arabidopsis thaliana, Zea mays*, and *Glycine max* can be used in the method to design the polynucleotides of the present invention. Other codon usage tables from other plants can also be used by those of ordinary skill in the art.

The first step in the method for designing a new artificial polynucleotide molecule that encodes a herbicide tolerance protein is the use of a codon usage table to determine the percent codon usage in a plant species for each amino acid of the herbicide tolerance protein, followed by replacing at least one of every eight contiguous codons with a different codon selected from the codon usage table and adjusting the percent codon usage for each amino acid encoded by the polynucleotide to substantially the same percent codon usage found in the codon usage table. Additional steps can include introducing a translational stop codon in the second and third open reading frame of the new polynucleotide sequence; eliminating some translational start codons in the second and third open reading frames; adjusting the local GC:AT ratio to about 2:1 over a is range of about 50 nucleotides; disrupting potential polyadenylation signals or potential intron splice sites; removing at least one restriction enzyme site of six contiguous nucleotides or greater; and comparing the sequence identity of the new artificial polynucleotide to an existing polynucleotide that encodes the same or similar protein so that the sequence identity between the two polynucleotides is not more than 85 percent.

A back translation of a protein sequence to a nucleotide sequence maybe performed using a codon usage table, such as those found on Genetics Computer Group (GCG) SeqLab or other DNA analysis programs known to those skilled in the art of DNA analysis or as provided in Tables 2, 3 and 4 of the present invention. The codon usage table for *Arabidopsis thaliana* (Table 2), *Zea mays* (Table 3) and *Glycine max* (Table 4) are examples of tables that can be constructed for plant species, codon usage tables can also be constructed that represent monocot or dicot codon usage.

TABLE 2

*Arabidopsis thaliana* codon usage table.

| Amino Acid | Codon | Number | /1000 | Fraction |
|---|---|---|---|---|
| Gly | GGG | 188335.00 | 10.18 | 0.16 |
| Gly | GGA | 443469.00 | 23.98 | 0.37 |
| Gly | GGT | 409478.00 | 22.14 | 0.34 |
| Gly | GGC | 167099.00 | 9.03 | 0.14 |
| Glu | GAG | 596506.00 | 32.25 | 0.48 |
| Glu | GAA | 639579.00 | 34.58 | 0.52 |
| Asp | GAT | 683652.00 | 36.96 | 0.68 |
| Asp | GAC | 318211.00 | 17.20 | 0.32 |
| Val | GTG | 320636.00 | 17.34 | 0.26 |
| Val | GTA | 185889.00 | 10.05 | 0.15 |
| Val | GTT | 505487.00 | 27.33 | 0.41 |
| Val | GTC | 235004.00 | 12.71 | 0.19 |
| Ala | GCG | 162272.00 | 8.77 | 0.14 |
| Ala | GCA | 323871.00 | 17.51 | 0.27 |
| Ala | GCT | 521181.00 | 28.18 | 0.44 |
| Ala | GCC | 189049.00 | 10.22 | 0.16 |
| Arg | AGG | 202204.00 | 10.93 | 0.20 |
| Arg | AGA | 348508.00 | 18.84 | 0.35 |
| Ser | AGT | 260896.00 | 14.11 | 0.16 |
| Ser | AGC | 206774.00 | 11.18 | 0.13 |
| Lys | AAG | 605882.00 | 32.76 | 0.51 |
| Lys | AAA | 573121.00 | 30.99 | 0.49 |
| Asn | AAT | 418805.00 | 22.64 | 0.52 |
| Asn | AAC | 385650.00 | 20.85 | 0.48 |
| Met | ATG | 452482.00 | 24.46 | 1.00 |
| Ile | ATA | 235528.00 | 12.73 | 0.24 |
| Ile | ATT | 404070.00 | 21.85 | 0.41 |
| Ile | ATC | 341584.00 | 18.47 | 0.35 |
| Thr | ACG | 140880.00 | 7.62 | 0.15 |
| Thr | ACA | 291436.00 | 15.76 | 0.31 |
| Thr | ACT | 326366.00 | 17.65 | 0.34 |
| Thr | ACC | 190135.00 | 10.28 | 0.20 |
| Trp | TGG | 231618.00 | 12.52 | 1.00 |
| End | TGA | 19037.00 | 1.03 | 0.43 |
| Cys | TGT | 196601.00 | 10.63 | 0.60 |
| Cys | TGC | 131390.00 | 7.10 | 0.40 |
| End | TAG | 9034.00 | 0.49 | 0.20 |
| End | TAA | 16317.00 | 0.88 | 0.37 |

TABLE 2-continued

_Arabidopsis thaliana codon usage table._

| Amino Acid | Codon | Number | /1000 | Fraction |
|---|---|---|---|---|
| Tyr | TAT | 276714.00 | 14.96 | 0.52 |
| Tyr | TAC | 254890.00 | 13.78 | 0.48 |
| Leu | TTG | 389368.00 | 21.05 | 0.22 |
| Leu | TTA | 237547.00 | 12.84 | 0.14 |
| Phe | TTT | 410976.00 | 22.22 | 0.52 |
| Phe | TTC | 380505.00 | 20.57 | 0.48 |
| Ser | TCG | 167804.00 | 9.07 | 0.10 |
| Ser | TCA | 334881.00 | 18.11 | 0.20 |
| Ser | TCT | 461774.00 | 24.97 | 0.28 |
| Ser | TCC | 203174.00 | 10.99 | 0.12 |
| Arg | CGG | 88712.00 | 4.80 | 0.09 |
| Arg | CGA | 115857.00 | 6.26 | 0.12 |
| Arg | CGT | 165276.00 | 8.94 | 0.17 |
| Arg | CGC | 69006.00 | 3.73 | 0.07 |
| Gln | CAG | 280077.00 | 15.14 | 0.44 |
| Gln | CAA | 359922.00 | 19.46 | 0.56 |
| His | CAT | 256758.00 | 13.88 | 0.62 |
| His | CAC | 160485.00 | 8.68 | 0.38 |
| Leu | CTG | 183128.00 | 9.90 | 0.11 |
| Leu | CTA | 184587.00 | 9.98 | 0.11 |
| Leu | CTT | 447606.00 | 24.20 | 0.26 |
| Leu | CTC | 294275.00 | 15.91 | 0.17 |
| Pro | CCG | 155222.00 | 8.39 | 0.17 |
| Pro | CCA | 298880.00 | 16.16 | 0.33 |
| Pro | CCT | 342406.00 | 18.51 | 0.38 |
| Pro | CCC | 97639.00 | 5.28 | 0.11 |

TABLE 3

_Zea mays codon usage table_

| Amino Acid | Codon | Number | /1000 | Fraction |
|---|---|---|---|---|
| Gly | GGG | 8069.00 | 15.19 | 0.21 |
| Gly | GGA | 7100.00 | 13.37 | 0.18 |
| Gly | GGT | 7871.00 | 14.82 | 0.20 |
| Gly | GGC | 15904.00 | 29.94 | 0.41 |
| Glu | GAG | 22129.00 | 41.67 | 0.68 |
| Glu | GAA | 10298.00 | 19.39 | 0.32 |
| Asp | GAT | 11996.00 | 22.59 | 0.41 |
| Asp | GAC | 17045.00 | 32.09 | 0.59 |
| Val | GTG | 13873.00 | 26.12 | 0.38 |
| Val | GTA | 3230.00 | 6.08 | 0.09 |
| Val | GTT | 8261.00 | 15.55 | 0.23 |
| Val | GTC | 11330.00 | 21.33 | 0.31 |
| Ala | GCG | 11778.00 | 22.18 | 0.24 |
| Ala | GCA | 8640.00 | 16.27 | 0.18 |
| Ala | GCT | 11940.00 | 22.48 | 0.24 |
| Ala | GCC | 16768.00 | 31.57 | 0.34 |
| Arg | AGG | 7937.00 | 14.94 | 0.27 |
| Arg | AGA | 4356.00 | 8.20 | 0.15 |
| Ser | AGT | 3877.00 | 7.30 | 0.10 |
| Ser | AGC | 8653.00 | 16.29 | 0.23 |
| Lys | AAG | 22367.00 | 42.11 | 0.74 |
| Lys | AAA | 7708.00 | 14.51 | 0.26 |
| Asn | AAT | 6997.00 | 13.17 | 0.36 |
| Asn | AAC | 12236.00 | 23.04 | 0.64 |
| Met | ATG | 12841.00 | 24.18 | 1.00 |
| Ile | ATA | 3997.00 | 7.53 | 0.16 |
| Ile | ATT | 7457.00 | 14.04 | 0.31 |
| Ile | ATC | 12925.00 | 24.34 | 0.53 |
| Thr | ACG | 5665.00 | 10.67 | 0.22 |
| Thr | ACA | 5408.00 | 10.18 | 0.21 |
| Thr | ACT | 5774.00 | 10.87 | 0.22 |
| Thr | ACC | 9256.00 | 17.43 | 0.35 |
| Trp | TGG | 6695.00 | 12.61 | 1.00 |
| End | TGA | 591.00 | 1.11 | 0.45 |
| Cys | TGT | 2762.00 | 5.20 | 0.30 |
| Cys | TGC | 6378.00 | 12.01 | 0.70 |
| End | TAG | 411.00 | 0.77 | 0.32 |
| End | TAA | 299.00 | 0.56 | 0.23 |
| Tyr | TAT | 4822.00 | 9.08 | 0.31 |
| Tyr | TAC | 10546.00 | 19.86 | 0.69 |

TABLE 3-continued

_Zea mays codon usage table_

| Amino Acid | Codon | Number | /1000 | Fraction |
|---|---|---|---|---|
| Leu | TTG | 6677.00 | 12.57 | 0.14 |
| Leu | TTA | 2784.00 | 5.24 | 0.06 |
| Phe | TTT | 6316.00 | 11.89 | 0.32 |
| Phe | TTC | 13362.00 | 25.16 | 0.68 |
| Ser | TCG | 5556.00 | 10.46 | 0.14 |
| Ser | TCA | 5569.00 | 10.49 | 0.15 |
| Ser | TCT | 6149.00 | 11.58 | 0.16 |
| Ser | TCC | 8589.00 | 16.17 | 0.22 |
| Arg | CGG | 4746.00 | 8.94 | 0.16 |
| Arg | CGA | 2195.00 | 4.13 | 0.07 |
| Arg | CGT | 3113.00 | 5.86 | 0.10 |
| Arg | CGC | 7374.00 | 13.88 | 0.25 |
| Gln | CAG | 13284.00 | 25.01 | 0.64 |
| Gln | CAA | 7632.00 | 14.37 | 0.36 |
| His | CAT | 5003.00 | 9.42 | 0.39 |
| His | CAC | 7669.00 | 14.44 | 0.61 |
| Leu | CTG | 13327.00 | 25.09 | 0.28 |
| Leu | CTA | 3785.00 | 7.13 | 0.08 |
| Leu | CTT | 8238.00 | 15.51 | 0.17 |
| Leu | CTC | 12942.00 | 24.37 | 0.27 |
| Pro | CCG | 8274.00 | 15.58 | 0.27 |
| Pro | CCA | 7845.00 | 14.77 | 0.26 |
| Pro | CCT | 7129.00 | 13.42 | 0.23 |
| Pro | CCC | 7364.00 | 13.87 | 0.24 |

TABLE 4

_Glycine max codon usage table_

| Amino Acid | Codon | Number | /1000 | Fraction |
|---|---|---|---|---|
| Gly | GGG | 3097.00 | 12.82 | 0.18 |
| Gly | GGA | 5434.00 | 22.49 | 0.32 |
| Gly | GGT | 5248.00 | 21.72 | 0.31 |
| Gly | GGC | 3339.00 | 13.82 | 0.20 |
| Glu | GAG | 8296.00 | 34.33 | 0.50 |
| Glu | GAA | 8194.00 | 33.91 | 0.50 |
| Asp | GAT | 7955.00 | 32.92 | 0.62 |
| Asp | GAC | 4931.00 | 20.40 | 0.38 |
| Val | GTG | 5342.00 | 22.11 | 0.32 |
| Val | GTA | 1768.00 | 7.32 | 0.11 |
| Val | GTT | 6455.00 | 26.71 | 0.39 |
| Val | GTC | 2971.00 | 12.29 | 0.18 |
| Ala | GCG | 1470.00 | 6.08 | 0.08 |
| Ala | GCA | 5421.00 | 22.43 | 0.31 |
| Ala | GCT | 6796.00 | 28.12 | 0.38 |
| Ala | GCC | 4042.00 | 16.73 | 0.23 |
| Arg | AGG | 3218.00 | 13.32 | 0.28 |
| Arg | AGA | 3459.00 | 14.31 | 0.30 |
| Ser | AGT | 2935.00 | 12.15 | 0.17 |
| Ser | AGC | 2640.00 | 10.92 | 0.15 |
| Lys | AAG | 9052.00 | 37.46 | 0.59 |
| Lys | AAA | 6370.00 | 26.36 | 0.41 |
| Asn | AAT | 5132.00 | 21.24 | 0.48 |
| Asn | AAC | 5524.00 | 22.86 | 0.52 |
| Met | ATG | 5404.00 | 22.36 | 1.00 |
| Ile | ATA | 3086.00 | 12.77 | 0.23 |
| Ile | ATT | 6275.00 | 25.97 | 0.47 |
| Ile | ATC | 3981.00 | 16.47 | 0.30 |
| Thr | ACG | 1006.00 | 4.16 | 0.08 |
| Thr | ACA | 3601.00 | 14.90 | 0.29 |
| Thr | ACT | 4231.00 | 17.51 | 0.34 |
| Thr | ACC | 3562.00 | 14.74 | 0.29 |
| Trp | TGG | 2866.00 | 11.86 | 1.00 |
| End | TGA | 221.00 | 0.91 | 0.36 |
| Cys | TGT | 1748.00 | 7.23 | 0.49 |
| Cys | TGC | 1821.00 | 7.54 | 0.51 |
| End | TAG | 143.00 | 0.59 | 0.23 |
| End | TAA | 256.00 | 1.06 | 0.41 |
| Tyr | TAT | 3808.00 | 15.76 | 0.51 |
| Tyr | TAC | 3667.00 | 15.17 | 0.49 |
| Leu | TTG | 5343.00 | 22.11 | 0.24 |
| Leu | TTA | 2030.00 | 8.40 | 0.09 |

TABLE 4-continued

*Glycine max* codon usage table

| Amino Acid | Codon | Number | /1000 | Fraction |
|---|---|---|---|---|
| Phe | TTT | 4964.00 | 20.54 | 0.49 |
| Phe | TTC | 5067.00 | 20.97 | 0.51 |
| Ser | TCG | 1107.00 | 4.58 | 0.06 |
| Ser | TCA | 3590.00 | 14.86 | 0.21 |
| Ser | TCT | 4238.00 | 17.54 | 0.24 |
| Ser | TCC | 2949.00 | 12.20 | 0.17 |
| Arg | CGG | 683.00 | 2.83 | 0.06 |
| Arg | CGA | 964.00 | 3.99 | 0.08 |
| Arg | CGT | 1697.00 | 7.02 | 0.15 |
| Arg | CGC | 1538.00 | 6.36 | 0.13 |
| Gln | CAG | 4147.00 | 17.16 | 0.46 |
| Gln | CAA | 4964.00 | 20.54 | 0.54 |
| His | CAT | 3254.00 | 13.47 | 0.55 |
| His | CAC | 2630.00 | 10.88 | 0.45 |
| Leu | CTG | 2900.00 | 12.00 | 0.13 |
| Leu | CTA | 1962.00 | 8.12 | 0.09 |
| Leu | CTT | 5676.00 | 23.49 | 0.26 |
| Leu | CTC | 4053.00 | 16.77 | 0.18 |
| Pro | CCG | 1022.00 | 4.23 | 0.08 |
| Pro | CCA | 4875.00 | 20.17 | 0.37 |
| Pro | CCT | 4794.00 | 19.84 | 0.36 |
| Pro | CCC | 2445.00 | 10.12 | 0.19 |

Codon usage tables are well known in the art and can be found in gene databases e.g., Genbank database. The Codon Usage Database is an extended WWW version of CUTG (Codon Usage Tabulated from Genbank). The frequency of codon usage in each organism is made searchable through this World Wide Web site (Nakamura et al. Nucleic Acids Res. 28:292, 2000).

In various embodiments of the invention, the steps may be performed in any order or simultaneously. Any or all of the steps may be performed in the design of an artificial polynucleotide of the invention. Each step is described in detail below.

Different codons for a particular amino acid should be distributed throughout the polynucleotide based on approximate percentage codon usage for particular species from a codon usage table. Local cluster of identical codons should be avoided. At least one codon is substituted for every eight contiguous codons to provide sufficient divergence of polynucleotide sequences that encode identical or similar proteins. Except where specifically desired, e.g. to provide a herbicide tolerant enzyme, the encoded protein remains unchanged by substituting one codon for another codon that is translated to the same amino acid as listed in Table 1.

In embodiments of the present invention, corrections are made to the local GC:AT ratio of a polynucleotide by adjusting local GC:AT ratio to be about the same ratio as the full length is polynucleotide, but not higher than 2× over a range of about 50 contiguous nucleotides of the polynucleotide molecule. The range of GC:AT ratios of a polynucleotide using codon usage tables from dicot plants should be from about 0.9 to about 1.3, and for monocot plants from about 1.2 to about 1.7. The local GC:AT ratio may be important in maintenance of appropriate secondary structure of RNA. Regions comprising many consecutive A+T bases or G+C bases are predicted to have a higher likelihood to form hairpin structures due to self-complementarity. Therefore, replacement with a different codon would reduce the likelihood of self-complementary secondary structure formation, which is known to reduce transcription and/or translation in some organisms. In most cases, the adverse effects may be minimized by using polynucleotide molecules that do not contain more than five consecutive A+T or G+C. The maximum length of local GC track (without any AT nucleotide) should be no longer than 10 nucleotides. Therefore codons encoding Gly, Ala, Arg, Ser, and Pro rich proteins can be substituted to prevent long clusters of GC nucleotides. The listed GC rich codons may be used in combination with the AT rich codons for amino acids Lys, Asn, Ile, Tyr, Leu, Phe and vice versa to correct local GC:AT ratio.

A sequence identity check using nucleotide sequence alignment tools such as GAP program (GCG, Madison, Wis.) can be done immediately after back translation to insure that the generated sequence has appropriate degree of sequence diversity. Contiguous polynucleotide sequence longer than 23 nucleotides having one hundred percent sequence identity should be eliminated by making codon substitutions in these lengths of sequence.

The translational start codons (ATG from the DNA, AUG in the mRNA) present in the second reading frame (frame "b"), the third reading frame (frame "c"), and the reverse reading frames (frame "d", "e", "f"). The second and third frame start codons may initiate translation, however much less efficiently than the first. Therefore, if one or two AUG are found near the 5' end of an mRNA molecule reside in frame "b" or "c" it would be beneficial to eliminate them in a polynucleotide region that contains at least the first three Met codons in frame "a". Also, if protein sequence does not have more than one Met in frame "a", then eliminate as many as possible from the "b" or "c" forward frames. To perform this, for example, the codons for amino acids, Asp, Asn, Tyr, His in the protein of interest followed by any of the amino acids: Gly, Glu, Asp, Val, or Ala, can be substituted to eliminate a start codon in the second frame. The sequence GATGGG encodes the amino acids Asp-Gly and forms an ATG in the reading frame "b". When the sequence is modified to GACGGG, the ATG start is eliminated and the sequence still is encodes Asp-Gly. A similar strategy is used to eliminate start codons in the reading frame "c". The combination of an amino acid selected from the group of Gly, Glu, Val, Ala, Arg, Lys, Ile, Thr, Cys, Tyr, Leu, Ser, His or Pro followed by Trp can result in formation on ATG in third reading frame of the gene. In this situation, the first codon can be changed to have a nucleotide other than A in third position.

The elimination of ATG codon in the complementary DNA strand of the gene in alternate frames ("d", "e", and/or "f") without changing amino acid sequence of the protein can be accomplished in a similar manner. This modification reduces the probability of translation even if the transgene is integrated into a plant genome in an orientation that allows transcription of the reverse complement mRNA from a native plant promoter. Translation from any reverse reading frame can be minimized by introduction of a stop codon in all three reverse reading frames as described below.

The creation of stop codons to all three frames of the complementary DNA can be accomplished as follows. The Leu (TTA and CTA) and Ser codon (TCA) produce three different stop codons in reverse complement strand. If those amino acids can be found at the C terminus of the protein of interest, their codons may used to generate stops in the complementary strand in the reading frame "d". To generate a stop codon in the reading frame "e" of complementary strand, find amino acids Ala, Arg, Asn, Asp, Cys, Gly, His, Ile, Leu Phe, Pro, Ser, Thr, Tyr, or Val followed by amino acids Gln, His or Tyr of the protein of interest. For example, polynucleotide sequence of GCCCAC that encode for amino acids Ala-His can be modified to GCTCAC. The complementary sequence, GTGAGC, will have now TGA stop codon shown in italics. When the protein of interest has a Ala, Ile, Leu, Phe, Pro, Ser, Thr or Val followed by an Arg, Asn, Ile, Lys, Met, or Ser the reading frame in the complementary strand can be modified to have a stop codon in the reading frame "f" of the complementary strand. The polynucleotide sequence ATATCT for Ile and Ser can be modified to ATCAGT to generate stop codon in complementary strand as shown in italics, ACTGAT. The combination of codons for Phe followed by any of the codons for amino acids Asn, Ile, Lys, Met or Thr will always generate stop codon in complementary strand frame "e" or "f".

To create a stop codon in the forward reading frame "b", the reading frame a must end on nucleotides TA or TG. Search the protein of interest for the amino acids Ile, Leu, Met or Val in combination with any of the following amino acids: Ala, Arg, Asn Asp, Glu, Gly, Ile, Lys, Met, Ser, Thr or Val. For example, if the polynucleotide sequence encoding the amino acids Met-Ser is ATGTCT, it can be modified to ATGAGT to produce a TGA stop codon in second reading frame.

To be able to create a stop codon to the reading frame "c", the reading frame "a" must have the nucleotide T in third position and next codon must start from AA, AG or GA. To find suitable codons to modify, search the protein of interest for any of the amino acids: Ala, Asn, Asp, Arg, Cys, Gly, His, Ile, Leu Phe, Pro, Ser, Thr, Tyr or Val follow by any of the following amino acids: Arg, Asn, Asp, Glu, Lys or Ser. For example, if the nucleotide sequence for amino acids Gly-Glu is GGAGAG, the sequence can be modified to GGTGAG to create a TGA stop codon in the third reading frame.

Another useful modification in artificial polynucleotide design methods of the present invention is to eliminate unwanted restriction sites and other specific sequence patterns. Restriction sites may interfere with future gene cloning and manipulations. For example, some restriction sites commonly used in gene cloning include, but are not limited, to the Type II restriction enzymes with 6 or more non-N bases listed in Table 5 below which is an excerpt from the New England Biolabs, Inc. (Beverly, Mass., USA) restriction endonuclease database. The search for restriction enzyme recognition sites can be done using Map function application found in GCG SeqLab or a similar application contained in other DNA analysis programs known to those skilled in the art of DNA analysis. The restriction enzymes can be also added to the sequence to facilitate cloning. For example, The ClaI restriction site is placed in CP4EPSPS version AT (SEQ ID NO:17) and ZM (SEQ ID NO:18) to generate recombinant sequences by fragment exchange and to facilitate gene synthesis using nucleotide fragments that can be assemble to the whole gene. The transit peptide CTP2 polynucleotide sequence (SEQ ID NO:12) is connected with CP4EPSPS by SphI restriction site to facilitate substitution of CTP2 with different nucleotide versions of CTP2 (SEQ ID NO:13, SEQ ID NO:14) or polynucleotides encoding different chloroplast transit peptides. For example, in the rice EPSPS, the NgaMIV restriction site is preserved at about nucleotide position 205 in all artificial versions to facilitate chloroplast transit peptide coding region exchange. Also, for soybean EPSPS the polynucleotide sequence for the chloroplast transit peptide is separated from the mature peptide by the restriction site for SacII endonuclease.

It is understood that modification of endonuclease restriction sites is not required, but is useful for further manipulation of the DNA molecules. Table 5 provides a list of restriction endonucleases, those of particular interest to the present invention are marked with an asterisk. Other endonuclease restriction sites desirable for elimination or addition to an artificial polynucleotide of the present invention will be apparent to those of ordinary skill in the art and are not limited to those listed in Table 5.

TABLE 5

Restriction enzymes recognition sequences

| Enzymes | Recognition Sequence |
|---|---|
| AatII | G_ACGT^C |
| *AccI | GT^MK_AC |
| Acc65I | G^GTAC_C |
| AceII | G_CTAG^C- |
| AclI | AA^CG_TT |
| AcyI | GR^CG_YC |
| AfeI | AGC^GCT |
| AflII | C^TTAA_G |
| *AflIII | A^CRYG_T |
| AgeI | A^CCGG_T |
| AhaIII | TTT^AAA |
| ApaI | G_GGCC^C |
| ApaLI | G^TGCA_C |
| ApoI | R^AATT_Y |
| AscI | GG^CGCG_CC |
| AseI | AT^TA_AT |
| AsiSI | GCG_AT^CGC |
| AsuII | TT^CG_AA |
| AvaI | C^YCGR_G |
| AvaIII | ATGCAT |
| AvrII | C^CTAG_G |
| BalI | TGG^CCA |
| *BamHI | G^GATC_C |
| BanI | G^GYRC_C |
| BanII | G_RGCY^C |
| *BbeI | G_GCGC^C |
| BbvCI | CC^TCA_GC |
| *BclI | T^GATC_A |
| BetI | W^CCGG_W |
| BfrBI | ATG^CAT |
| *BglII | A^GATC_T |
| BloHII | CTGCA^G |
| BlpI | GC^TNA_GC |
| Bme1580I | G_KGCM^C |

TABLE 5-continued

Restriction enzymes recognition sequences

| Enzymes | Recognition Sequence |
|---|---|
| BmgI | GKGCCC |
| Bpu10I | CC^TNA_GC |
| BsaI | GGTCTCN^NNNN_ |
| BsaAI | YAC^GTR |
| BsaHI | GR^CG_YC |
| BsaWI | W^CCGG_W |
| BsbI | CAACAC |
| BsePI | G^CGCG_C |
| BseSI | G_KGCM^C |
| BsiI | C^ACGA_G |
| BsiEI | CG_RY^CG |
| BsiWI | C^GTAC_G |
| BsmI | GAATG_CN^ |
| Bsp1286I | G_DGCH^C |
| Bsp1407I | T^GTAC_A |
| BspEI | T^CCGG_A |
| BspGI | CTGGAC |
| BspHI | T^CATG_A |
| BspLU11I | A^CATC_T |
| BspMII | T^CCGG_A |
| BsrBI | CCG^CTC |
| BsrDI | GCAATG_NN^ |
| BsrFI | R^CCGG_Y |
| BsrGI | T^GTAC_A |
| BssHII | G^CGCGT_C |
| BssSI | C^ACGA_G |
| BstAPI | GCAN_NNN^NTGC |
| BstBI | TT^CG_AA |
| BstEII | GA^TNAC_C |
| BstXI | CCAN_NNNN^NTGG |
| BstYI | R^GATC_Y |
| BstZ17I | GTA^TAC |
| Bsu36I | CC^TNNA_GG |
| BtgI | C^CRYG_G |
| BtrI | CAC^GTC |
| BtsI | GCAGTG_NNA^ |
| CfrI | Y^GGCC_R |

TABLE 5-continued

Restriction enzymes recognition sequences

| Enzymes | Recognition Sequence |
|---|---|
| Cfr10I | R^CCGG_Y |
| *ClaI | AT^CG_AT |
| DraI | TTT^AAA |
| DraII | RG^GNC_CY |
| DrdII | GAACCA |
| DsaI | C^CRYG_G |
| EaeI | Y^GGCC_R |
| EagI | C^GGCC_G |
| Ecl136II | GAG^CTC |
| Eco47III | AGC^GCT |
| EcoNI | CCTNN^N_NNAGG |
| EcoO109I | RG^GNC_CY |
| *EcoRI | G^AATT_C |
| *EcoRV | GAT^ATC |
| EspI | GC^TNA_GC |
| *FseI | GG_CCGG^CC |
| *FspI | TGC^GCA |
| FspAI | RTGC^GCAY |
| GdiII | C^GGCC_R |
| HaeI | WGG^CCW |
| HaeII | R_GCGC^Y |
| HgiAI | G_WGCW^C |
| HgiCI | G^GYRC_C |
| HgiJII | G_RGCY^C |
| *HincII | GTY^RAC |
| HindII | GTY^RAC |
| *HindIII | A AGCT_T |
| *HpaI | GTT^AAC |
| KasI | G^GCGC_C |
| *KpnI | G_GTAC^C |
| LpnI | RGC^GCY |
| McrI | CG_RY^CG |
| MfeI | C^AATT_G |
| *MluI | A^CGCG_T |
| MscI | TGG^CCA |
| MspAlI | CMG^CKG |
| MstI | TGC^GCA |

TABLE 5-continued

Restriction enzymes recognition sequences

| Enzymes | Recognition Sequence |
|---|---|
| NaeI | GCC^GGC |
| NarI | GG^CG_CC |
| *NcoI | C^CATG_G |
| *NdeI | CA^TA_TG |
| *NgoMIV | G^CCGG_C |
| *NheI | G^CTAG_C |
| Nli3877I | C_YCGR^G |
| *NotI | GC^GGCC_GC |
| *NruI | TCG^CGA |
| *NsiI | A_TGCA^T |
| NspI | R_CATG^Y |
| NspBII | CMG^CKG |
| *PacI | TTA_AT^TAA |
| *PciI | A^CATG_T |
| Pfl1108I | TCGTAG |
| *PflMI | CCAN_NNN^NTGG |
| PmaCI | CAC^GTG |
| PmeI | GTTT^AAAC |
| PmlI | CAC^GTG |
| Ppu10I | A^TGCA_T |
| *PpuMI | RG^GWC_CY |
| PshAI | GACNN^RNGTC |
| PsiI | TTA^TAA |
| *PspOMI | G^GGCC_C |
| PssI | RG_GNC^CY |
| *PstI | C_TGCA^G |
| *PvuI | CG_AT^CG |
| *PvuII | CAG^CTG |
| RsrII | CG^GWC_CG |
| *SacI | G_AGCT^C |
| *SacII | CC_GC^GG |
| *SalI | G^TCGA_C |
| SanDI | GG^GWC_CC |
| SapI | GCTCTTCN^NNN_ |
| SauI | CC^TNA_GG |
| SbfI | CC_TGCA^GG |
| *ScaI | AGT^ACT |

TABLE 5-continued

Restriction enzymes recognition sequences

| Enzymes | Recognition Sequence |
|---|---|
| SciI | CTC^GAG |
| SduI | G_DGCH^C |
| SexAI | A^CCWGG_T |
| SfcI | C^TRYA_G |
| SfeI | C^TRYA_G |
| SfiI | GGCCN_NNN^NGGCC |
| SfoI | GGC^GCC |
| SgfI | GCG_AT^CGC |
| SgrAI | CR^CCGG_YG |
| *SmaI | CCC^GGG |
| SmlI | C^TYRA_G |
| SnaI | GTATAC |
| *SnaBI | TAC^GTA |
| *SpeI | A^CTAG_T |
| *SphI | G_CATG^C |
| SplI | C^GTAC_G |
| SrfI | GCCC^GGGC |
| Sse232I | CG^CCGG_CG |
| Sse8387I | CC_TGCA^GG |
| Sse8647I | AG^GWC_CT |
| *SspI | AAT^ATT |
| *StuI | AGG^CCT |
| *StyI | C^CWWG_G |
| *SwaI | ATTT^AAAT |
| TatI | W^GTAC_W |
| UbaMI | TCCNGGA |
| UbaPI | CGAACG |
| *VspI | AT^TA_AT |
| *XbaI | T^CTAG_A |
| *XhoI | C^TCGA_G |
| XhoII | R^GATC_Y |
| *XmaI | C^CCGG_G |
| XmaIII | C^GGCC_G |
| XmnI | GAANN^NNTTC |
| ZraI | GAC^GTC |

A pattern search may be performed to find potential destabilizing sequences and polyadenylation sites and then disrupt or eliminate them as described in U.S. Pat. No.

5,500,365. Certain long stretches of AT rich regions, e.g. the sequence motif ATTTA (or AUUUA, as it appears in RNA) have been implicated as a destabilizing sequence in mammalian cell mRNA (Shaw and Kamen, Cell 46:659-667, 1986). Many short lived mRNAs have A+T rich 3' untranslated regions, and these regions often have the ATTTA sequence, sometimes present in multiple copies or as multimers (e.g., ATTTATTTA . . . ). Shaw and Kamen showed that the transfer of the 3' end of an unstable mRNA to a stable RNA (globin or VA1) decreased the stable RNA's halflife dramatically. They further showed that a pentamer of ATTTA had a profound destabilizing effect on a stable message, and that this signal could exert its effect whether it is located at the 3' end or within the coding sequence. However, the number of ATTTA sequences and/or the sequence context in which they occur also appear to be important in determining whether they function as destabilizing sequences. They also showed that a trimer of ATTTA had much less effect than a pentamer on mRNA stability and a dimer or a monomer is had no effect on stability. Note that multimers of ATTTA such as a pentamer automatically create an A+T rich region. In other unstable mRNAs, the ATTTA sequence may be present in only a single copy, but it is often contained in an A+T rich region. A repeat of 11 AUUUA pentamers has been shown to target reporter transcripts for rapid degradation in plants (Ohme-Takagi et al., Proc. Nat. Acad. Sci. USA 90, 11811-11815, 1993). ATTTA sequence can be formed by combination of codons for amino acid Ile (ATT) and Tyr (TAT) as shown ATTTAT. Another example could be codons that end on AT as in Asn, Asp, His or Tyr, followed by TTA codon for Leu (e.g. AATTTA). Also codon for Phe (UUU) when placed between codons that ends on A and starts on A will form ATTTA motif. To eliminate this motif usually single nucleotide change is sufficient as in example shown: GCATTTAGC change to GCATTCAGC or GCCTTTAGC. All three polynucleotide shown code for Ala-Phe-Arg.

More cis-acting sequences that target transcript for rapid turnover in plants and in other system has been identified (Abler and Green, Plant Mol. Biol. 32:63-78, 1997). Those include the DST element that consist three highly conserved subdomains separated by two variable regions found downstream of the stop codon of SAUR transcripts (Newmaan et al., Plant Cell 5: 701-714, 1993). The second and third subdomains of DST elements contain residues that are invariant among DST elements and are termed ATAGAT and GTA, respectively. Both of those subdomains are necessary for DST function. New artificial polynucleotide sequences are screened for the presence of conserved motifs of DST elements. Those sequences are eliminated by base substitutions of codons preserving protein sequence encoded by the polynucleotide. The DST sequence motifs GGAG, ATAGAT, CATTT and GTAT that appeared in clusters or patterns similar to the conserved DST sequence are also eliminated by base substitutions.

Polynucleotide sequences that may possibly function as polyadenylation sites are eliminated in the new polynucleotide design (U.S. Pat. No. 5,500,365). These polyadenylation signals may not act as proper polyA sites, but instead function as aberrant sites that give rise to unstable mRNAs.

The addition of a polyadenylate string to the 3' end of a mRNA is common to most eukaryotic mRNAs. Contained within this mRNA transcript are signals for polyadenylation and proper 3' end formation. This processing at the 3' end involves cleavage of the mRNA and addition of polyA to the mature 3' end. By searching for consensus sequences near the polyA tract in both plant and animal mRNAs, it has been possible to identify consensus sequences that apparently are involved in polyA addition and 3' end cleavage. The same consensus sequences seem to be important to both of these processes. These signals are typically a variation on the sequence AATAAA. In animal cells, some variants of this sequence that are functional have been identified; in plant cells there seems to be an extended range of functional sequences (Dean et al., Nucl Acid Res., 14:2229-2240, 1986; Hunt, Annu Rev. Plant Physiol. Plant Mol. Biol. 45:47-60, 1994; Rothine, Plant Mol. Biol. 32:43-61, 1996). All of these consensus sequences are variations on AATAAA, therefore, they all are A+T rich sequences.

Typically, to obtain sufficient expression of modified transgenes in plants, existing structural polynucleotide coding sequence ("structural gene") that encodes for the protein of interest is modified by removal of ATTTA sequences and putative polyadenylation signals by site directed mutagenesis of the DNA comprising the structural gene. Substantially all of the known polyadenylation signals and ATTTA sequences are removed in the modified polynucleotide, although enhanced expression levels are often observed with only removal of some of the above identified polyadenylation signal sequences. Alternately, if an artificial polynucleotide is prepared that encodes for the subject protein, codons are selected to avoid the ATTTA sequence and putative polyadenylation signals. For purposes of the present invention putative polyadenylation signals include, but are not necessarily limited to, AATAAA, AATAAT, AACCAA, ATATAA, AATCAA, ATACTA, ATAAAA, ATGAAA, AAGCAT, ATTAAT, ATACAT, AAAATA, ATTAAA, AATTAA, AATACA and CATAAA.

The selected DNA sequence is scanned to identify regions with greater than four consecutive adenine (A) or thymine (T) nucleotides. The A+T regions are scanned for potential plant polyadenylation signals. Although the absence of five or more consecutive A or T nucleotides eliminates most plant polyadenylation signals, if there are more than one of the minor polyadenylation signals identified within ten nucleotides of each other, then the nucleotide sequence of this region is altered to remove these signals while maintaining the original encoded amino acid sequence.

The next step is to consider the about 15 to about 30 or so nucleotide residues surrounding the A+T rich region. If the A+T content of the surrounding region is less than 80%, the region should be examined for polyadenylation signals. Alteration of the region based on polyadenylation signals is dependent upon (1) the number of polyadenylation signals present and (2) presence of a major plant polyadenylation signal. The polyadenylation signals are removed by base substitution of the DNA sequence in the context of codon replacement.

Two additional patterns not identified in U.S. Pat. No. 5,500,365, are searched for and eliminated in embodiments of the present invention. The sequences AG<u>GT</u>AA and GC<u>AG</u>GT are consensus sequences for intron 5' and 3' splice sites, respectively, in monocot plants and dicot plants. Only <u>GT</u> of the 5' splice site and the <u>AG</u> in the 3' splice site are required to be an exact match. However, when conducting a search for these consensus sequences, no mismatch is allowed for each base.

After each step sequence mapping is done using MAP program from GCG to determine location of the open reading frames and identify sequence patterns that further need to be modified. The final step would be to perform sequence identity analysis using for example the GAP program from GCG package to determine degree of sequence divergence and percent identity.

Polypeptides

Generally, the translated protein of the artificial polynucleotide will have the same amino acid sequence as the protein translated from the unmodified coding region. However, the substitution of codons that encode for amino acids that provide a functional homologue of the protein is an aspect of the invention. For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated by the inventors that various changes may be made in the peptide sequences of the disclosed compositions by making changes in the corresponding DNA sequences that encode the peptides in which the peptides shown no appreciable loss of their biological utility or activity.

A further aspect of the invention comprises functional homologues, which differ in one or more amino acids from those of a polypeptide provided herein as the result of one or more conservative amino acid substitutions. It is well known in the art that one or more amino acids in a native sequence can be substituted with at least one other amino acid, the charge and polarity of which are similar to that of the native amino acid, resulting in a silent change. For instance, valine is a conservative substitute for alanine and threonine is a conservative substitute for serine. Conservative substitutions for an amino acid within the native polypeptide sequence can be selected from other members of the class to which the naturally occurring amino acid belongs. Amino acids can be divided into the following four groups: (1) acidic amino acids, (2) basic amino acids, (3) neutral polar amino acids, and (4) neutral nonpolar amino acids. Representative amino acids within these various groups include, but are not limited to: (1) acidic (negatively charged) amino acids such as aspartic acid and glutamic acid; (2) basic (positively charged) amino acids such as arginine, histidine, and lysine; (3) neutral polar amino acids such as glycine, serine, threonine, cysteine, tyrosine, asparagine, and glutamine; and (4) neutral nonpolar (hydrophobic) amino acids such as alanine, leucine, isoleucine, valine, proline, phenylalanine, tryptophan, and methionine. Conserved substitutes for an amino acid within a native amino acid sequence can be selected from other members of the group to which the naturally occurring amino acid belongs. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Naturally conservative amino acids substitution groups are: valine-leucine, valine-isoleucine, phenylalanine-tyrosine, lysine-arginine, alanine-valine, aspartic acid-glutamic acid, and asparagine-glutamine.

DNA Constructs

Exogenous genetic material may be transferred into a plant by the use of a DNA construct designed for such a purpose by methods that utilize *Agrobacterium*, particle bombardment or other methods known to those skilled in the art. Design of such a DNA is construct is generally within the skill of the art (*Plant Molecular Biology: A Laboratory Manual*, eds. Clark, Springer, New York (1997). Examples of such plants in to which exogenous genetic material may be transferred, include, without limitation, alfalfa, *Arabidopsis*, barley, *Brassica*, broccoli, cabbage, citrus, cotton, garlic, oat, oilseed rape, onion, canola, flax, maize, an ornamental annual and ornamental perennial plant, pea, peanut, pepper, potato, rice, rye, sorghum, soybean, strawberry, sugarcane, sugar beet, tomato, wheat, poplar, pine, fir, eucalyptus, apple, lettuce, lentils, grape, banana, tea, turf grasses, sunflower, oil palm, *Phaseolus*, trees, shrubs, vines, etc. It is well known that agronomically important plants comprise genotypes, varieties and cultivars, and that the methods and compositions of the present invention can be tested in these plants by those of ordinary skill in the art of plant molecular biology and plant breeding.

A large number of isolated DNA promoter molecules that are active as a genetic element of a transgene in plant cells have been described. These include the nopaline synthase (P-nos) promoter (Ebert et al., Proc. Natl. Acad. Sci. (U.S.A.) 84:5745-5749, 1987), the entirety of which is herein incorporated by reference), the octopine synthase (P-ocs) promoter, which are carried on tumor-inducing plasmids of *Agrobacterium tumefaciens*, the caulimovirus promoters, such as the cauliflower mosaic virus (CaMV) 19S promoter (Lawton et al., Plant Mol. Biol. 9:315-324, 1987), the entirety of which is herein incorporated by reference) and the CaMV 35S promoter (Odell et al., Nature 313:810-812, 1985), the entirety of which is herein incorporated by reference), the figwort mosaic virus 35S promoter (U.S. Pat. No. 6,018,100, the entirety of which is herein incorporated by reference), the light-inducible promoter from the small subunit of ribulose-1,5-bis-phosphate carboxylase (ss-RUBISCO), the Adh promoter (Walker et al., Proc. Natl. Acad. Sci. (U.S.A.) 84:6624-6628, 1987), the entirety of which is herein incorporated by reference), the sucrose synthase promoter (Yang et al., Proc. Natl. Acad. Sci. (U.S.A.) 87:4144-4148, 1990), the entirety of which is herein incorporated by reference), the R gene complex promoter (Chandler et al., Plant Cell 1:1175-1183, 1989, the entirety of which is herein incorporated by reference), and the chlorophyll a/b binding protein gene promoter, etc.

A variety of promoters specifically active in vegetative tissues, such as leaves, stems, roots and tubers, can be used to express the nucleic acid molecules of the present invention. Examples of tuber-specific promoters include, but are not limited to the class I and II patatin promoters (Bevan et al., EMBO J. 8: 1899-1906, 1986); Koster-Topfer et al., Mol Gen Genet. 219: 390-396, 1989); Mignery et al., Gene 62:27-44, 1988); Jefferson et al., Plant Mol. Biol. 14: 995-1006, 1990), herein incorporated by reference in their entireties), the promoter for the potato tuber ADPGPP genes, both the large and small subunits; the sucrose synthase promoter (Salanoubat and Belliard, Gene 60:47-56, 1987), Salanoubat and Belliard, Gene 84:181-185, 1989), herein incorporated by reference in their entirety); and the promoter for the major tuber proteins including the 22 kd protein complexes and proteinase inhibitors (Hannapel, Plant Physiol. 101: 703-704, 1993), herein incorporated by reference in its entirety). Examples of leaf-specific promoters include but are not limited to the ribulose biphosphate carboxylase (RbcS or RuBISCO) promoters (see, e.g., Matsuoka et al., Plant J. 6:311-319, 1994), herein incorporated by reference in its entirety); the light harvesting chlorophyll a/b binding protein gene promoter (see, e.g., Shiina et al., Plant Physiol. 115:477-483, 1997; Casal et al., Plant Physiol. 116:1533-1538, 1998, herein incorporated by reference in their entireties); and the *Arabidopsis thaliana* myb-related gene promoter (Atmyb5) (Li et al., FEBS Lett. 379:117-121, 1996, herein incorporated by reference in its entirety). Examples of root-specific promoter include but are not limited to the promoter for the acid chitinase gene (Samac et al., Plant Mol. Biol. 25:587-596, 1994), herein incorporated by reference in its entirety); the root specific subdomains of the CaMV35S promoter that have been identified (Lam et al., Proc. Natl. Acad. Sci. (U.S.A.) 86:7890-7894, 1989, herein incorporated by reference in its entirety); the ORF13 promoter from *Agrobacterium rhizogenes* which exhibits high activity in roots (Hansen et al., Mol. Gen. Genet. 254:337-343, 1997), herein incorporated by reference in its entirety); the promoter for the tobacco root-specific gene RB7 (U.S. Pat. No. 5,750,386; Yamamoto et al., Plant Cell 3:371-382, 1991, herein incorporated by reference in its entirety); and the root cell specific promoters reported by Conkling et al. (Conkling et al., Plant Physiol. 93:1203-1211, 1990, herein incorporated by reference in its entirety), and the POX1 (Pox1, pox1) promoter (Hertig, et al. Plant Mol. Biol. 16:171, 1991).

Another class of useful vegetative tissue-specific promoters are meristematic (root tip and shoot apex) promoters. For example, the "SHOOTMERISTEMLESS" and "SCARECROW" promoters, which are active in the developing shoot or root apical meristems (Di Laurenzio et al., Cell 86:423-433, 1996; Long, Nature 379:66-69, 1996); herein incorporated by reference in their entireties), can be used. Another example of a useful promoter is that which controls the expression of 3-hydroxy-3-methylglutaryl coenzyme A reductase HMG2 gene, whose expression is restricted to meristematic and floral (secretory zone of the stigma, mature pollen grains, gynoecium vascular tissue, and fertilized ovules) tissues (see, e.g., Enjuto et al., Plant Cell. 7:517-527, 1995, herein incorporated by reference in its entirety). Also another example of a useful promoter is that which controls the expression of knl-related genes from maize and other species which show meristem-specific expression (see, e.g., Granger et al, Plant Mol. Biol. 31:373-378, 1996; Kerstetter et al., Plant Cell 6:1877-1887, 1994; Hake et al., Philos. Trans. R. Soc. Lond. B. Biol. Sci. 350:45-51, 1995, herein incorporated by reference in their entireties). Another example of a meristematic promoter is the *Arabidopsis thaliana* KNAT1 promoter. In the shoot apex, KNAT1 transcript is localized primarily to the shoot apical meristem; the expression of KNAT1 in the shoot meristem decreases during the floral transition and is restricted to the cortex of the inflorescence stem (see, e.g., Lincoln et al., Plant Cell 6:1859-1876, 1994, herein incorporated by reference in its entirety).

Suitable seed-specific and seed enhanced promoters can be derived from the following genes: MAC1 from maize (Sheridan et al., Genetics 142:1009-1020, 1996, herein incorporated by reference in its entirety); Cat3 from maize (Genbank No. L05934, Abler et al., Plant Mol. Biol. 22:10131-1038, 1993, herein incorporated by reference in its entirety); vivparous-1 from *Arabidopsis* (Genbank No. U93215); Atmyc1 from *Arabidopsis* (Urao et al., Plant Mol. Biol. 32:571-57, 1996; Conceicao et al., Plant 5:493-505, 1994, herein incorporated by reference in their entireties); napA from *Brassica napus* (GenBank No. J02798); the napin gene family from *Brassica napus* (Sjodahl et al., Planta 197:264-271, 1995, herein incorporated by reference in its entirety).

The ovule-specific promoter for BEL1 gene (Reiser et al. Cell 83:735-742, 1995, Genbank No. U39944; Ray et al, Proc. Natl. Acad. Sci. USA 91:5761-5765, 1994, all of which are herein incorporated by reference in their entireties) can also be used. The egg and central cell specific MEA (FIS1) and FIS2 promoters are also useful reproductive tissue-specific promoters (Luo et al., Proc. Natl. Acad. Sci. USA, 97:10637-10642, 2000; Vielle-Calzada, et al., Genes Dev. 13:2971-2982, 1999; herein incorporated by reference in their entireties).

A maize pollen-specific promoter has been identified in maize (Guerrero et al., Mol. Gen. Genet. 224:161-168, 1990, herein incorporated by reference in its entirety). Other genes specifically expressed in pollen have been described (see, e.g., Wakeley et al., Plant Mol. Biol. 37:187-192, 1998; Ficker et al., Mol. Gen. Genet. 257:132-142, 1998; Kulikauskas et al., Plant Mol. Biol. 34:809-814, 1997; Treacy et al., Plant Mol. Biol. 34:603-611, 1997; all of which are herein incorporated by reference in their entireties).

Promoters derived from genes encoding embryonic storage proteins, which includes the gene encoding the 2S storage protein from *Brassica napus* (Dasgupta et al, Gene 133:301-302, 1993, herein incorporated by reference in its entirety); the 2s seed storage protein gene family from *Arabidopsis*; the gene encoding oleosin 2010 from *Brassica napus* (GenBank No. M63985); the genes encoding oleosin A (Genbank No. U09118) and oleosin B (GenBank No. U09119) from soybean; the gene encoding oleosin from *Arabidopsis* (GenBank No. Z17657); the gene encoding oleosin 18 kD from maize (GenBank No. J05212, Lee, Plant Mol. Biol. 26:1981-1987, 1994), herein incorporated by reference in its entirety); and the gene encoding low molecular weight sulphur rich protein from soybean (Choi et al., Mol. Gen. Genet. 246:266-268, 1995, herein incorporated by reference in its entirety), can also be used.

Promoters derived from zein encoding genes (including the 15 kD, 16 kD, 19 kD, 22 kD, 27 kD, and gamma genes; Pedersen et al., Cell 29:1015-1026, 1982, herein incorporated by reference in its entirety) can be also used. The zeins are a group of storage proteins found in maize endosperm.

Other promoters known to function, for example, in maize, include the promoters for the following genes: waxy, Brittle, Shrunken 2, Branching enzymes I and II, starch synthases, debranching enzymes, oleosins, glutelins, and sucrose synthases. A particularly preferred promoter for maize endosperm expression is the promoter for the glutelin gene from rice, more particularly the Osgt-1 promoter (Zheng et al., Mol. Cell Biol. 13:5829-5842, 1993, herein incorporated by reference in its entirety). Examples of promoters suitable for expression in wheat include those promoters for the ADPglucose pyrophosphorylase (ADPGPP) subunits, the granule bound and other starch synthases, the branching and debranching enzymes, the embryogenesis-abundant proteins, the gliadins, and the glutenins. Examples of such promoters in rice include those promoters for the ADPGPP subunits, the granule bound and other starch synthases, the branching enzymes, the debranching enzymes, sucrose synthases, and the glutelins. A particularly preferred promoter is the promoter for rice glutelin, Osgt-1. Examples of such promoters for barley include those for the ADPGPP subunits, the granule bound and other starch synthases, the branching enzymes, the debranching enzymes, sucrose synthases, the hordeins, the embryo globulins, and the aleurone specific proteins.

A tomato promoter active during fruit ripening, senescence and abscission of leaves and, to a lesser extent, of flowers can be used (Blume et al., Plant J. 12:731-746, 1997, herein incorporated by reference in its entirety). Other exemplary promoters include the pistol specific promoter in the potato (*Solanum tuberosum* L.) SK2 gene, encoding a pistil-specific basic endochitinase (Ficker et al., Plant Mol. Biol. 35:425-431, 1997, herein incorporated by reference in its entirety); the Blec4 gene from pea (*Pisum sativum* cv. Alaska), active in epidermal tissue of vegetative and floral shoot apices of transgenic alfalfa. This makes it a useful tool to target the expression of foreign genes to the epidermal layer of actively growing shoots. The tissue specific E8 promoter from tomato is also useful for directing gene expression in fruits (Deikman, et al., Plant Physiology 100:2013-2017, 1992).

It is further recognized that since in most cases the exact boundaries of regulatory sequences have not been completely defined, DNA fragments of different lengths may have identical promoter activity.

Promoters that are known or are found to cause transcription of DNA in plant cells can be used in the present invention. Such promoters may be obtained from a variety of sources such as plants and plant viruses. In addition to promoters that are known to cause transcription of DNA in plant cells, other promoter molecules may be identified for use in the current invention by screening a plant cDNA library for genes that are selectively or preferably expressed in the target tissues or cells and isolating the 5' genomic region of the identified cDNAs.

Constructs or vectors may also include with the coding region of interest a polynucleic acid that acts, in whole or in part, to terminate transcription of that region. For example, such sequences have been isolated including the Tr7 3' sequence and the nos 3' sequence (Ingelbrecht et al., The Plant Cell 1:671-680, 1989, the entirety of which is herein incorporated by reference; Bevan et al., Nucleic Acids Res. 11:369-385, 1983, the entirety of which is herein incorporated by reference).

A vector or construct may also include regulatory elements. Examples of such include the Adh intron 1 (Callis et al., Genes and Develop. 1:1183-1200, 1987, the entirety of which is herein incorporated by reference), the sucrose synthase intron (Vasil et al., Plant Physiol. 91:1575-1579, 1989, the entirety of which is herein incorporated by reference) and the TMV omega element (Gallie et al., Plant Cell 1:301-311, 1989, the entirety of which is herein incorporated by reference). These and other regulatory elements may be included when appropriate.

A vector or construct may also include a selectable marker. Selectable markers may also be used to select for plants or plant cells that contain the exogenous genetic material. Examples of such include, but are not limited to, a neo gene (Potrykus et al., Mol. Gen. Genet. 199:183-188, 1985, the entirety of which is herein incorporated by reference) which codes for kanamycin resistance and can be selected for using kanamycin, G418, etc.; a bar gene that provides for bialaphos resistance; a mutant EPSP synthase gene (Hinchee et al., Bio/Technology 6:915-922 (1988), the entirety of which is herein incorporated by reference) that provide for glyphosate resistance; a nitrilase gene that provides for resistance to bromoxynil (Stalker et al., *J. Biol. Chem.* 263:6310-6314 (1988), the entirety of which is herein incorporated by reference); a mutant acetolactate synthase gene (ALS) which confers imidazolinone or sulphonylurea; and a methotrexate resistant DHFR gene (Thillet et al., *J. Biol. Chem.* 263:12500-12508, 1988, the entirety of which is herein incorporated by reference).

A vector or construct may also include a screenable marker. Screenable markers may be used to monitor expression. Exemplary screenable markers include a β-glucuronidase or uidA gene (GUS) which encodes an enzyme for which various chromogenic substrates are known (Jefferson, Plant Mol. Biol, Rep. 5:387-405 (1987), the entirety of which is herein incorporated by reference; Jefferson et al., EMBO J. 6:3901-3907 (1987), the entirety of which is herein incorporated by reference); an R-locus gene, which encodes a product that regulates the production of anthocyanin pigments (red color) in plant tissues (Dellaporta et al., Stadler Symposium 11:263-282 (1988), the entirety of which is herein incorporated by reference); a β-lactamase gene (Sutcliffe et al., Proc. Natl. Mad. Sci. (U.S.A.) 75:3737-3741 (1978), the entirety of which is herein incorporated by reference), a gene which encodes an enzyme for which various chromogenic substrates are known (e.g., PADAC, a chromogenic cephalosporin); a luciferase gene (Ow et al., Science 234:856-859 (1986), the entirety of which is herein incorporated by reference); a xylE gene (Zukowsky et al., Proc. Natl. Acad. Sci. (U.S.A.) 80:1101-1105 (1983), the entirety of which is herein incorporated by reference) which encodes a catechol dioxygenase that can convert chromogenic catechols; an α-amylase gene (Ikatu et al., Bio/Technol. 8:241-242, 1990, the entirety of which is herein incorporated by reference); a tyrosinase gene (Katz et al., J. Gen. Microbiol. 129:2703-2714, 1983, the entirety of which is herein incorporated by reference) which encodes an enzyme capable of oxidizing tyrosine to DOPA and dopaquinone which in turn condenses to melanin; and an α-galactosidase.

Introduction of Polynucleotides into Plants

There are many methods for introducing transforming nucleic acid molecules into plant cells. Suitable methods are believed to include virtually any method by which nucleic acid molecules may be introduced into a cell, such as by *Agrobacterium* infection or direct delivery of nucleic acid molecules such as, for example, by PEG-mediated transformation, by electroporation or by acceleration of DNA coated particles, etc. (Potrykus, Ann. Rev. Plant Physiol. Plant Mol. Biol. 42:205-225 (1991), the entirety of which is herein incorporated by reference; Vasil, Plant Mol. Biol. 25:925-937 (1994), the entirety of which is herein incorporated by reference). For example, electroporation has been used to transform *Zea mays* protoplasts (Fromm et al., Nature 312:791-793, 1986, the entirety of which is herein incorporated by reference).

Other vector systems suitable for introducing transforming DNA into a host plant cell include but are not limited to binary artificial chromosome (BIBAC) vectors (Hamilton et al., Gene 200:107-116, 1997, the entirety of which is herein incorporated by reference), and transfection with RNA viral vectors (Della-Cioppa et al., Ann. N.Y. Acad. Sci. (1996), 792 pp Engineering Plants for Commercial Products and Applications, pp 57-61, the entirety of which is herein incorporated by reference.

Technology for introduction of DNA into cells is well known to those of skill in the art. Four general methods for delivering a gene into cells have been described: (1) chemical methods (Graham and van der Eb, Virology 54:536-539, 1973, the entirety of which is herein incorporated by reference); (2) physical methods such as microinjection (Capecchi, *Cell* 22:479-488 (1980), the entirety of which is herein incorporated by reference), electroporation (Wong and Neumann, Biochem. Biophys. Res. Commun. 107:584-587

(1982); Fromm et al., Proc. Natl. Acad. Sci. (U.S.A.) 82:5824-5828 (1985); U.S. Pat. No. 5,384,253, all of which are herein incorporated in their entirety); and the gene gun (Johnston and Tang, Methods Cell Biol. 43:353-365 (1994), the entirety of which is herein incorporated by reference); (3) viral vectors (Clapp, Clin. Perinatol. 20:155-168, 1993; Lu et al., J. Exp. Med. 178:2089-2096, 1993; Eglitis and Anderson, *Biotechniques* 6:608-614, 1988, all of which are herein incorporated in their entirety); and (4) receptor-mediated mechanisms (Curiel et al., Hum. Gen. Ther. 3:147-154, 1992, Wagner et al., Proc. Natl. Acad. Sci. USA 89:6099-6103, 1992, all of which are incorporated by reference in their entirety).

Acceleration methods that may be used include, for example, microprojectile bombardment and the like. One example of a method for delivering transforming nucleic acid molecules to plant cells is microprojectile bombardment. This method has been reviewed by Yang and Christou, eds., Particle Bombardment Technology for Gene Transfer, Oxford Press, Oxford, England (1994), the entirety of which is herein incorporated by reference. Non-biological particles (microprojectiles) that may be coated with nucleic acids and delivered into cells by a propelling force. Exemplary particles include those comprised of tungsten, gold, platinum, and the like.

*Agrobacterium*-mediated transfer is a widely applicable system for introducing genes into plant cells because the DNA can be introduced into whole plant tissues, thereby bypassing the need for regeneration of an intact plant from a protoplast. The use of *Agrobacterium*-mediated plant integrating vectors to introduce DNA into plant cells is well known in the art. See, for example the methods described by Fraley et al., Bio/Technology 3:629-635 (1985) and Rogers et al., Methods Enzymol. 153:253-277 (1987), both of which are herein incorporated by reference in their entirety. Further, the integration of the Ti-DNA is a relatively precise process resulting in few rearrangements. The region of DNA to be transferred is defined by the border sequences, and intervening DNA is usually inserted into the plant genome as described (Spielmann et al., Mol. Gen. Genet. 205:34 (1986), the entirety of which is herein incorporated by reference).

A transgenic plant resulting from *Agrobacterium* transformation methods frequently contains a single gene on one chromosome. Such transgenic plants can be referred to as being hemizygous for the added gene. More preferred is a transgenic plant that is homozygous for the added structural gene; i.e., a transgenic plant that contains two added genes, one gene at the same locus on each chromosome of a chromosome pair. A homozygous transgenic plant can be obtained by sexually mating (selfing) an independent segregant transgenic plant that contains a single added gene, germinating some of the seed produced and analyzing the resulting plants produced for the gene of interest.

It is also to be understood that two different transgenic plants can also be mated to produce offspring that contain two independently segregating added, exogenous genes. Selfing of appropriate progeny can produce plants that are homozygous for both added, exogenous genes that encode a polypeptide of interest. Back-crossing to a parental plant and out-crossing with a non-transgenic plant are also contemplated, as is vegetative propagation.

The regeneration, development, and cultivation of plants from single plant protoplast transformants or from various transformed explants is well known in the art (Weissbach and Weissbach, In: *Methods for Plant Molecular Biology*, (eds.), Academic Press, Inc. San Diego, Calif., (1988), the entirety of which is herein incorporated by reference). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous gene that encodes a protein of interest is well known in the art. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired polypeptide is cultivated using methods well known to one skilled in the art.

The present invention also provides for parts of the plants of the present invention. Plant parts, without limitation, include seed, endosperm, ovule and pollen. In a particularly preferred embodiment of the present invention, the plant part is a seed.

Methods for transforming dicots, primarily by use of *Agrobacterium tumefaciens*, and obtaining transgenic plants have been published, e.g., cotton (U.S. Pat. Nos. 5,004,863, 5,159,135, 5,518,908, all of which are herein incorporated by reference in their entirety), soybean (U.S. Pat. No. 5,569,834, the entirety of which is herein incorporated by reference) and *Brassica* (U.S. Pat. No. 5,463,174, the entirety of which is herein incorporated by reference).

Transformation of monocotyledons using electroporation, particle bombardment, and *Agrobacterium* have also been reported. For example, transformation and plant regeneration have been achieved in asparagus, barley, *Zea mays* (Fromm et al., Bio/Technology 8:833 (1990), Armstrong et al., Crop Science 35:550-557 (1995), all of which are herein incorporated by reference in their entirety); oat; rice, rye, sugarcane; tall fescue and wheat (U.S. Pat. No. 5,631,152, the entirety of which is herein incorporated by reference.)

In addition to the above discussed procedures, practitioners are familiar with the standard resource materials which describe specific conditions and procedures for the construction, manipulation and isolation of macromolecules (e.g., DNA molecules, plasmids, etc.), generation of recombinant organisms and the screening and isolating of clones, (see for example, Sambrook et al., *Molecular Cloning: A Laboratory Manual*, Cold Spring Harbor Press (1989); Mailga et al., *Methods in Plant Molecular Biology*, Cold Spring Harbor Press (1995), the entirety of which is herein incorporated by reference; Birren et al., *Genome Analysis: Detecting Genes*, 1, Cold Spring Harbor, N.Y. (1998), the entirety of which is herein incorporated by reference; Birren et al., *Genome Analysis: Analyzing DNA*, 2, Cold Spring Harbor, N.Y. (1998), the entirety of which is herein incorporated by reference; *Plant Molecular Biology: A Laboratory Manual*, eds. Clark, Springer, New York (1997), the entirety of which is herein incorporated by reference).

Having now generally described the invention, the same will be more readily understood through reference to the following examples, which are provided by way of illustration, and are not intended to be limiting of the present invention, unless specified.

EXAMPLES

Example 1

When an isolated native plant polynucleotide comprising a coding sequence is reconstructed as a transgene, then introduced into the plant by methods of plant transformation there is a risk that expression from the endogenous homologous plant gene will interact negatively with the transgene. To avoid these negative interactions it may be necessary to provide a transgene polynucleotide substantially divergent in sequence from the native plant gene. An artificial polynucleotide molecule can be produced by the method of the present invention and used to reduce the occurrence of transgene silencing.

This example serves to illustrate methods of the present invention that result in the production of a polynucleotide encoding a modified plant EPSP synthase. The native rice (*Oryzae sativa*) EPSPS enzyme and chloroplast transit peptide is used to construct an artificial polynucleotide molecule that also includes codons that encode for substituted amino acids that do not naturally occur in the rice EPSPS enzyme. These substituted amino acids provide for a glyphosate resistant rice EPSPS enzyme (OsEPSPS_TIPS, SEQ ID NO:1).

The steps described in Table 6 are used to construct such an artificial polynucleotide sequence (OsEPSPS_AT, SEQ ID NO:3) using an *Arabidopsis* codon usage table and the parameters for construction of a substantially divergent polynucleotide molecule, which when expressed in plants encodes a modified rice EPSPS enzyme resistant to glyphosate herbicide. The comparison of the native rice EPSPS gene sequence referred to as OsEPSPS_Nat (SEQ ID NO:2) that has previously been modified to encode a glyphosate resistant enzyme to the polynucleotide molecule modified for *Arabidopsis* codon usage, OsEPSPS_AT (SEQ ID NO: 3) and to the sequence modified for *Zea mays* codon usage, OsEPSPS_ZM (SEQ ID NO: 4) by this method is shown in FIG. 1. FIG. 1 shows nucleotide bases changed in the modified polynucleotides compared to OsEPSPS_Nat, SEQ ID NO: 2.

TABLE 6

| Polynucleotide design for a modified rice EPSP synthase (OsEPSPS_AT) |
|---|
| 1. Substitute amino acids at positions 173 and 177 to provide a modified rice EPSPS enzyme resistant to glyphosate herbicide shown in SEQ ID NO: 1. |
| 2. Back translate SEQ ID NO: 1 to generate an artificial polynucleotide sequence using the *Arabidopsis thaliana* codon usage table (Table 2). |
| 3. Perform sequence alignment with native OsEPSPS polynucleotide sequence (SEQ ID NO: 2) and the artificial polynucleotide sequence to determine degree of sequence identity, map open reading frames, select patterns to search and identify restriction enzymes recognition sequences. |
| 4. Make corrections to the codons used in the artificial polynucleotide sequence to achieve desired percentage of sequence identity and to avoid clustering of identical codons. This is especially important for amino acids that are occur at high frequency, i.e., alanine, glycine, histidine, leucine, serine, and valine. Approximate distribution of codon usage in the polynucleotide sequence according to the *Arabidopsis* codon usage, Table 2. |
| 5. The polynucleotide sequence is inspected for local regions that have a GC:AT ratio higher than about 2 over a range of about 50 contiguous nucleotides. The polynucleotide sequence is adjusted as necessary, by substituting codons in these regions such that the local GC:AT ratio is less than about 2 and the entire polynucleotide composition is in the range of 0.9-1.3. |
| 6. Introduce stop codons to translation frames "b", "c", "d", "e" and "f". Translation stop codons are created in the "b", "c", "d", "e" and "f" translational frames by replacing one or more codons within about 130 base pairs (bps) of the ends of the artificial polynucleotide that creates a stop codon without changing the amino acid coding sequence of frame one. |
| 7. Eliminate ATG codons from forward (frames "b" and "c") and reverse open reading frames (frame "d", "e", "f"). The forward and reverse reading frames are inspected for the presence of ATG codons. Any ATG codons in frame "b" and "c" found in the polynucleotide sequence before third Met in frame "a" of the polynucleotide are eliminated by replacing one or more codons that overlap the ATG changing one of the nucleotides without changing the amino acid coding sequence of frame "a". In the reverse frames, replacement of ATG or stop codon introduction may be done to interrupt potential reading frames. |
| 8. Eliminate unwanted restriction enzyme recognition patterns and other specific patterns (polyadenylation, RNA splicing, sequence instability patterns). The polynucleotide sequence is inspected for the presence of any unwanted polynucleotide patterns and the patterns are disrupted by substituting codons in these regions. |
| 9. Check sequence identity between a first polynucleotide and the artificial polynucleotide created by the method of the present invention. Eliminate sequence identity in a contiguous polynucleotide that is longer than 23 bps. It is desirable to eliminate sequence identity greater than about 15 bps. It is helpful to select from amino acids such as, serine, arginine, and leucine that have 6 codons or from amino acids with 4 codons to eliminate sequence identity. |
| 10. Review the artificial polynucleotide sequence resulting from anyone of steps 1 to 9 for any of the sequence features identified in steps 4-9, and if the sequence does not comply with conditions make additional codon substitutions to the sequence until the conditions of steps 4-9 are met. |
| 11. Construct the artificial polynucleotide molecule by methods known in the art, e.g., using PCR with a mixture of overlapping primers. The primers at the ends of the gene may contain convenient restriction sites to allow easy cloning of the gene to selected vector. At the 5' end usually AlfIII, BspHI, NcoI, NdeI, PciI, or SphI are most convenient in as much as their sequence contains an ATG start codon, however other enzymes can be used as well if a modified polynucleotide is designed to create a fusion with another polynucleotide segment, e.g., chloroplast transit peptide and EPSPS coding sequence. |

TABLE 6-continued

Polynucleotide design for a modified rice EPSP synthase (OsEPSPS_AT)

12. Perform a DNA sequence analysis of the artificial polynucleotide to confirm the synthetic construction resulted in the desired polynucleotide molecule. If errors are found, then eliminate these by site directed mutagenesis for which many methods are known to those skilled in the art of DNA mutagenesis.

A *Zea mays* codon usage (*Zea mays*, Table 3) version of the glyphosate resistant rice EPSPS enzyme sequence (*Oryzae sativa* EPSPS enzyme with TIPS mutations, SEQ ID NO:1) is made. The polynucleotide that encodes this enzyme includes codons that encode for substituted amino acids that do not naturally occur in the native rice EPSPS enzyme. These substituted amino acids provide for a glyphosate resistant rice EPSPS enzyme. The steps described in Table 7 are used to construct a modified artificial polynucleotide sequence (OsEPSPS_ZM, SEQ ID NO:4) based on a *Zea mays* codon usage table that encodes a modified rice EPSPS enzyme resistant to glyphosate herbicide. The comparison of the OsEPSPS_Nat polynucleotide sequence (SEQ ID NO:2) to the OsEPSPS_ZM artificial polynucleotide sequence (SEQ ID NO:4) using the *Zea mays* codon usage is shown in FIG. 2.

TABLE 7

| Polynucleotide construction for modified rice EPSP synthase (OsEPSPS_ZM) |
|---|
| 1. Back translate SEQ ID NO: 1 to generate an artificial polynucleotide sequence using the *Zea mays* codon usage table (Table 3). |
| 2. Perform sequence alignment with the native OsEPSPS polynucleotide sequence (SEQ ID NO: 2) and the artificial polynucleotide sequence to determine degree of sequence identity, map open reading frames, select patterns to search and identify restriction enzymes recognition sequences. |
| 3. Make corrections to the codons used in the artificial polynucleotide sequence to achieve desired percentage of sequence identity and to avoid clustering of identical codons. This is especially important for amino acids that are occur at high frequency, i.e., alanine, glycine, histidine, leucine, serine, and valine. Approximate distribution of codon usage in the polynucleotide sequence according to the *Zea mays* codon usage, Table 3. |
| 4. The polynucleotide sequence is inspected for local regions that have a GC:AT ratio higher than about 2 over a range of about 50 contiguous nucleotides. The polynucleotide sequence is adjusted as necessary, by substituting codons in these regions such that the local GC:AT ratio is less than about 2 and the entire polynucleotide composition is in the range of 1.2-1.7. |
| 5. Follow steps 6-12 of Table 6. |

TABLE 8

Sequence percent identity between OsEPSPS polynucleotides.

| | OsEPSPS_ZM | OsEPSPS_AT | OsEPSPS_Nat |
|---|---|---|---|
| OsEPSPS_ZM | 100.00 | 73.51 | 71.58 |
| OsEPSPS_AT | | 100.00 | 74.03 |
| OsEPSPS_Nat | | | 100.00 |

TABLE 9

The nucleotide composition and GC:AT ratio of the modified polynucleotide sequences for the rice EPSPS gene sequence.

| | A | C | G | T | GC:AT |
|---|---|---|---|---|---|
| OsEPSPS_AT | 377 | 336 | 444 | 391 | 1.02 |
| OsEPSPS_ZM | 365 | 381 | 470 | 332 | 1.22 |

The two rice EPSPS artificial polynucleotide sequences (SEQ ID NO:3 and SEQ ID NO:4) are modified such that the percent identity is below 75 percent compared to SEQ ID NO:2 or relative to each other (Table 8). The nucleotide composition and GC:AT ratio of the polynucleotide sequences for the rice EPSPS gene sequence are shown in Table 9. These polynucleotides can be selected for use in plant expression constructs together with different regulatory elements or they can be combined in a single plant by retransformation with a DNA construct or by methods of plant breeding. Concerns with gene silencing and recombination are reduced when DNA constructs have reduced levels of homologous DNA.

Example 2

Corn (*Zea mays*) has been genetically modified to have resistance to glyphosate herbicide (U.S. Pat. No. 6,040,497). These corn plants contain a transgene with a corn EPSP synthase modified for glyphosate tolerance. The methods of the present invention can be used to construct a new artificial polynucleotide encoding a corn EPSP synthase that is substantially different in percent identity to the endogenous corn EPSP synthase gene. The newly constructed corn EPSP synthase artificial polynucleotide can be used as a selectable marker during the selection of transgenic plant lines that may contain additional transgenic agronomic traits. During hybrid corn seed production, it is useful to have both parents glyphosate tolerant using non-interfering transgenes.

TABLE 10

| Polynucleotide construction for modified corn EPSP synthase (ZmEPSPS_ZM, SEQ ID NO: 10) |
|---|
| 1. Back translate SEQ ID NO: 8 to generate a polynucleotide sequence using the *Zea mays* codon usage table (Table 3). |
| 2. Perform sequence alignment with ZmEPSPS_Nat polynucleotide sequence (SEQ ID NO: 9) and the artificial polynucleotide sequence to determine degree of sequence identity, map open reading frames, select patterns to search and identify restriction enzymes recognition sequences. |
| 3. Make corrections to the codons used in the artificial polynucleotide sequence to achieve desired percentage of sequence identity and to avoid clustering of identical codons. This is especially important for amino acids that are occur at high frequency, i.e., alanine, glycine, histidine, leucine, serine, and valine. Approximate distribution of codon usage in the polynucleotide sequence according to the *Zea mays* codon usage, Table 3. |

TABLE 10-continued Polynucleotide construction for modified corn
EPSP synthase (ZmEPSPS_ZM, SEQ ID NO: 10)

4. The artificial polynucleotide sequence is inspected for local regions that have a GC:AT ratio higher than about 2 over a range of about 50 contiguous nucleotides. The polynucleotide sequence is adjusted as necessary, by substituting codons in these regions such that the local GC:AT ratio is less than about 2 and the entire polynucleotide composition is in the range of 1.2-1.7.
5. Follow steps 6-12 of Table 6.

TABLE 11

Sequence percent identity between ZmEPSPS polynucleotides.

|  | ZmEPSPS_ZM | ZmEPSPS_Nat |
| --- | --- | --- |
| ZmEPSPS_ZM | 100.00 | 74.81 |
| ZmEPSPS_Nat |  | 100.00 |

Maize EPSPS gene nucleotide sequence is also modified to reduce identity between synthetic and native gene and maintain overall GC:AT ratio typical for monocots. The GC:AT ratio for the ZmEPSPS_ZM sequence is 1.38. The sequence identity is reduced to about 75% between native (ZmEPSPS_Nat, SEQ ID NO:9) and synthetic (ZmEPSPS_ZM, SEQ ID NO:10).

The comparison of native polynucleotides encoding EPSPS indicate that the chloroplast transit peptide is the most divergent fragment of the gene. Similarity in nucleotide sequence of mature peptides is higher than 88% for maize and rice enzymes, and some conserved regions have sequence identity as long as 50 bps. Posttranscriptional gene silencing has been observed for sequences as small as 60 polynucleotides (Sijen et al., Plant Cell, 8:2277-2294, 1996; Mains, Plant Mol. Biol. 43:261-273, 2000).

Example 3

Soybean (*Glycine max*) has been genetically modified to be tolerant to glyphosate by expression of a class II EPSPS isolated from *Agrobacterium* (Padgette et al. Crop Sci. 35:1451-1461, 1995). A soybean native EPSPS gene sequence has been identified and an artificial polynucleotide sequence designed using the method of the present invention. The artificial polynucleotide encodes a protein sequence that is modified to produce a glyphosate resistant EPSPS enzyme (GmEPSPS_IKS, SEQ ID NO:5) by replacing amino acids T to I, R to K and P to S within the GNAGTAMRP motif, resulting in a modified soybean EPSPS enzyme with the motif GNAGIAMKS (SEQ ID NO:34), also referred to as IKS mutant. Expression of a modified to EPSPS enzyme in the cells of a plant by transformation with a transgene plant expression cassette, which contains a polynucleotide encoding the modified EPSPS with the motif GNAGIAMKS will confer glyphosate tolerance to the plants. Additional amino acid substitutions for the arginine (R) in the motif can also include asparagine (N).

TABLE 12

Polynucleotide construction for modified soybean
EPSP synthase gene (GmEPSPS_GM, SEQ ID NO: 7).

1. Back translate SEQ ID NO: 5 to generate an artificial polynucleotide sequence using the *Glycine max* codon usage table (Table 4).

TABLE 12-continued

Polynucleotide construction for modified soybean
EPSP synthase gene (GmEPSPS_GM, SEQ ID NO: 7).

2. Perform sequence alignment with GmEPSPS_Nat polynucleotide sequence (SEQ ID NO: 6) and the artificial polynucleotide sequence to determine degree of sequence identity, map open reading frames, select patterns to search and identify restriction enzymes recognition sequences.
3. Make corrections to the codons used in the artificial polynucleotide sequence to achieve desired percentage of sequence identity and to avoid clustering of identical codons. This is especially important for amino acids that are occur at high frequency, i.e., alanine, glycine, histidine, leucine, serine, and valine. Approximate distribution of codon usage in the polynucleotide sequence according to the *Glycine max* codon usage, Table 4.
4. The polynucleotide sequence is inspected for local regions that have a GC:AT ratio higher than about 2 over a range of about 50 contiguous nucleotides. The polynucleotide sequence is adjusted as necessary, by substituting codons in these regions such that the local GC:AT ratio is less than about 2 and the entire polynucleotide composition is in the range of 0.9-1.3.
5. Follow steps 6-12 of Table 6.

TABLE 13

Comparison of the sequence percent identity of the
modified GmEPSPS at polynucleotide sequence level.

|  | GmEPSPS_GM | GmEPSPS_Nat |
| --- | --- | --- |
| GmEPSPS_GM | 100.00 | 72.43 |
| GmEPSPS_Nat |  | 100.00 |

The soybean native EPSPS gene is modified using a soybean codon table (Table 4) and the conditions of the method of the present invention. The relative ratio of GC:AT is not changed in the modified gene, however the sequence identity between the two is reduced to 72%.

Example 4

The native aroA polynucleotide gene isolated from *Agrobacterium* strain CP4 (U.S. Pat. No. 5,633,435, herein incorporated by reference in its entirety) that encodes a glyphosate resistant EPSP synthase (SEQ ID NO:15) can be modified by the method of the present invention to provide a polynucleotide that has the codon usage of *Arabidopsis, Zea mays*, or *Glycine max*. For the appropriate expression of CP4EPSPS to confer glyphosate tolerance in plants, a chloroplast transit peptide is necessarily fused to the CP4EPSPS coding sequence to target accumulation of the enzyme to the chloroplasts. The CTP2 chloroplast transit peptide is commonly used for the expression of this gene in transgenic plants (Nida et al., J. Agric, Food Chem. 44:1960-1966, 1996). The sequence of CP4EPSPS together with CTP2 polynucleotide (SEQ ID NO:11) have been modified by the method of the present invention. Other chloroplast transit peptides known in the art can be fused to the CP4EPSPS to direct the enzyme to the chloroplasts.

TABLE 14

Polynucleotide construction for aroA:CP4
EPSP synthase coding sequence (CP4EPSPS_AT,
CP4EPSPS_ZM, or CP4EPSPS_GM)

1. Place CTP2 transit peptide sequence (SEQ ID NO: 11) in front of CP4EPSPS (SEQ ID NO: 15) as a fusion polypeptide. Back translate the fusion polypeptide to produce an artificial polynucleotide sequence using the *Arabidopsis thaliana* codon usage table (Table 2), or the *Zea mays* codon usage table (Table 3), or the *Glycine max* codon usage table (Table 4).

TABLE 14-continued

Polynucleotide construction for aroA:CP4
EPSP synthase coding sequence (CP4EPSPS_AT,
CP4EPSPS_ZM, or CP4EPSPS_GM)

2. Perform sequence alignment with native CTP2 (SEQ ID NO: 12) and native CP4EPSPS polynucleotide sequence(SEQ ID NO: 16) and the artificial polynucleotide sequence to determine degree of sequence identity, map open reading frames, select patterns to search and identify restriction enzymes recognition sequences.
3. Make corrections to the codons used in the artificial polynucleotide sequence to achieve desired percentage of sequence identity and to avoid clustering of identical codons. This is especially important for amino acids that are occur at high frequency, i.e., alanine, glycine, histidine, leucine, serine, and valine. Approximate distribution of codon usage in the polynucleotide sequence according to the *Arabidopsis thaliana* codon usage, Table 2, or the *Zea mays* codon usage table (Table 3) depending on the table in use.
4. The artificial polynucleotide sequence is inspected for local regions that have a GC:AT ratio higher than about 2 over a range of about 50 contiguous nucleotides. The polynucleotide sequence is adjusted as necessary, by substituting codons in these regions such that the local GC:AT ratio is less than about 2 and the entire polynucleotide composition is in the range of 0.9-1.3 is Table 2 is used and 1.2-1.7 if Table 3 is used.
5. Follow steps 6-12 of Table 6.

polynucleotide. The GC:AT ratio in native CP4EPSPS is about 1.7. The artificial version with the *Zea mays* codon bias is produced to have a very similar GC:AT ratio. In the *Arabidopsis* codon version, the GC:AT ratio is decreased to about 1.2.

Gene expression is also a criteria for selection of transgenes to be expressed. Expression of a transgene can vary in different crop plants, therefore having several artificial polynucleotide coding sequence available for testing in different crop plants and genotypes, varieties or cultivars is an advantage and an aspect of the invention.

Example 5

The bar polynucleotide sequence (SEQ ID NO:20) encoding a phosphinothricin acetyl transferase protein (SEQ ID NO:19) has been used to genetically modify plants for resistance to glufosinate herbicide. Two new bar polynucleotide sequences have been designed using the method of the present invention. The alignment of BAR1_Nat with the two new artificial BAR1 polynucleotides is shown in FIG. 4.

TABLE 15

Comparison of the sequence percent identity of the artificial CP4EPSPS polynucleotides.

|  | CTP2CP_GM | CTP2CP4_AT | CTP2CP4_ZM | CTP2CP4_Syn | CTP2CP4_NAT |
|---|---|---|---|---|---|
| CTP2CP4_GM | 100.00 | 75.66 | 74.12 | 75.15 | 74.37 |
| CTP2CP4_AT |  | 100.00 | 76.13 | 74.56* | 72.93 |
| CTP2CP4_ZM |  |  | 100.00 | 77.76* | 82.58 |
| CTP2CP4_Syn |  |  |  | 100.00 | 82.70 |
| CTP2CP4_NAT |  |  |  |  | 100.00 |

*Percent of identity relates to the CP4EPSPS and do not include transit peptide.

TABLE 16

The nucleotide composition and GC:AT ratio of the artificial polynucleotide sequences for the CP4EPSPS gene sequence.

|  | A | C | G | T | GC:AT |
|---|---|---|---|---|---|
| CTP2CP4_GM | 382 | 375 | 442 | 397 | 1.05 |
| CTP2CP4_AT | 369 | 408 | 469 | 350 | 1.22 |
| CTP2CP4_ZM | 312 | 487 | 577 | 290 | 1.65 |

The polynucleotide sequence CTP2_Nat (SEQ ID NO:12) plus CP4EPSPS_Nat (SEQ ID NO:16) designated as CTP2CP4_Nat is compared in Table 15 to the artificial polynucleotide sequences designated as CTP2CP4_AT (CTP2_AT, SEQ ID NO:13 fused to CP4EPSPS_AT, SEQ ID NO:17) and CTP2CP4_ZM (CTP2_AT, SEQ ID NO:14 fused to CP4EPSPS_ZM, SEQ ID NO:18) produced by the method of the present invention. The polynucleotide sequence that is the most divergent from the native sequence CTP2CP4_NAT and CTP2CP4EPSPS_Syn is CTP2CP4_AT having about 73% and 75% sequence identity, respectively. The CTP2CP4_ZM polynucleotide sequence compared to CTP2CP4_Nat and CP4EPSPS_Syn has about 83% and 78% identity to these two sequences, respectively.

A primary criteria for the selection of transgenes to combine in a plant is the percent identity. Table 15 can be used to select a CP4EPSPS polynucleotide molecule for plant expression cassette construction when it is known that the recipient plant will contain more than one CP4EPSPS

TABLE 17

Polynucleotide gene construction for BAR1_AT (SEQ ID NO: 21) and BAR1_ZM (SEQ ID NO: 22)

1. Back translate SEQ ID NO: 19 to generate a polynucleotide sequence using the *Arabidopsis thaliana* codon usage table (Table 2) or the *Zea mays* codon usage table (Table 3)
2. Perform sequence alignment with native BAR1_Nat polynucleotide sequence (SEQ ID NO: 20) and the artificial polynucleotide sequence to determine degree of sequence identity, map open reading frames, select patterns to search and identify restriction enzymes recognition sequences.
3. Make corrections to the codons used in the artificial polynucleotide sequence to achieve desired percentage of sequence identity and to avoid clustering of identical codons. This is especially important for amino acids that are occur at high frequency, i.e., alanine, glycine, histidine, leucine, serine, and valine. Approximate distribution of codon usage in the polynucleotide sequence according to the *Arabidopsis thaliana* codon usage, Table 2, or the *Zea mays* codon usage table (Table 3) depending on the table in use.
4. The artificial polynucleotide sequence is inspected for local regions that have a GC:AT ratio higher than about 2 over a range of about 50 contiguous nucleotides. The polynucleotide sequence is adjusted as necessary, by substituting codons in these regions such that the local GC:AT ratio is less than about 2 and the entire polynucleotide composition is in the range of 0.9-1.3 if Table 2 is used and 1.2-1.7 if Table 3 is used.
5. Follow steps 6-12 of Table 6.

The sequence identity of artificial BAR polynucleotides is the range of 73-77% (Table 18). The native polynucleotide is highly GC rich. The artificial version (BAR1_ZM) with *Zea mays* codon bias has reduced the GC:AT ratio to about 1.3 and artificial version (BAR1_AT) with *Arabidopsis* codon bias the ratio is about 1.0 (Table 19).

TABLE 18

Sequence percent identity between bar genes at the polynucleotide sequence level.

|  | BAR1_ZM | BAR1_AT | BAR1_Nat |
|---|---|---|---|
| BAR1_ZM | 100.00 | 77.35 | 76.99 |
| BAR1_AT |  | 100.00 | 73.73 |
| BAR1_Nat |  |  | 100.00 |

TABLE 19

The nucleotide composition and GC:AT ratio of the artificial polynucleotide sequences for the bar gene sequence.

| BAR_AT | 139 | 130 | 144 | 139 | 1.01 |
|---|---|---|---|---|---|
| BAR_ZM | 122 | 156 | 154 | 120 | 1.28 |

Example 6

This example serves to illustrate DNA constructs for the expression of the artificial polynucleotides of the present invention in plants. A transgene DNA plant expression cassette comprises regulatory elements that control the transcription of a mRNA from the cassette. A plant expression cassette is constructed to include a promoter that functions in plants that is operably linked to a 5' leader region that is operably linked to a DNA sequence of interest operably linked to a 3' termination region. These cassettes are constructed in plasmid vectors, which can then be transferred into plants by *Agrobacterium* mediated transformation methods or other methods known to those skilled in the art of plant transformation. The following plasmid vector constructs are illustrated to provide examples of plasmids containing plant expression cassettes comprising the artificial polynucleotide molecules of the present invention and are not limited to these examples.

Figure 7:
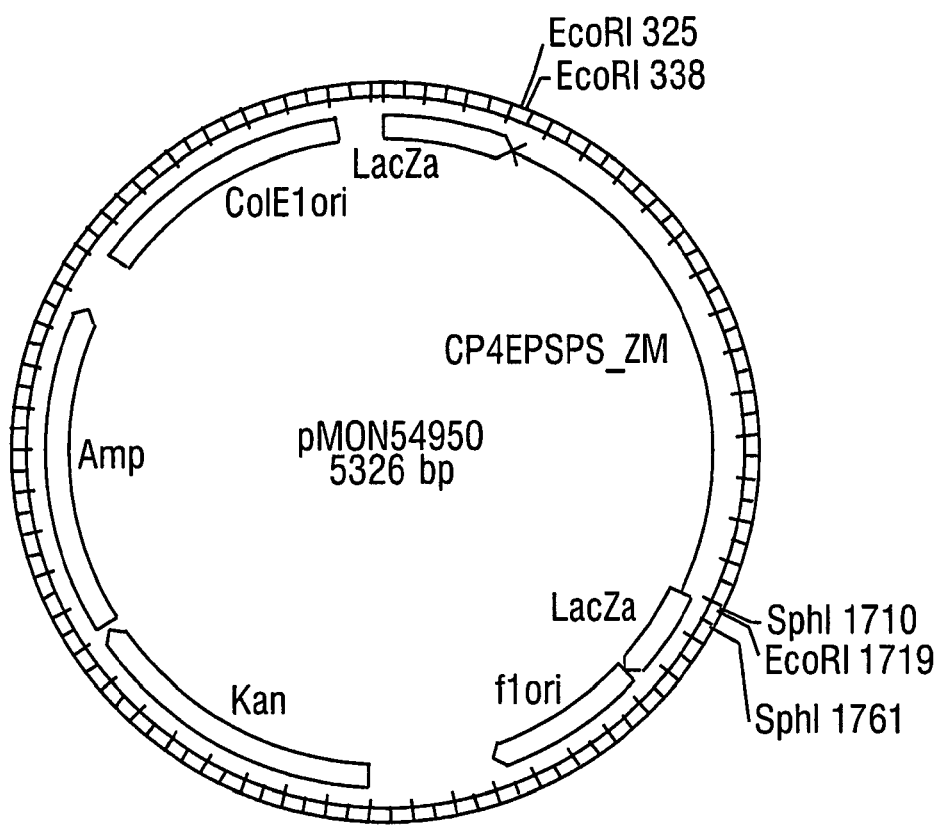
FIG. 7. Plasmid map of pMON54950.
Figure 8:
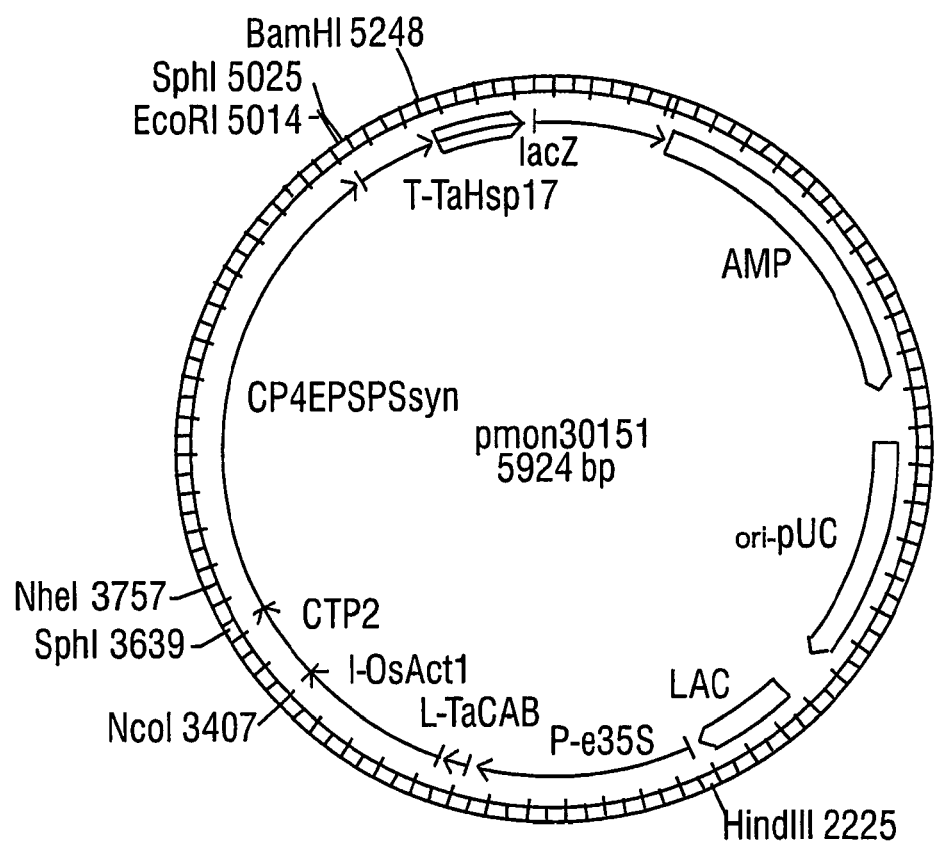
FIG. 8. Plasmid map of pMON30151.
Figure 9:
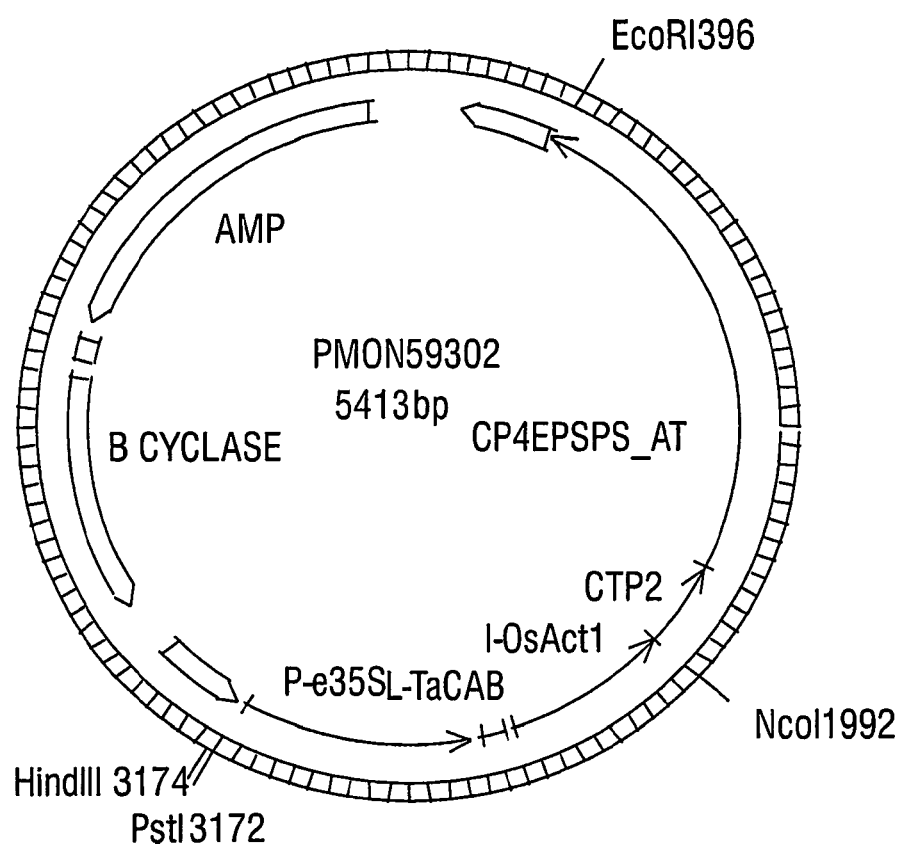
FIG. 9. Plasmid map of pMON59302.
Figure 10:
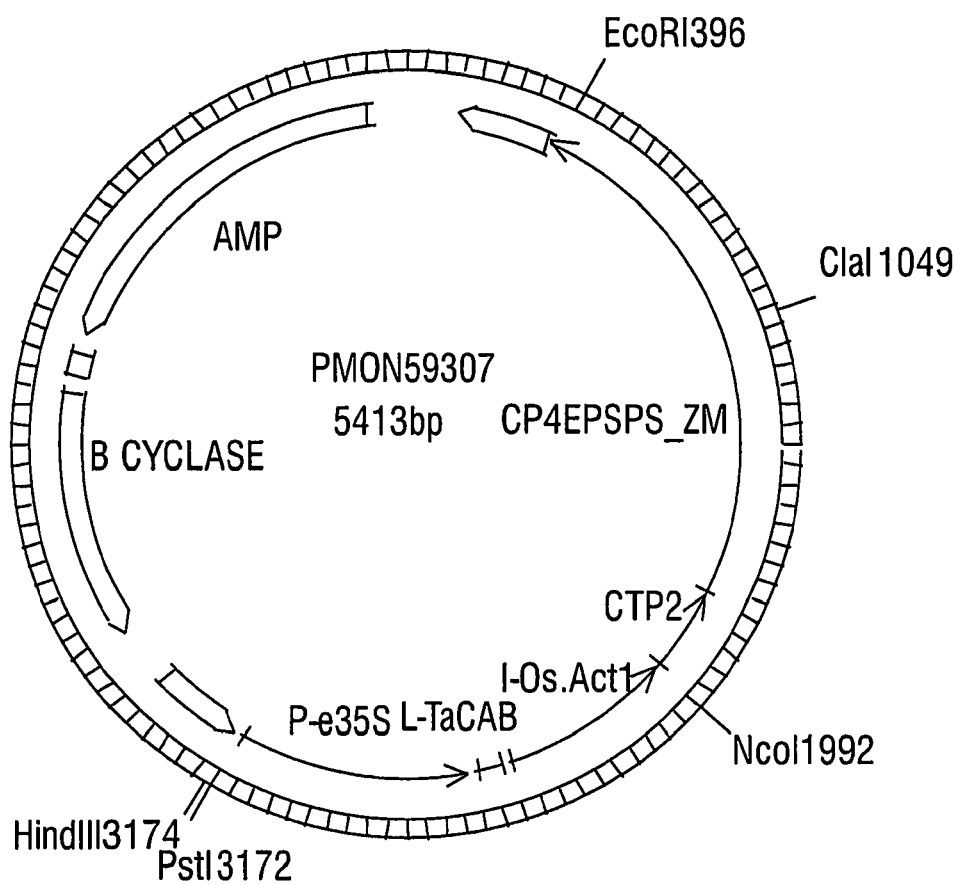
FIG. 10. Plasmid map of pMON59307.

The artificial polynucleotide molecules of the present invention, for example, CP4EPSPS_AT and CP4EPSPS_ZM are synthesized using overlapping primers. The full length product is then amplified with gene specific primers containing overhangs with SphI (forward primer) and EcoRI (reverse primer). Genes are cloned into the vector pCRII-TOPO (Invitrogen, CA). The resulting plasmids pMON54949 (CP4EPSPS_AT, FIG. 6) and pMON54950 (CP4EPSPS_ZM, FIG. 7) contain the artificial polynucleotide and these polynucleotides are sequenced using DNA sequencing methods to confirm that the modifications designed by the method of the present invention are contained in the artificial polynucleotides. In the next step, the artificial polynucleotide encoding the CTP2 chloroplast transit peptide is ligated to the 5' end of the CP4EPSPS polynucleotides. The CaMV 35S promoter with a duplicated enhancer (P-CaMVe35S) and a rice actin 1 intron (I-OsAct1) derived from pMON30151 (FIG. 8) by digestion with SphI and HindIII ligated to the CTP2CP4EPSPS polynucleotides to create plasmids pMON59302 (CTP2CP4EPSPS_AT, FIG. 9) and pMON59307 (CTP2CP4EPSPS_ZM, FIG. 10).

Figure 11:
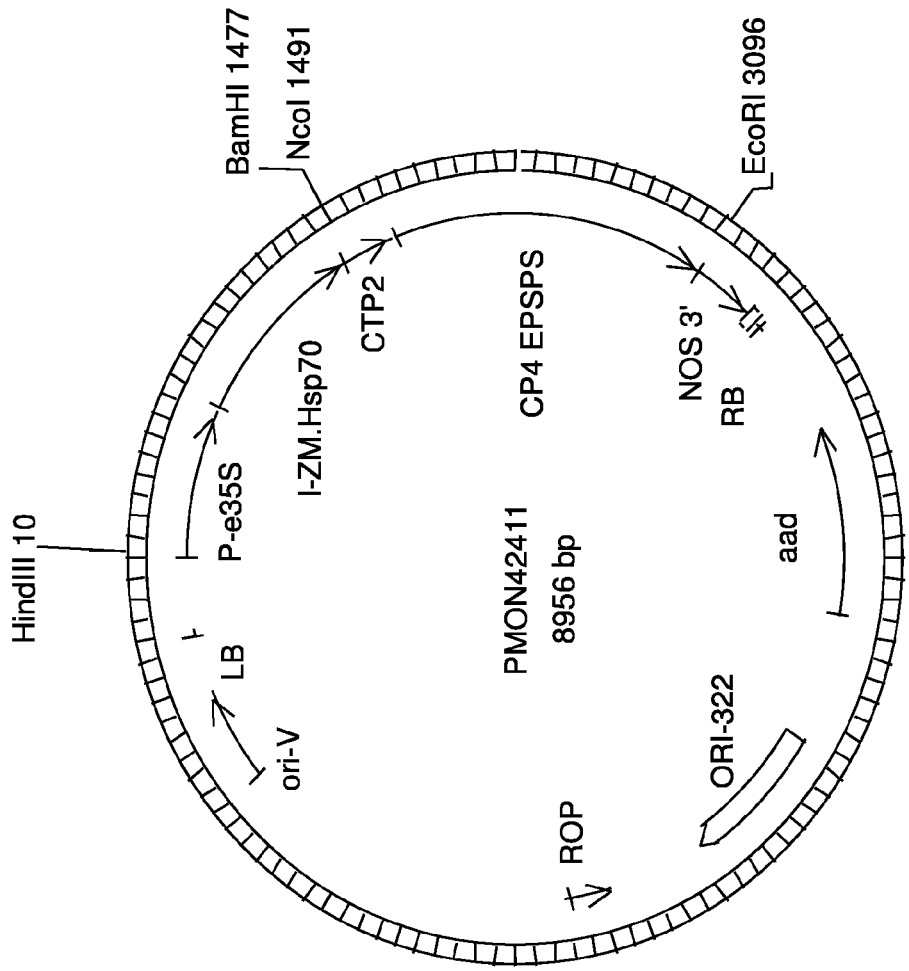
FIG. 11. Plasmid map of pMON42411.
Figure 12:
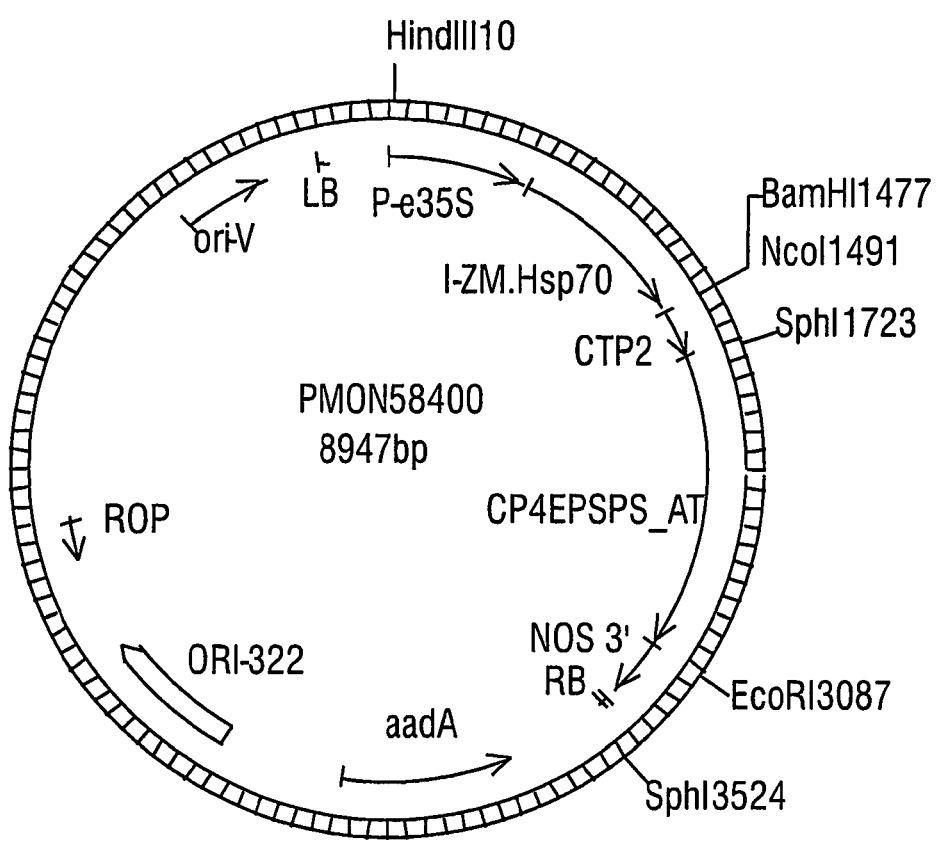
FIG. 12. Plasmid map of pMON58400.
Figure 13:
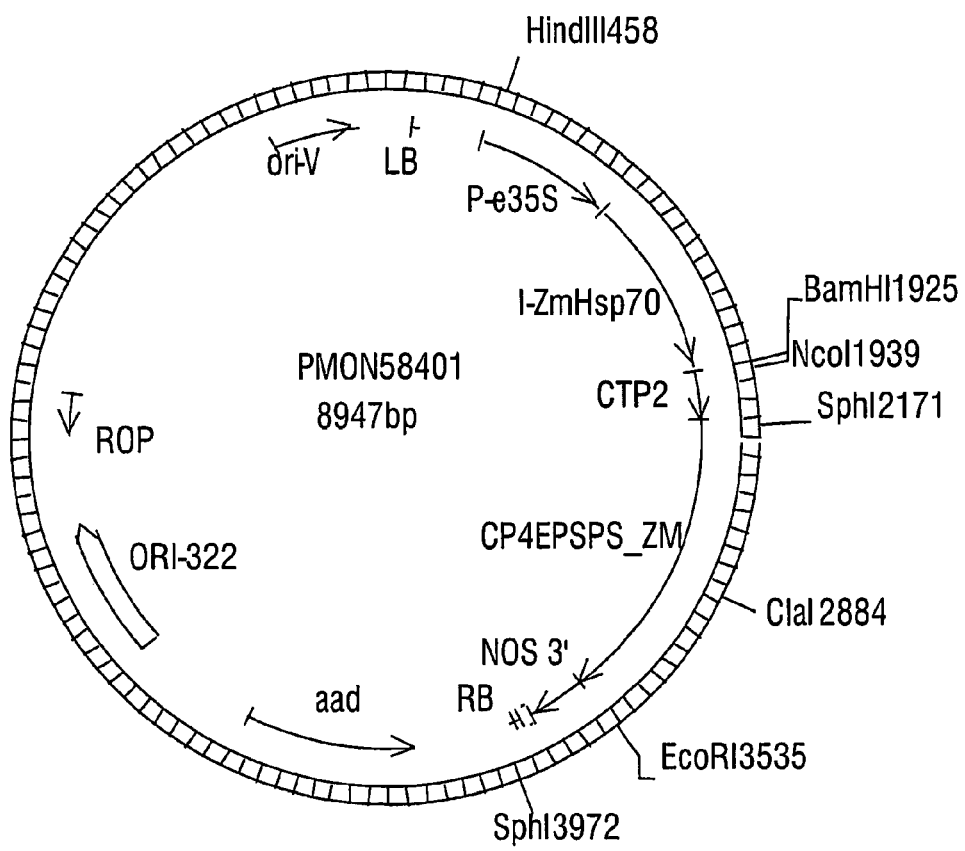
FIG. 13. Plasmid map of pMON58401.
Figure 14:
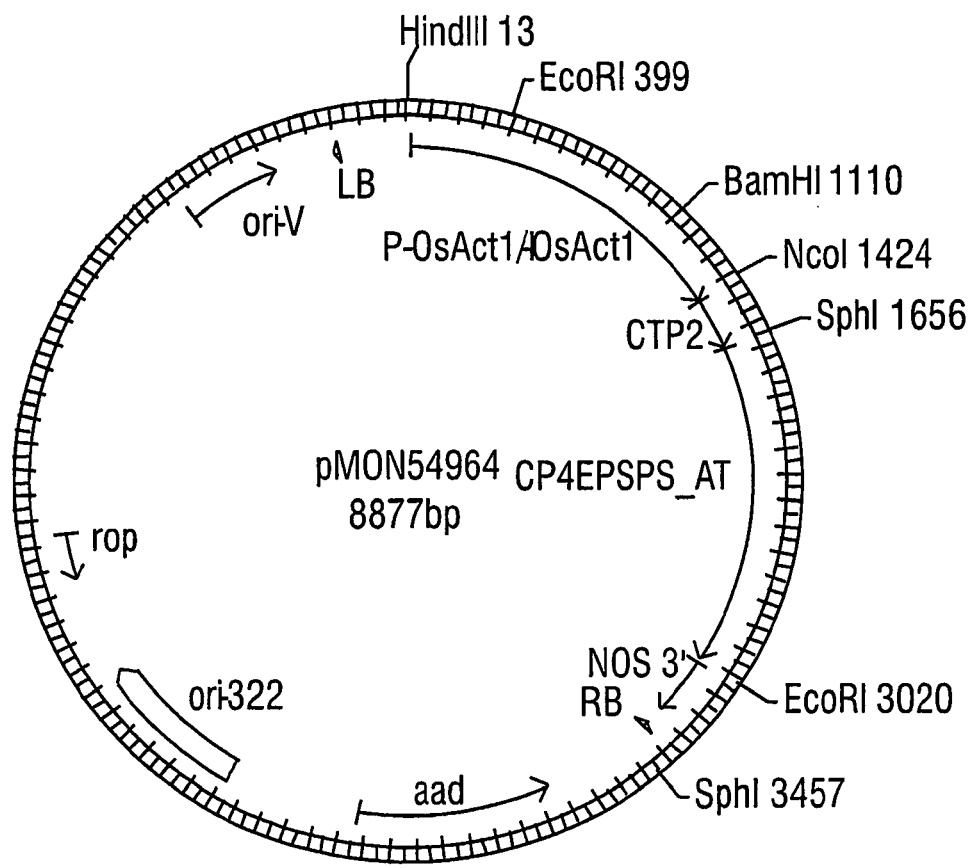
FIG. 14. Plasmid map of pMON54964.
Figure 15:
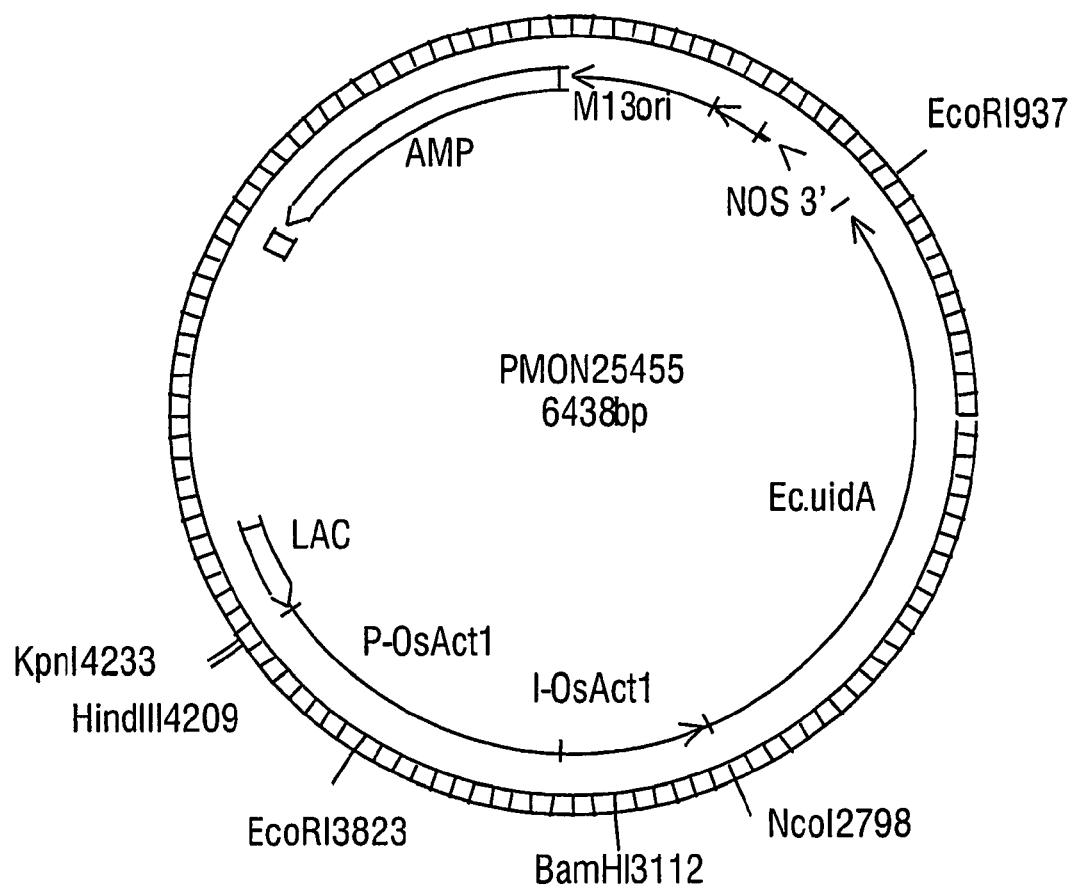
FIG. 15. Plasmid map of pMON25455.
Figure 16:
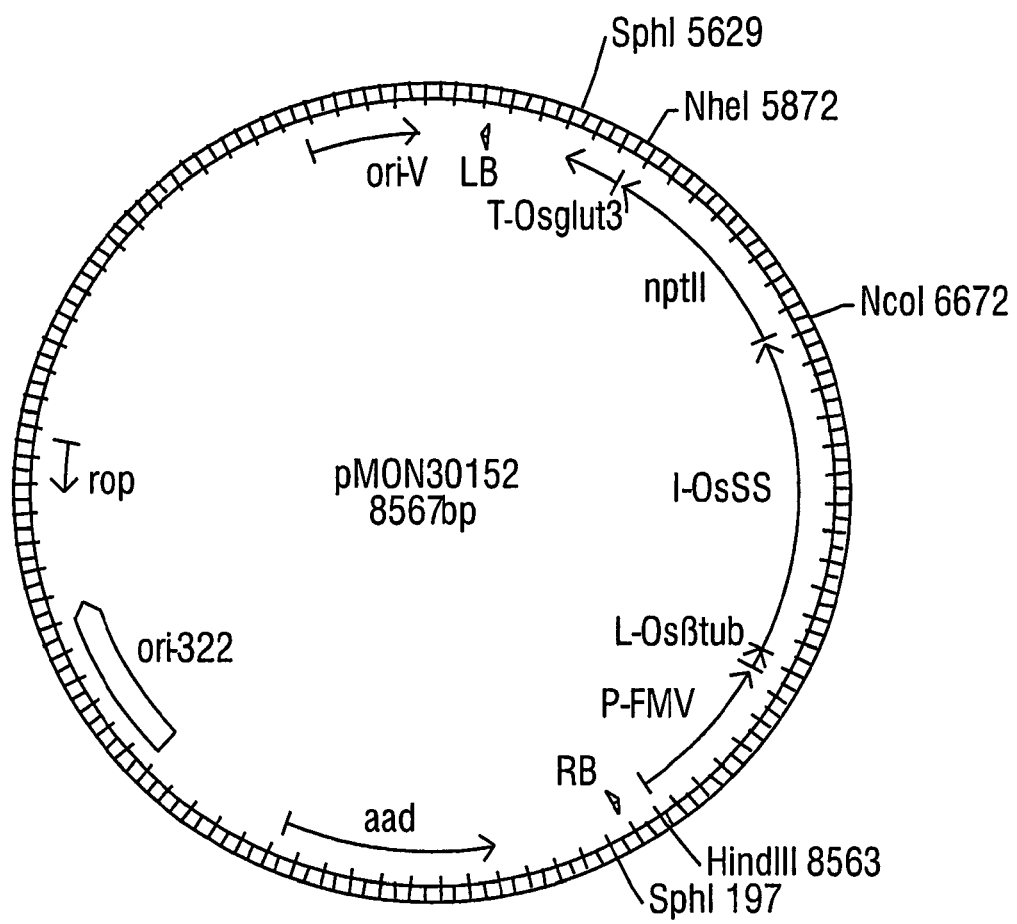
FIG. 16. Plasmid map of pMON30152.
Figure 17:
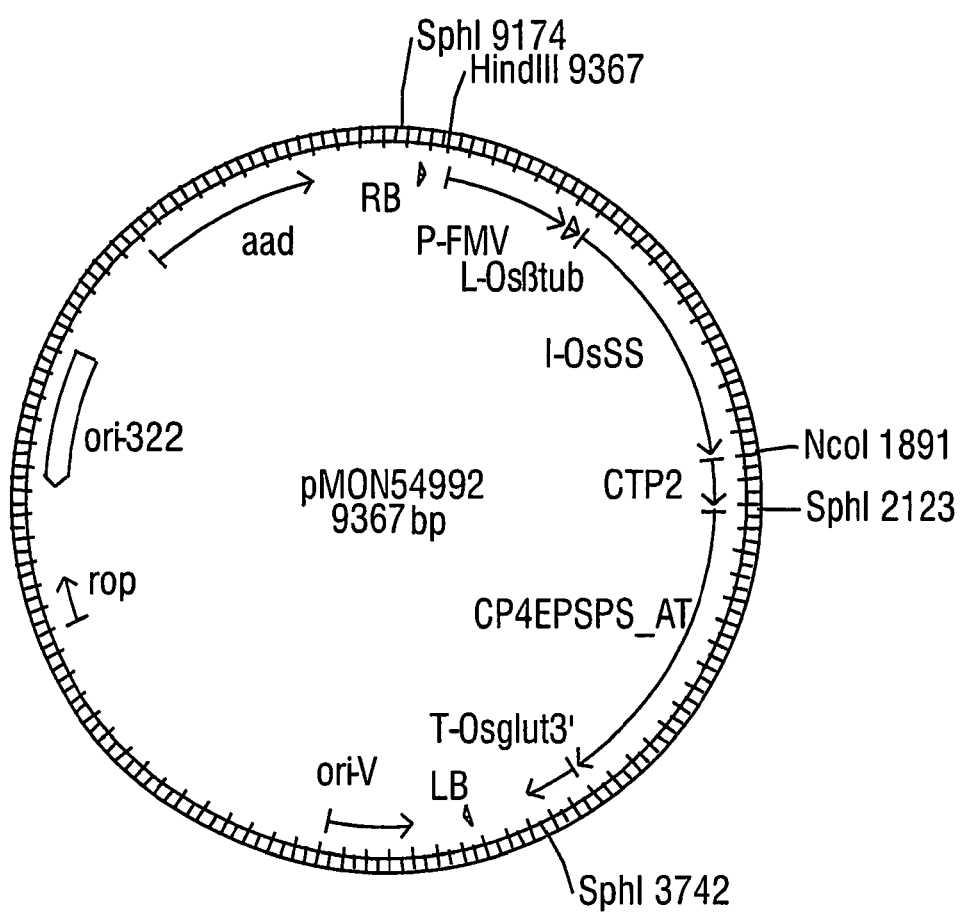
FIG. 17. Plasmid map of pMON54992.
Figure 18:
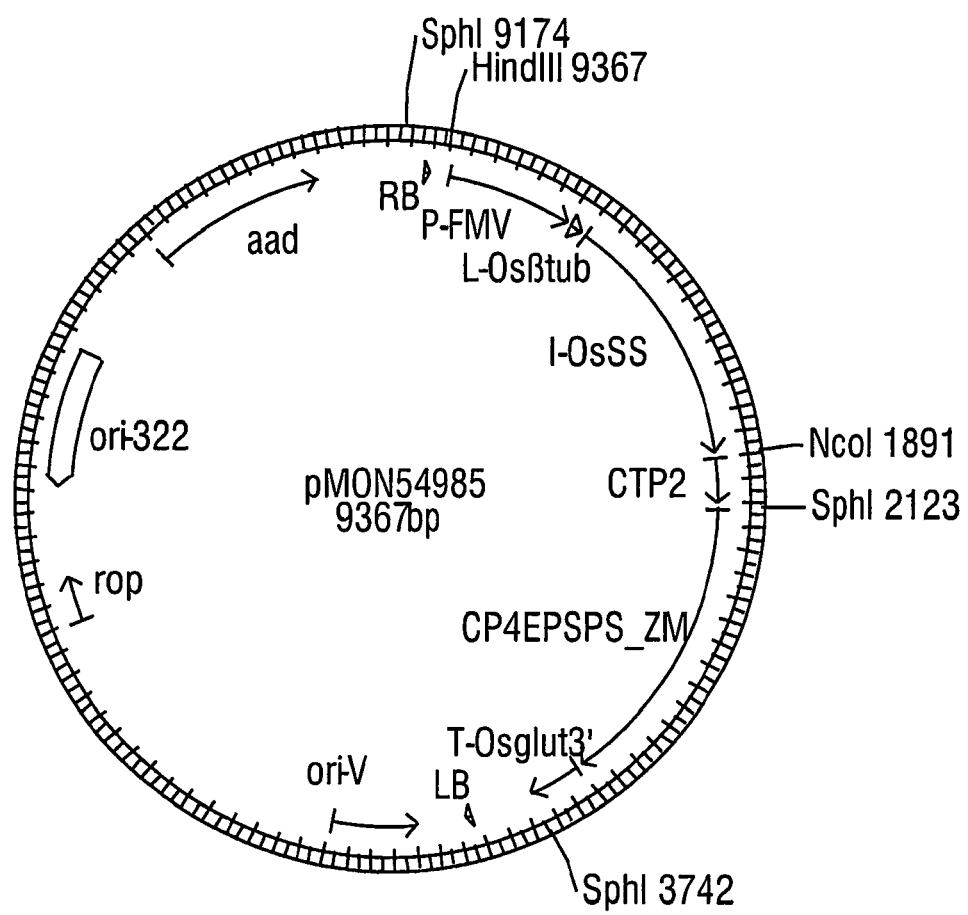
FIG. 18. Plasmid map of pMON54985.

For the expression of the new artificial polynucleotides in monocot plants, genes are placed in plant expression cassettes containing at the 5' end of the polynucleotide, a promoter and an intron, a 5' untranslated region, and at the 3' end of the polynucleotide a transcription termination signal. For this purpose, pMON42411 (FIG. 11) containing P-CaMV35S:en, I-HSP70, CTP2CP4_Nat and NOS 3' are digested with NcoI and EcoRI restriction enzymes. The pMON59302 (FIG. 9) and pMON59307 (FIG. 10) are digested with same restriction enzymes. Fragments are gel purified using Qiagen gel purification kit and ligated to form pMON58400 (CP4EPSPS_AT, FIG. 12) and pMON58401 (CP4EPSPS_ZM, FIG. 13). Additional vector pMON54964 (FIG. 14), containing P-OsAct1/I-OsAct1 is made by replacing P-e35S/I-Hsp70 from pMON58400 (FIG. 12) using HindIII/NcoI fragment from pMON25455 (FIG. 15). To create a monocot expression vector containing the P-FMV promoter, pMON30152 (FIG. 16) is digested with NheI, the ends are blunted with T4DNA polymerase in the presence of 4 dNTP-s (200 µM) and NcoI. The CPT2CP4_AT or CTP2CP4_ZM DNA fragments are isolated from pMON59302 (FIG. 9) or pMON59307 (FIG. 10), respectively by digesting with EcoRI, blunting with T4 DNA polymerase and NcoI digest. Gel purified DNA fragments are ligated and new plasmids pMON54992 (CTP2CP4_AT, FIG. 17) and pMON54985 (CTP2CP4_ZM, FIG. 18) are created. In each case the successful plasmid construction is confirmed by restriction endonuclease digestion, using among others ClaI (introduced to both artificial polynucleotides) and Pst I (introduced to CP4EPSPS_ZM). The CP4EPSPS_Nat present in parental vectors has both ClaI and two PstI restriction sites in coding region in different location than in artificial polynucleotides.

Figure 19:
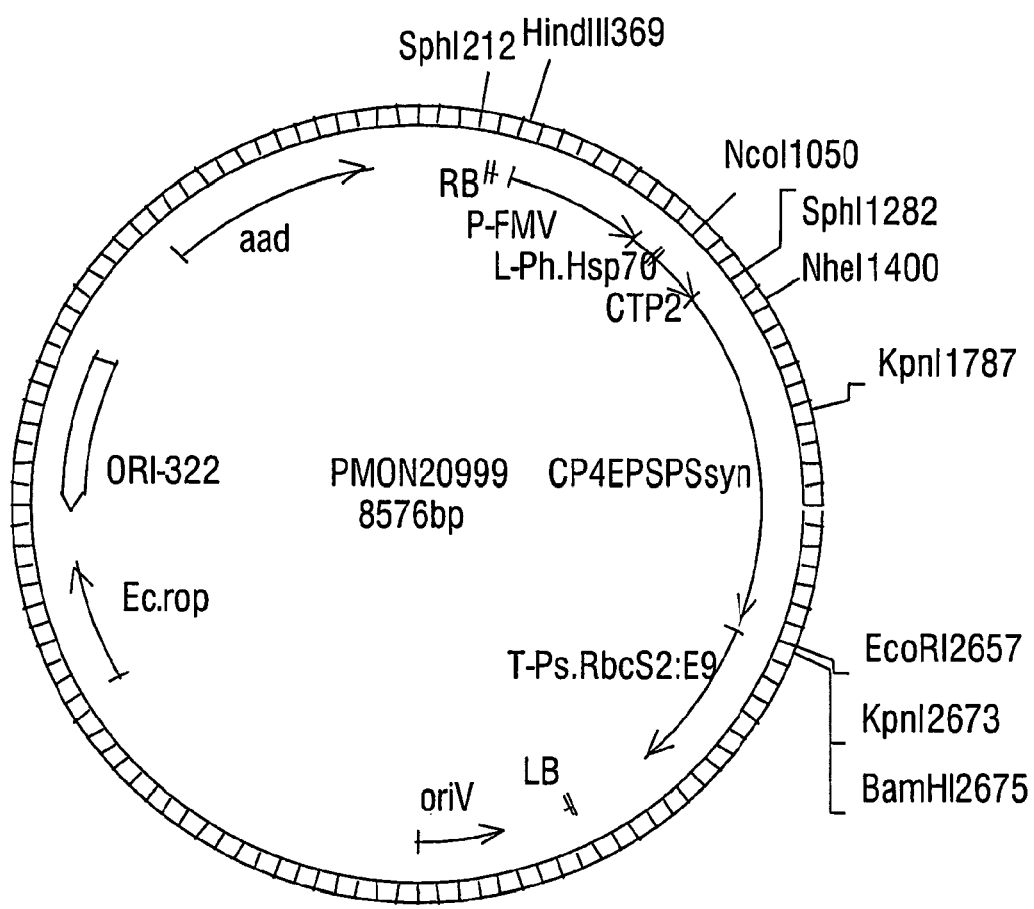
FIG. 19. Plasmid map of pMON20999.
Figure 20:
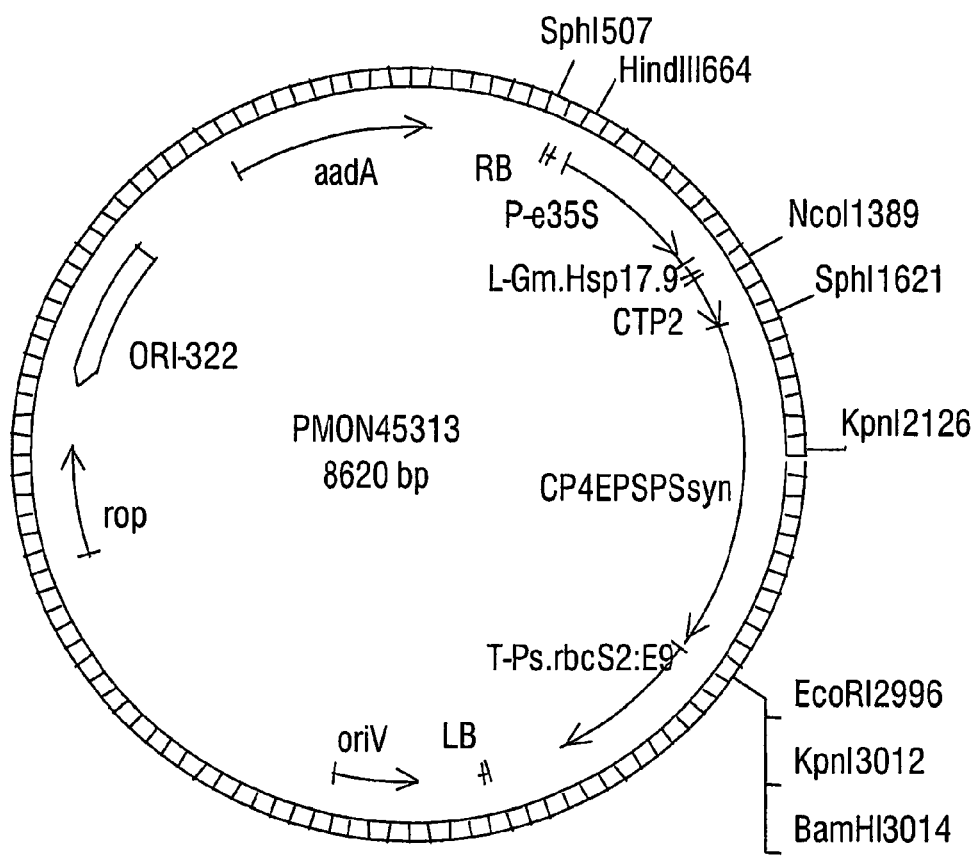
FIG. 20. Plasmid map of pMON45313.
Figure 21:
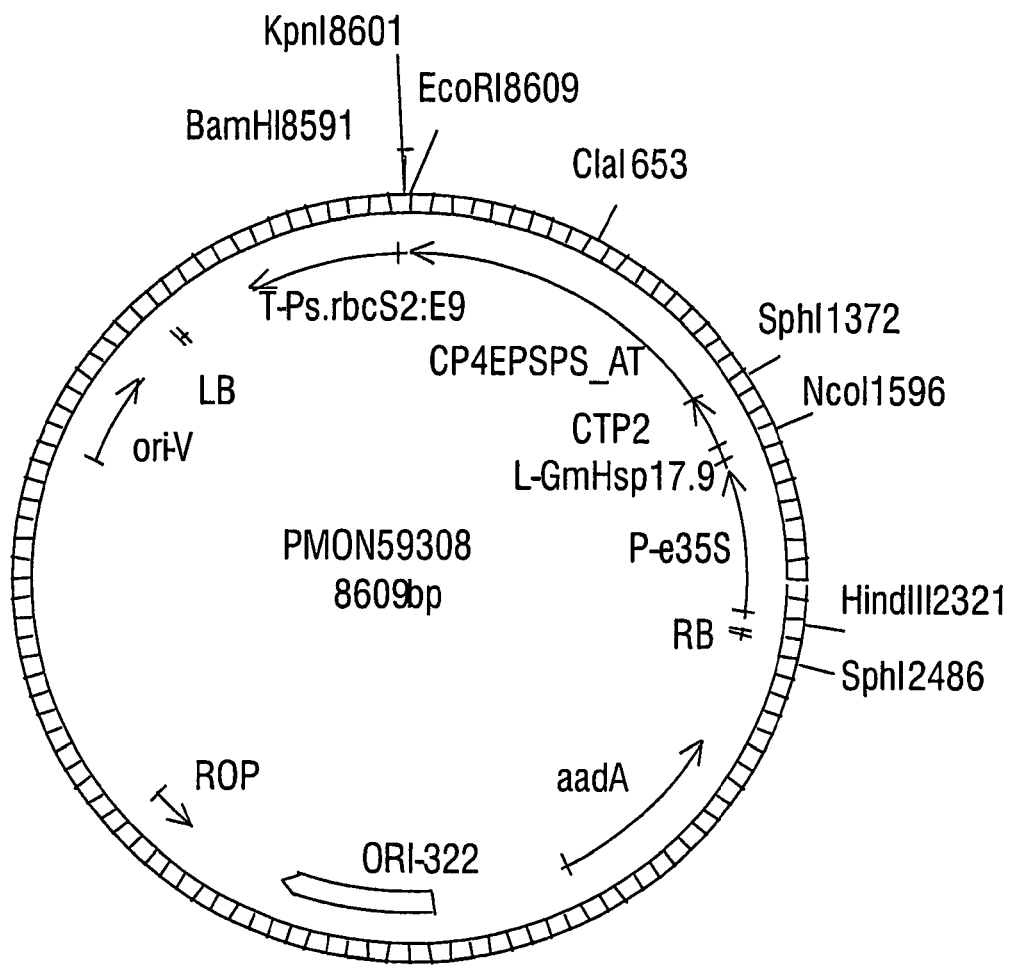
FIG. 21. Plasmid map of pMON59308.
Figure 22:
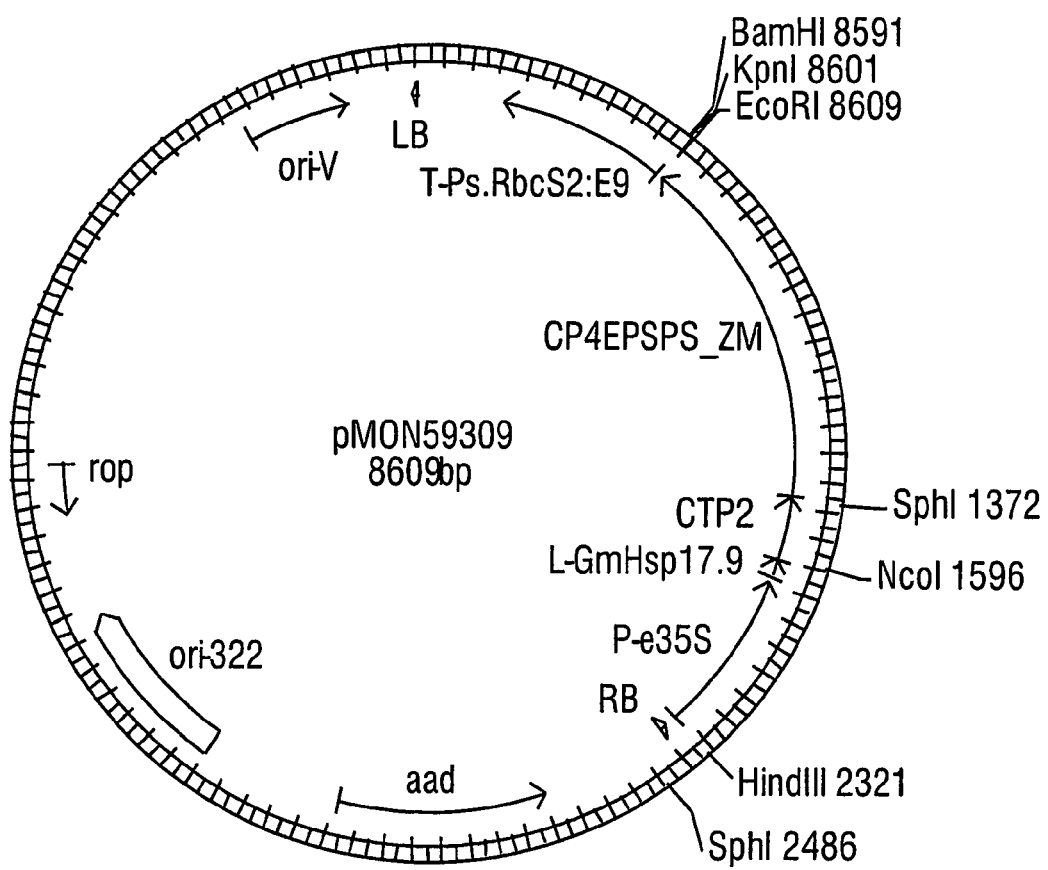
FIG. 22. Plasmid map of pMON59309.
Figure 23:
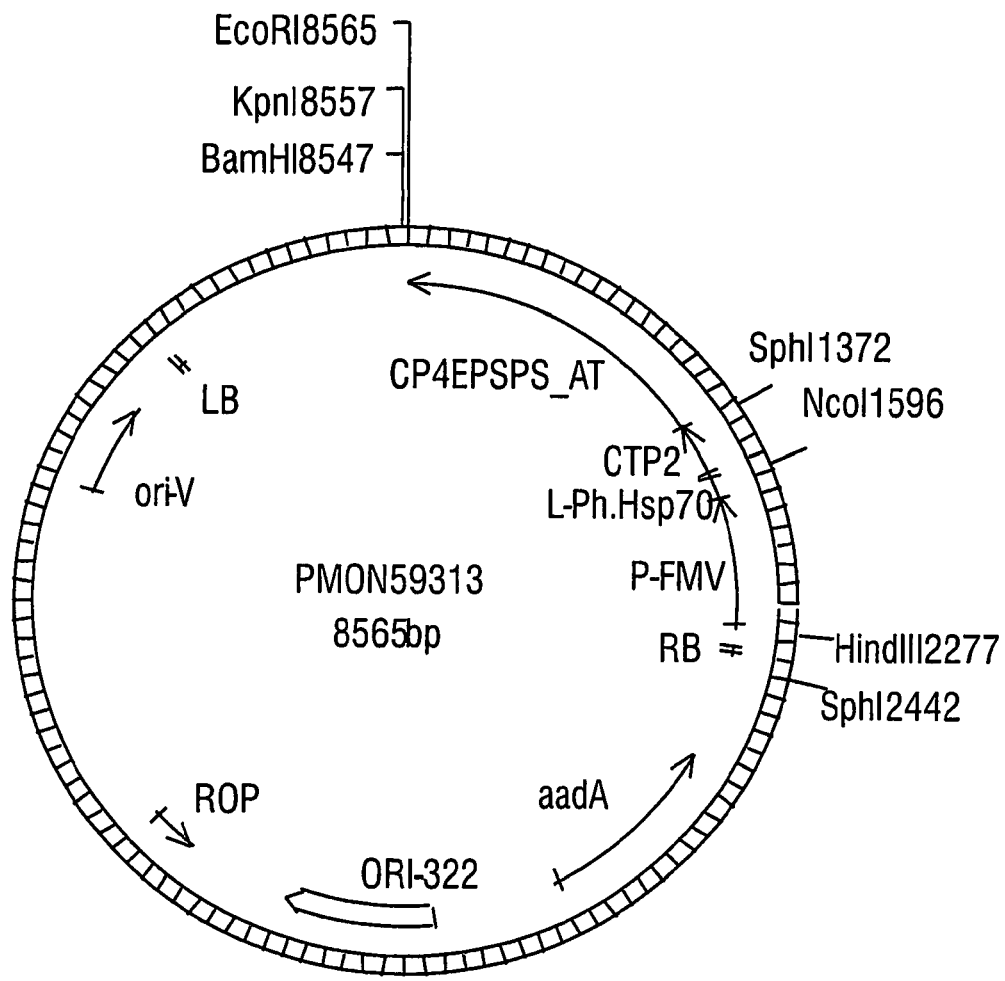
FIG. 23. Plasmid map of pMON59313.
Figure 24:
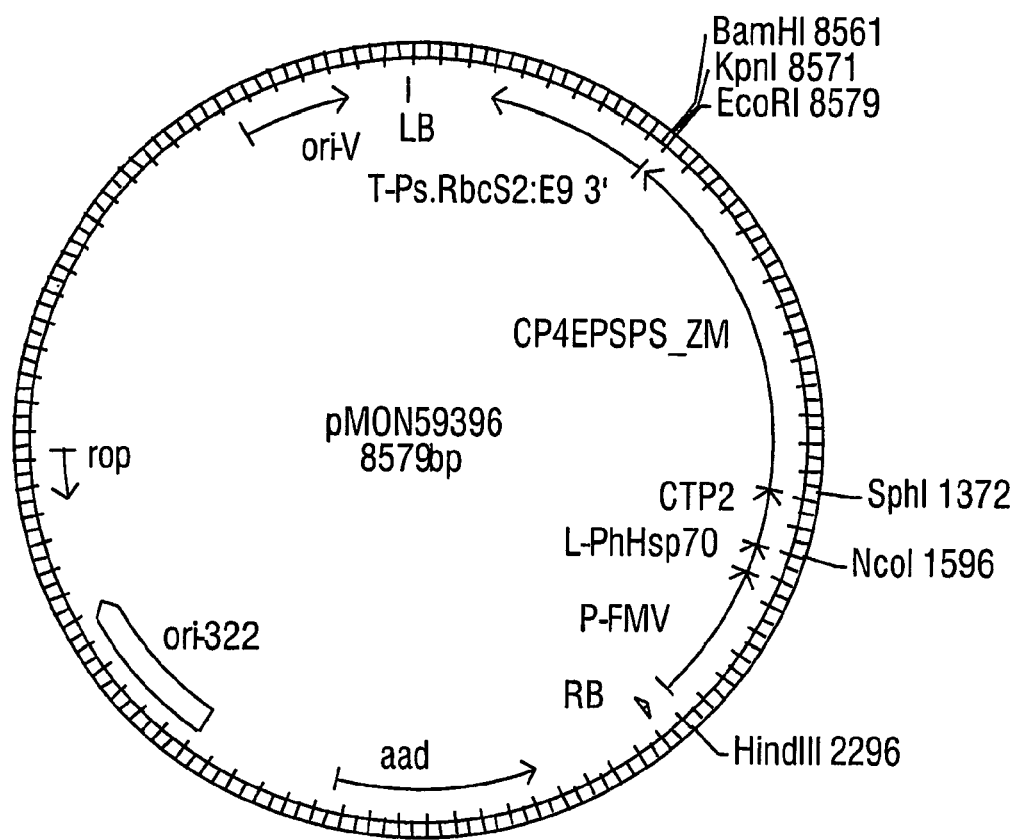
FIG. 24. Plasmid map of pMON59396.

For the expression of the artificial CP4EPSPS polynucleotides in dicot plants, two parental vectors are used: pMON20999 (P-FMV/CTP2CP4_Syn/3'E-9, FIG. 19) and pMON45313 (P-e35S/CTP2CP4_Syn/3'E9, FIG. 20). In each plasmid, a DNA fragment containing the CTP2CP4_Syn polynucleotide is replaced with CTP2CP4_AT or CTP2CP4_ZM. To create pMON59308 (P-CaMVe35S/CTP2CP4_AT, FIG. 21) or pMON59309 (P-CaMVe35S/CTP2CP4_ZM, FIG. 22), pMON45313 is digested with NcoI and EcoRI and the DNA restriction fragments derived from NcoI/EcoRI digest of pMON59302 (CTP2CP4_AT, FIG. 9) or pMON59307 (CTP2CP4_ZM, FIG. 10) are ligated, respectively. To create pMON59313 (P-FMV/CTP2CP4_AT/3'E9, FIG. 23) and pMON59396 (P-FMV/CTP2CP4_ZM/3'E9, FIG. 24) parental plasmid pMON20999 is digested with NcoI and BamHI to remove CTP2CP4_Syn and the restriction fragments NcoI/BamHI derived from pMON59308 (CTP2CP4_AT, FIG. 21) or pMON59309 (CTP2CP4_ZM, FIG. 22) are ligated, respectively.

Example 7

Figure 25:
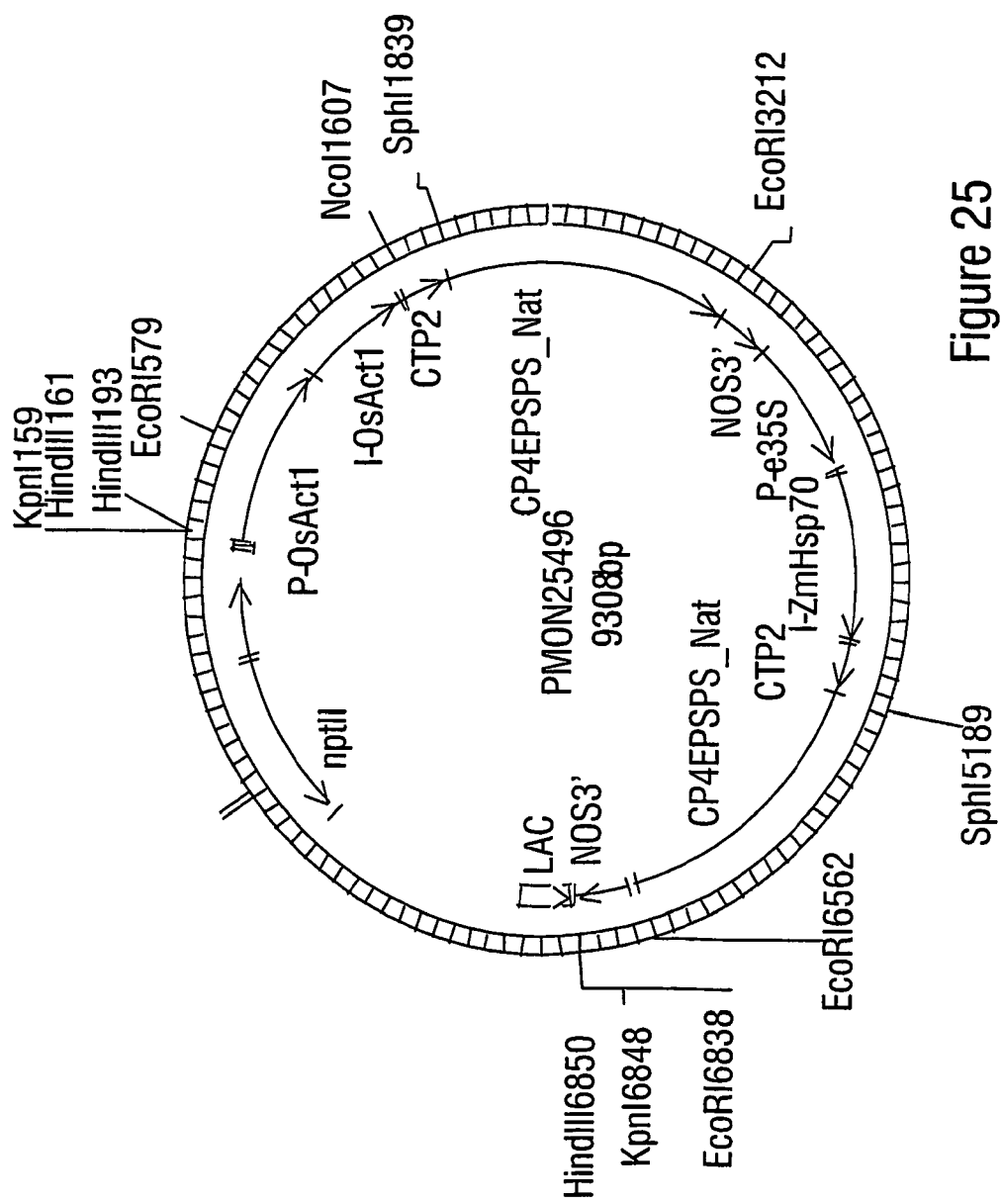
FIG. 25. Plasmid map of pMON25496.

The artificial polynucleotides are tested to determine efficacy for conferring glyphosate tolerance to transgenic plants. Five different expression cassettes (Table 20) with the new artificial CP4EPSPS polynucleotides are transformed into corn and the resulting transgenic corn plants compared to the commercial standard (Roundup Ready® Corn 603, Monsanto Co.). The plasmid pMON25496 (FIG. 25) contained in the commercial standard has two copies of the CP4EPSPS_Nat polynucleotide, the expression driven by the P-CaMVe35S (P-CaMVe35S) and P-OsAct1 promoters, respectively. The plasmids containing the new artificial CP4EPSPS polynucleotides contain only a single copy of the polynucleotide to be tested. The expression of these polynucleotides are driven by the P-CaMVe35S promoter with the heat shock protein intron I-Hsp70 or the P-FMV promoter with a rice sucrose synthase intron (I-OsSS).

Plasmid pMON54964 contains rice actin 1 promoter with first native intron (U.S. Pat. No. 5,641,876, herein incorporated by reference in its entirety).

These plasmids are transformed into corn cells by an *Agrobacterium* mediated method and transgenic corn lines regenerated on glyphosate selection. Transgenic corn plants can be produced by an *Agrobacterium* mediated transformation method. A disarmed *Agrobacterium* strain C58 (ABI) harboring a binary construct of the present invention is used. This is transferred into *Agrobacterium* by a triparental mating method (Ditta et al., Proc. Natl. Acad. Sci. 77:7347-7351). Liquid cultures of *Agrobacterium* are initiated from glycerol stocks or from a freshly streaked plate and grown overnight at 26° C.-28° C. with shaking (approximately 150 rpm) to mid-log growth phase in liquid LB medium, pH 7.0 containing the appropriate antibiotics. The *Agrobacterium* cells are resuspended in the inoculation medium (liquid CM4C) and the density is adjusted to $OD_{660}$ of 1. Freshly isolated Type II immature HiIIxLH198 and HiII corn embryos are inoculated with *Agrobacterium* containing a construct and co-cultured several days in the dark at 23° C. The embryos are then transferred to delay media and incubated at 28° C. for several or more days. All subsequent cultures are kept at this temperature. The embryos are transferred to a first selection medium containing carbenicillin 500/0.5 mM glyphosate). Two weeks later, surviving tissue are transferred to a second selection medium containing carbenicillin 500/1.0 mM glyphosate). Subculture surviving callus every 2 weeks until events can be identified. This may take about 3 subcultures on 1.0 mM glyphosate. Once events are identified, bulk up the tissue to regenerate. The plantlets are transferred to MSOD media in culture vessel and kept for two weeks. Then the plants with roots are transferred into soil. Those skilled in the art of corn transformation can modify this method to provide substantially identical transgenic corn plants containing the DNA compositions of the present invention.

About 30 transgenic corn lines for each plasmid construct are tested, and the transformation efficiency and expression levels of the CP4EPSPS enzyme are shown in Table 20. The transgenic corn lines are treated with glyphosate at a rate of 64 oz/acre as young plants, the surviving plants are assayed by CP4EPSPS ELISA (Padgette et al. Crop Sci. 35:1451-1461, 1995) to determine the CP4 EPSPS protein expression levels (CP4 exp %) shown in Table 20, and the level of expression is compared to the commercially available standard glyphosate tolerant corn plant (Roundup Ready® corn 603, Monsanto Co., St. Louis, Mo.) as a percent of the amount of protein expression determined in the commercial standard. Generally, more than 50% of corn lines survive the spray with 64 oz/acre glyphosate. The surviving plants are shown to have high level of CP4EPSPS expression that ranges from about 75 to 86% of commercial standard 603.

TABLE 20

Transformation efficiency (TE), CP4 expression (average %) derived from transformation of different CP4-alt constructs.

| pMON | Promoter/Intron # | TE (%) | CP4 exp (%)* |
|---|---|---|---|
| 58400 (CP4_AT) | P-CaMVe35S/IHsp70 | 5.4 | 75.5 |
| 58401 (CP4_ZM) | P-CaMVe35S/IHsp70 | 7.2 | 84.7 |
| 54964 (CP4_AT) | P-OsAct1 | 8.2 | 78.1 |
| 54985 (CP4_ZM) | P-FMV/IOsSS | 11.5 | 85.7 |
| 54992 (CP4_AT) | P-FMV/IOsSS | 11.5 | 78.2 |
| nk603 (control) | P-OsAct1/P-e35S: | — | 100 |

*CP4EPSPS expression is calculated as percent of control (603) done on plants that survived glyphosate spray (64 oz/acre).

Example 8

Three plasmid constructs are evaluated in transgenic cotton plants (Table 21). The control construct (pMON20999) contains P-FMV/CP4EPSPS_Syn this expression cassette is contained in the commercially available glyphosate tolerant cotton line 1445 (Roundup Ready® cotton, Monsanto Co., St. Louis, Mo.). The plasmid constructs, pMON59313 and pMON59396 containing the CP4EPSPS_AT and CP4EPSPS_ZM polynucleotides, respectively, are assayed for transformation efficiency and CP4EPSPS enzyme levels relative to the commercial glyphosate tolerant expression cassette. About fifty transgenic cotton lines are evaluated for each construct. The artificial CP4EPSPS_AT polynucleotide driven by the P-FMV promoter gives a higher percentage of plants with a single insert, and an increase in expression level of the CP4EPSPS enzyme relative to the pMON20999 expression cassette as measured by ELISA.

TABLE 21

Transformation efficiency (TE), average CP4EPSPS expression in R0 cotton lines derived from transformation of different CP4EPSPS constructs.

| pMON | Promoter | TE (%) | CP4 Exp (%) |
|---|---|---|---|
| 20999 (CP4EPSPS_Syn) | P-FMV | 15.0 | 100.0 |
| 59313 (CP4EPSPS_AT) | P-FMV | 15.0 | 116.4 |
| 59396 (CP4EPSPS_ZM) | P-FMV | 16.1 | 52.0 |

Example 9

Constructs containing the artificial CP4EPSPS polynucleotides, CP4EPSPS_AT and CP4EPSPS_ZM are evaluated in soybean (Table 22). The plasmid constructs all contain the P-FMV promoter to drive expression of the new CP4EPSPS polynucleotides and are compared to the P-FMV/CP4EPSPS_Syn contained in pMON20999. About 25 to 30 transgenic soybean plants are produced for each construct. The transformation efficiency and CP4EPSPS enzyme, levels are measured. A surprisingly high expression level of CP4EPSPS protein is measured in soybean plants containing the CP4EPSPS_ZM coding sequence (Table 22).

TABLE 22

Transformation efficiency (TE), average CP4 expression derived from transformation of different CP4EPSPS constructs.

| pMON | Promoter | TE (%) | CP4Exp (%) |
|---|---|---|---|
| 20999 (CP4_Syn) | P-FMV | 0.55 | 100.0 |
| 59313 (CP4_AT) | P-FMV | 0.40 | 66.6 |
| 54996 (CP4_ZM) | P-FMV | 0.29 | 242.5 |

Example 10

Tobacco cells are transformed with three plasmid constructs containing different CP4EPSPS polynucleotide sequences and regenerated into plants. About twenty transgenic lines are evaluated from each construct. Expression from each of the CP4EPSPS polynucleotides is driven by the P-CaMVe35S duplicated enhancer promoter (Table 23). The transformation efficiency and CP4EPSPS enzyme expression level is measured. The different CP4EPSPS polynucleotide constructs are shown to perform about the same in transgenic tobacco for transformation efficiency and expression.

TABLE 23

Transformation efficiency (TE), average CP4 expression in R0 tobacco lines derived from transformation of different CP4 EPSPS constructs.

| pMON | Promoter | TE (%) | CP4 exp. (%) |
|---|---|---|---|
| 59308 CP4EPSPS_AT | P-CaMVe35S | 35 | 100.0 |
| 59309 CP4EPSPS_ZM | P-CaMVe35S | 35 | 91.0 |
| 54313 CP4EPSPS_Syn | P-CaMVe35S | 35 | 100.0 |

Example 11

Arabidopsis thaliana is transformed with four plasmid constructs by vacuum infiltration (Bechtold N, et al., CR Acad Sci Paris Sciences di la vie/life sciences 316: 1194-1199, (1993) and V1 progeny evaluated to compare efficacy of the different CP4EPSPS polynucleotide sequences and different promoters for the use in selection of plants on glyphosate (Table 24). About 30 transgenic V1 plants (+) are produced for each construct. The constructs driven by P-CaMVe35S with the duplicated enhancer (pMON45313, pMON59308, and pMON59309) show no substantial difference in the level of expression in leaves as determined by ELISA. The plants are transformed with pMON26140 that contains CP4EPSPS_Syn driven by the P-FMV promoter, these plants show the highest expression level, the expression levels detected from the plants of the test constructs are compared to pMON26140.

TABLE 24

Evaluation of different CP4 expression cassettes in Arabidopsis

| pMON | Promoter/ | Plants produced | CP4 exp.(%) |
|---|---|---|---|
| 45313(CPEPSPS4_Syn) | P-CaMVe35S | + | 82.1 |
| 59308(CP4EPSPS_AT) | P-CaMVe35S | + | 79.3 |
| 59309(CP4EPSPS_ZM) | P-CaMVe35S | + | 77.3 |
| 26140(CP4EPSPS_Syn) | P-FMV | + | 100.0 |

Example 12

Wheat plants transformed with the new CP4EPSPS polynucleotides are compared for transformation efficiency and CP4EPSPS enzyme expression determined by ELISA (Table 25). The CP4EPSPS_ZM provides at least seven times higher CPEPSPS enzyme expression than CP4EPSPS_AT. The average expression of CP4EPSPS in leaves from wheat plants containing the CP4EPSPS_ZM polynucleotide is about 64% of that found in glyphosate resistant wheat that contains a double cassette construct, pMON30139: P-e35S/I-Hsp70/CP4EPSPS_Nat and P-OsAct1/I-OsAct1/CP4EPSPS_Nat (WO/0022704).

TABLE 25

Performance of different CP4EPSPS polynucleotides in wheat

| pMON | Promoter/Intron | TE (%) | CP4 Exp. (%) |
|---|---|---|---|
| 58400 CP4EPSPS_AT | P-e35S/I-Hsp70 | 0.25 | 9.2 |
| 58401 CP4EPSPS_ZM | P-e35S/I-Hsp70 | 0.35 | 64.0 |
| 30139 CP4EPSPS_Nat | P-e35S:P-OsAct1 | — | 100.0 |

Example 13

This example serves to illustrate detection of different artificial polynucleotides in transgenic plants, specifically CP4EPSPS_AT and CP4EPSPS_ZM. The other artificial polynucleotides, OsEPSPS_AT, OsEPSPS_ZM, GmEPSPS_GM, ZmEPSPS_ZM, CTP2_AT, CTP2_ZM, Bar1_AT and Bar1_ZM can all be specifically detected in transgenic plants by methods that provide a DNA amplicon or by hybridization of a DNA probe to a plant sample. Those skilled in the art of DNA detection can easily design primer molecules from the artificial polynucleotide sequences provided in the present invention to enable a method that will specifically detect the artificial polynucleotide in a plant sample. The use of a method or a kit that provides DNA primers or probes homologous or complementary to the artificial polynucleotides disclosed herein is an aspect of the present invention.

A DNA detection method (polymerase chain reaction, PCR) is designed to detect the artificial CP4EPSPS polynucleotides in transgenic plants. The unique sets of DNA primers shown in Table 26 are designed to amplify a specific CP4EPSPS polynucleotide and to provide distinctly sized amplicons. The amplicons differ sufficiently in polynucleotide length among the various CP4EPSPS polynucleotides to make easy separation of the amplicons by standard agarose gel electrophoresis. The presence of more than one of the artificial polynucleotides can be detected in a plant by using a multiplex PCR method.

TABLE 26

Sequence of primers used for detection of different CP4 genes in transgenic plants.

| Primer pair: | Gene specificity | PCR product (bps) |
|---|---|---|
| SEQ ID NOs: 24 and 25 | CP4EPSPS_AT | 938 (940) |
| SEQ ID NOs: 26 and 27 | CP4EPSPS_ZM | 595 (600) |
| SEQ ID NOs: 28 and 29 | CP4EPSPS_Nat | 712 (710) |
| SEQ ID NOs: 30 and 31 | CP4EPSPS_Syn | 443 (440) |

DNA primer pairs (Table 26) are used to produce an amplicon diagnostic for a specified CP4EPSPS polynucleotide contained in a transgenic plant. These primer pairs include, but are not limited to SEQ ID NO:24 and SEQ ID NO:25 for the CP4EPSPS_AT polynucleotide; SEQ ID NO:26 and SEQ ID NO:27 for the CP4EPSPS_ZM; SEQ ID NO:28 and SEQ ID NO:29 for CP4EPSPS_Nat and SEQ ID NO:30 and SEQ ID NO:31 CP4EPSPS_Syn polynucleotide molecule. In addition to these primer pairs, any primer pair derived from SEQ ID NO:17 or SEQ ID NO:18 that when used in a DNA amplification reaction produces a DNA amplicon diagnostic for the respective CP4EPSPS polynucleotide is an aspect of the present invention.

The amplification conditions for this analysis is illustrated in Table 27 and Table 28, however, any modification of these conditions including the use of fragments of the DNA molecules of the present invention or complements thereof as primer molecules, which produce an amplicon DNA molecule diagnostic for the artificial polynucleotides described herein is within the ordinary skill of the art. The DNA molecules of the present invention include at least SEQ ID NO:3, SEQ ID NO:4, SEQ ID NO:7, SEQ ID NO:10, SEQ ID NO:13; SEQ ID NO:14, SEQ ID NO:17, SEQ ID NO:18, SEQ ID NO:21, SEQ ID NO:22, and SEQ ID NO:35. DNA molecules that function as primer molecules in a DNA amplification method to detect the presence of the artificial polynucleotides include, but are not limited to SEQ ID NO:24, SEQ ID NO:25, SEQ ID NO:26, SEQ ID NO:27, SEQ ID NO:28, SEQ ID NO:29, SEQ ID NO:30, and SEQ ID NO:31.

In a method for determining the presence of polynucleotides of the present invention, the analysis of plant tissue DNA extract sample should include a positive control known to contain the artificial polynucleotide, and a negative DNA extract control from a plant that is not transgenic or does not contain the artificial polynucleotide, and a negative control that contains no template in the DNA extract.

Additional DNA primer molecules of sufficient length can be selected from SEQ ID NO:17 and SEQ ID NO:18 and conditions optimized for the production of an amplicon that may differ from the methods shown in Table 27 and Table 28, but result in an amplicon diagnostic for the artificial polynucleotides. The use of these DNA primer sequences homologous or complementary to SEQ ID NO:17 and SEQ ID NO:18 used with or without modifications to the methods of Table 27 and 28 are within the scope of the invention. The assay for the CP4EPSPS_AT and CP4EPSPS_ZM amplicon can be performed by using a Stratagene Robocycler, MJ Engine, Perkin-Elmer 9700, or Eppendorf Mastercycler Gradient thermocycler as shown in Table 28, or by methods and apparatus known to those skilled in the art.

TABLE 28

Suggested PCR parameters for different thermocyclers

Gently mix and, if needed (no hot top on thermocycler), add 1-2 drops of mineral oil on top of each reaction. Proceed with the PCR in a Stratagene Robocycler, MJ Engine, Perkin-Elmer 9700, or Eppendorf Mastercycler Gradient thermocycler using the following cycling parameters.

| Cycle No. | Settings: Stratagene Robocycler | |
|---|---|---|
| 1 | 94° C. | 3 minutes |
| 38 | 94° C. | 1 minute |
|  | 60° C. | 1 minute |
|  | 72° C. | 1 minute and 30 seconds |
| 1 | 72° C. | 10 minutes |

| Cycle No. | Settings: MJ Engine or Perkin-Elmer 9700 | |
|---|---|---|
| 1 | 94° C. | 3 minutes |
| 38 | 94° C. | 10 seconds |
|  | 60° C. | 30 seconds |
|  | 72° C. | 1 minute |
| 1 | 72° C. | 10 minutes |

| Cycle No. | Settings: Eppendorf Mastercycler Gradient | |
|---|---|---|
| 1 | 94° C. | 3 minutes |
| 38 | 94° C. | 15 seconds |
|  | 60° C. | 15 seconds |

TABLE 27

DNA amplification procedure and reaction mixture for the confirmation of artificial EPSPS polynucleotide CP4EPSPS_AT in corn plants.

| Step | Reagent | Amount | Comments |
|---|---|---|---|
| 1 | Nuclease-free water | add to final volume of 20 μl | — |
| 2 | 10X reaction buffer (with MgCl$_2$) | 2.0 μl | 1X final concentration of buffer, 1.5 mM final concentration of MgCl$_2$ |
| 3 | 10 mM solution of dATP, dCTP, dGTP, and dTTP | 0.4 μl | 200 μM final concentration of each dNTP |
| 4 | primer (SEQ ID NO: 24) (resuspended in 1X TE buffer or nuclease-free water to a concentration of 10 μM) | 0.4 μl | 0.2 μM final concentration |
| 5 | primer (SEQ ID NO: 25) (resuspended in 1X TE buffer or nuclease-free water to a concentration of 10 μM) | 0.4 μl | 0.2 μM final concentration |
| 6 | control primer (SEQ ID NO: 32) (resuspended in 1X TE buffer or nuclease-free water to a concentration of 10 μM) | 0.2 μl | 0.1 μM final concentration |
| 7 | control primer (SEQ ID NO: 33) (resuspended in 1X TE buffer or nuclease-free water to a concentration of 10 μM) | 0.2 μl | 0.1 μM final concentration |
| 8 | RNase, DNase free (500 ng/μl) | 0.1 μl | 50 ng/reaction |
| 9 | REDTaq DNA polymerase (1 unit/μl) | 1.0 μl (recommended to switch pipets prior to next step) | 1 unit/reaction |
| 10 | Extracted DNA (template): Samples to be analyzed |  | — |
|  | individual leaves | 10-200 ng of genomic DNA |  |
|  | pooled leaves (maximum of 50 leaves/pool) | 200 ng of genomic DNA |  |
|  | Negative control | 50 ng of nontransgenic plant genomic DNA |  |
|  | Negative control | no template DNA |  |
|  | Positive control | 5 ng plasmid DNA |  |

TABLE 28-continued

Suggested PCR parameters for different thermocyclers

| | 72° C. | 1 minute |
| 1 | 72° C. | 10 minutes |

Note:
The MJ Engine or Eppendorf Mastercycler Gradient thermocycler should be run in the calculated mode. Run the Perkin-Elmer 9700 thermocycler with the ramp speed set as maximum.

All of the compositions and methods disclosed and claimed herein can be made and executed in light of the present disclosure. While the compositions and methods of this invention have been described, it will be apparent to those of skill in the art that variations may be applied to the compositions and methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

All publications and patent applications cited herein are incorporated by reference in their entirely to the same extent as if each individual publication or patent application is specifically and individually indicated to be incorporated by reference.

The invention claimed is:

1. A method to avoid silencing of a transgene comprising SEQ ID NO:16 operably linked to a polynucleotide encoding a chloroplast transit peptide in transgenic plants comprising the steps of:
   (a) obtaining a DNA construct comprising an artificial polynucleotide molecule comprising a nucleic acid encoding the EPSPS polypeptide encoded by SEQ ID NO:35 operably linked to a polynucleotide encoding a chloroplast transit peptide;
   (b) transforming a plant cell with said DNA construct; and
   (c) regenerating said plant cell into a fertile transgenic plant,
wherein said fertile transgenic plant comprises both said artificial polynucleotide and said transgene.

2. The method of claim 1, wherein said polynucleotide encoding the chloroplast transit peptide is SEQ ID NO:13.

3. An artificial polynucleotide molecule comprising SEQ ID NO:35.

4. A DNA construct comprising: a promoter molecule that functions in plants, operably linked to said artificial polynucleotide molecule of claim 3.

5. A plant cell, plant or progeny thereof comprising the DNA construct of claim 4.

6. The plant or progeny thereof of claim 5, wherein said plant is selected from the group consisting of wheat, corn, rice, soybean, cotton, potato, canola, turf grass, forest trees, grain sorghum, vegetable crops, ornamental plants, forage crops, and fruit crops.

7. A plant cell comprising at least a first and a second polynucleotide, wherein the first polynucleotide comprises SEQ ID NO:35, and wherein the second polynucleotide comprises SEQ ID NO:16 operably linked to a polynucleotide encoding a chloroplast transit peptide.

8. A plant or progeny thereof comprising said plant cell of claim 7.

9. A plant cell, seed, plant or progeny thereof comprising SEQ ID NO:35.

10. A method of regenerating a fertile transgenic plant comprising the steps of:
   (a) obtaining said plant cell of claim 7; and
   (b) regenerating said plant cell into a fertile transgenic plant, wherein said fertile transgenic plant comprises both said polynucleotides.

* * * * *